US010905120B2

(12) United States Patent
Cutler et al.

(10) Patent No.: US 10,905,120 B2
(45) Date of Patent: Feb. 2, 2021

(54) ABA RECEPTOR AGONISTS THAT MODULATE TRANSPIRATION

(71) Applicant: The Regents of the University of California, Oakland, CA (US)

(72) Inventors: Sean R. Cutler, Riverside, CA (US); Aditya Vaidya, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 341 days.

(21) Appl. No.: 15/824,760

(22) Filed: Nov. 28, 2017

(65) Prior Publication Data

US 2018/0146666 A1 May 31, 2018

Related U.S. Application Data

(60) Provisional application No. 62/427,064, filed on Nov. 28, 2016.

(51) Int. Cl.
*A01N 37/34* (2006.01)
*C07C 311/13* (2006.01)
*A01N 41/06* (2006.01)

(52) U.S. Cl.
CPC ............ *A01N 37/34* (2013.01); *A01N 41/06* (2013.01); *C07C 311/13* (2013.01)

(58) Field of Classification Search
CPC .............................. A01N 41/06; C07C 311/13
See application file for complete search history.

(56) References Cited

U.S. PATENT DOCUMENTS

| | | | |
|---|---|---|---|
| 3,256,148 A | 6/1966 | Speziale et al. | |
| 3,498,780 A | 3/1970 | Soper et al. | |
| 4,071,350 A | 1/1978 | Arneklev et al. | |
| 4,209,530 A | 6/1980 | Visscher | |
| 5,173,106 A | 12/1992 | Kamuro et al. | |
| 5,625,130 A | 4/1997 | Grant et al. | |
| 6,586,617 B1 * | 7/2003 | Tabuchi | A01N 41/06 558/394 |
| 7,214,786 B2 | 5/2007 | Kovalic et al. | |
| 7,569,389 B2 | 8/2009 | Feldmann et al. | |
| 7,847,156 B2 | 12/2010 | Inze et al. | |
| 9,315,821 B2 | 4/2016 | Cutler et al. | |
| 2004/0148654 A1 | 7/2004 | Helentjaris | |
| 2004/0214272 A1 | 10/2004 | La Rosa et al. | |
| 2005/0244971 A1 | 11/2005 | Kim | |
| 2006/0021088 A1 | 1/2006 | Inze et al. | |
| 2006/0150283 A1 | 7/2006 | Alexandrov et al. | |
| 2006/0179518 A1 | 8/2006 | Hill et al. | |
| 2007/0039067 A1 | 2/2007 | Feldmann et al. | |
| 2009/0105238 A1 | 4/2009 | Filippini et al. | |
| 2009/0163545 A1 | 6/2009 | Goldfarb | |
| 2009/0320152 A1 | 12/2009 | Steber et al. | |
| 2010/0216643 A1 | 8/2010 | Cutler et al. | |
| 2011/0271408 A1 | 11/2011 | Cutler et al. | |
| 2013/0324409 A1 | 12/2013 | Cutler et al. | |
| 2014/0325701 A1 | 10/2014 | Cutler | |

FOREIGN PATENT DOCUMENTS

| | | |
|---|---|---|
| CN | 101173287 A | 5/2008 |
| JP | 2007 222129 A | 9/2007 |
| WO | 03/008540 A2 | 1/2003 |
| WO | 2004/035798 A2 | 4/2004 |
| WO | 2010/093954 A2 | 8/2010 |

OTHER PUBLICATIONS

Chen, Inês, "ABA receptor diversity," SBKB, Nov. 2010 featured articles, retrieved Jun. 2, 2014, 3 pages [doi:10.1038/sbkb.2010.49].
Chen, Peter, Plant Growth Regulatory Activities of Artemisinin and its Related Compounds, 1990, Journal of Chemical Ecology, vol. 16, No. 6, pp. 1867-1876.
Cutler et al., "Abscisic Acid: Emergence of a Core Signaling Network," Annu. Rev. Plant Biol., 2010, 61:651-679.
EMBL accession No. AY042890, Feb. 26, 2010.
Fujii et al., "In vitro reconstitution of an abscisic acid signaling pathway," Nature, vol. 462, Dec. 2009, p. 660, XP002676972.
GenBank as accession No. NP_563626, available online Jan. 28, 2002.
GenBank as accession No. NP_565887, available online Jan. 28, 2002.
GenBank accession No. 3OQU_A, "Chain A, Crystal Structure of Native Abscisic Acid Receptor Pyl9 With ABA", Jul. 31, 2013, pp. 1-2.
"GenBank accession No. NP_5636261", "abscisic acid receptor PYL9 [*Arabidopsis thaliana*]", May 26, 2011, pp. 1-2.
"GenBank accession No. 4JDL_A", "Chain A, Crystal Structure of Native Abscisic Acid Receptor Pyl5 At 2.65 Angstrom", Aug. 8, 2013, pp. 1-2.
Gonzalez-Guzman et al., "The Short-Chain Alcohol Dehydrogenase ABA2 Catalyzes the Conversion of Xanthoxin to Abscisic Aldehyde", The Plant Cell, Aug. 2002, 14(8):1833-1846.
Gonzalez-Guzman et al., "*Arabidopsis* PYR-PYL/RCAR receptors play a major role in quantitative regulation of stomatal aperture and transcriptional response to abscisic acid," The Plant Cell, 2012, vol. 24, pp. 2483-2496.
Hao et al., "The Molecular Basis of ABA-Independent Inhibition of PP2Cs by a Subclass of PYL Proteins", Molecular Cell, Jun. 10, 2011, 42(5):662-672.
Hauser et al., "Evolution of Abscisic Acid Synthesis and Signaling Mechanisms", Current Biology, May 10, 2011, 21(9):R346-R355.
Kim et al., "Chemoselective N-Benzenesulfonylation of Aliphatic Amines," Bull. Korean Chem. Soc. 2003, 24(11):1655-1658.

(Continued)

*Primary Examiner* — John Pak
(74) *Attorney, Agent, or Firm* — Kilpatrick Townsend & Stockton LLP

(57) ABSTRACT

The present invention provides agonist compounds that activate ABA receptors, agricultural formulations comprising the agonist compounds, and methods of use for the compounds and formulations. The agricultural formulations are useful for inducing ABA responses in plant vegetative tissues, reducing abiotic stress in plants, and inhibiting germination of plant seeds. The compounds are also useful for inducing expression of ABA-responsive genes in cells that express endogenous or heterologous ABA receptors.

21 Claims, 9 Drawing Sheets

Specification includes a Sequence Listing.

(56) References Cited

OTHER PUBLICATIONS

Kline et al., "Abscisic Acid Receptors," Plant Physiology, Oct. 2010, vol. 154, No. 2, pp. 479-482.
Koehergin, P.M., Imidazole Series. XII. Synthesis of esters and hydrazides of 2-imidazolylthioacetic acids, 1961, Zhurnal Obshchei Khimii, vol. 31, Abstract.
Lee, Sung Chul et al., "Functional roles of the pepper antimicrobial protein gene, CaAMP1, in abscisic acid signaling, and salt and drought tolerance in *Arabidopsis*," Planta (2009) 229:383-391.
Li et al., Science in China Ser. C Life Sciences, 2005, vol. 48, No. 2, pp. 181-186.
Masgrau et al.; "Inducible overexpression of oat arginine decarboxylase in transgenic tobacco plants"; 1997, The Plant Journal, vol. 11, No. 3, pp. 465-473.
Melcher et al., "A gate-latch-lock mechanism for hormone signaling by abscisic acid receptors," Nature (2009) 462:602-608.
Melcher et al., "Identification and mechanism of ABA receptor antagonism", Nature Structural & Molecular Biology. Nature Publishing Group. New York. NY. US, Sep. 1, 2010, 17(9):1102-1108.
Mosquna et al., Potent and selective activation of abscisic acid receptors in vivo mutational stabilization of their agonist-bound conformation, Proc. Natl. Acad. Sci. USA., vol. 108., No. 51, Dec. 2011, pp. 20838-20843, XP002676970.
Nishimura et al., "Structural Mechanism of Abscisic Acid Binding and Signaling by Dimeric PYR1," Science, Dec. 2009, 326(5958):1373-1379.
Park et al., "Abscisic acid inhibits type 2C protein phosphatases via the PYR/PYL family of START proteins," Science, vol. 324, May 2009, pp. 1068-1071, XP002676971.
Peterson et al., "Structural basis for selective activation of ABA receptors," Nat. Struct. Mol. Biol., 2010, 17(9):1109-1113.
Q84MC7, "Recommended name: Abscisic acid receptor PYL9; Alternative name(s): ABI1-binding protein 4, PYR1-like protein 9, Regulatory components of ABA receptor 1", http://www.uniprot.org/uniprot/Q84MC7, Jun. 1, 2003.
Santiago et al., "Modulation of drought resistance by the abscisic acid receptor PYL5 through inhibition of clade a PP2Cs," The Plant Journal (2009) 60:575-588.
Santiago et al., "The abscisic acid receptor PYR1 in complex with abscisic acid", Nature, Dec. 3, 2009, 462(7273):665-668.
Spencer et al., "Segregation of transgenes in maize," Plant Mol. Biol., 1992, vol. 18, pp. 201-210.
UniProtKP accession No. O49686, Mar. 2, 2010.
Wang et al., "Molecular tailoring of farnesylation for plant drought tolerance and yield protection," The Plant Journal (2005) 43:413-424.
Weiner et al., Current Opinion in Plant Biology, 2010, 13:495-502.
Williams et al.; "A possible role for kinase-associated protein phosphatase in the *Arabidopsis* CLAVATA1 signaling pathway"; 1997, Proc. Natl. Acad. Sci., vol. 94, pp. 10467-10472.
Xie et al., "Cloning, sequence analysis and prokaryotic expression of pathogenesis-induced protein (PIP) gene from peanut," Crops Research Institute, Guangdong Academy of Agricultural Sciences, China, Jan. 2009, XP002676969, Database accession No. 153:424228, abstract.
Zhang et al., "Structural basis and functions of abscisic acid receptors PYLs", Frontiers in Plant Science (2015) vol. 6., Article 88, pp. 1-16.
EP10741826.1, "Extended European Search Report", dated Jul. 2, 2012, 14 pages.
PCT/US2010/024139, "International Search Report and Written Opinion", dated Dec. 15, 2010, 12 pages.
PCT/US2010/024139, "International Preliminary Report on Patentability", dated Aug. 25, 2011, 7 pages.

\* cited by examiner

| | $K_d$ (μM) | ΔH (kcal/mol) | ΔS (cal/mol.K) |
|---|---|---|---|
| PYR1 CB | 3.4 ± 0.5 | -2.0 ± 0.3 | 18.3 ± 0.9 |

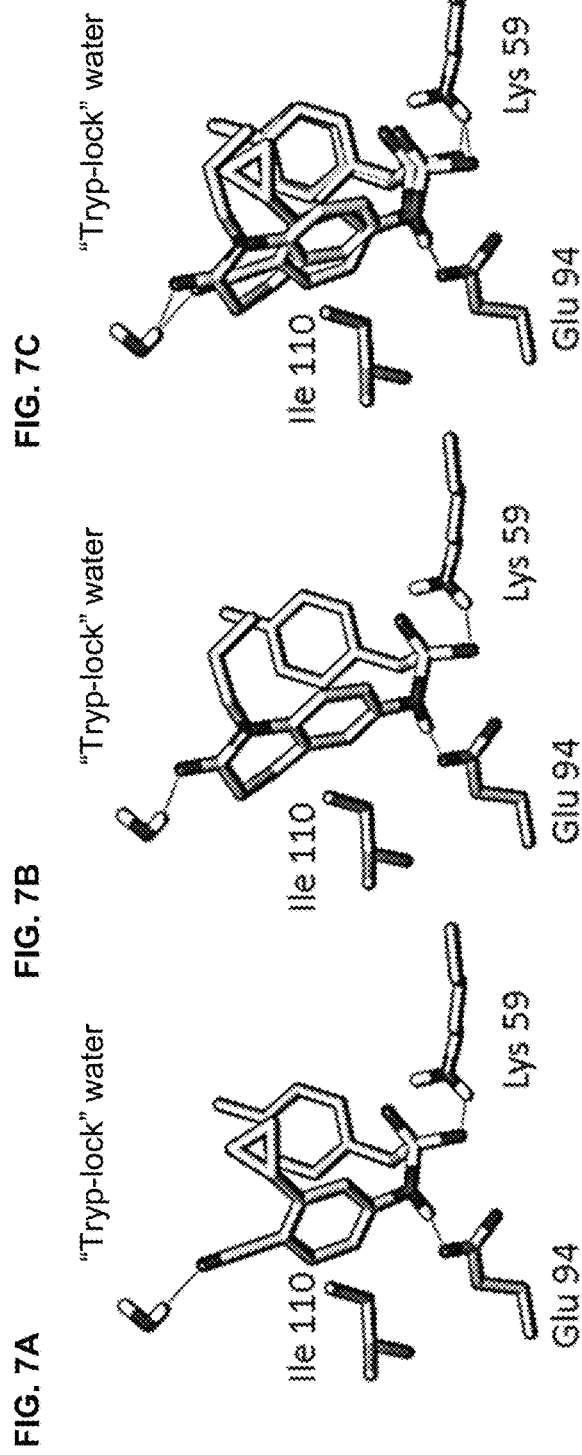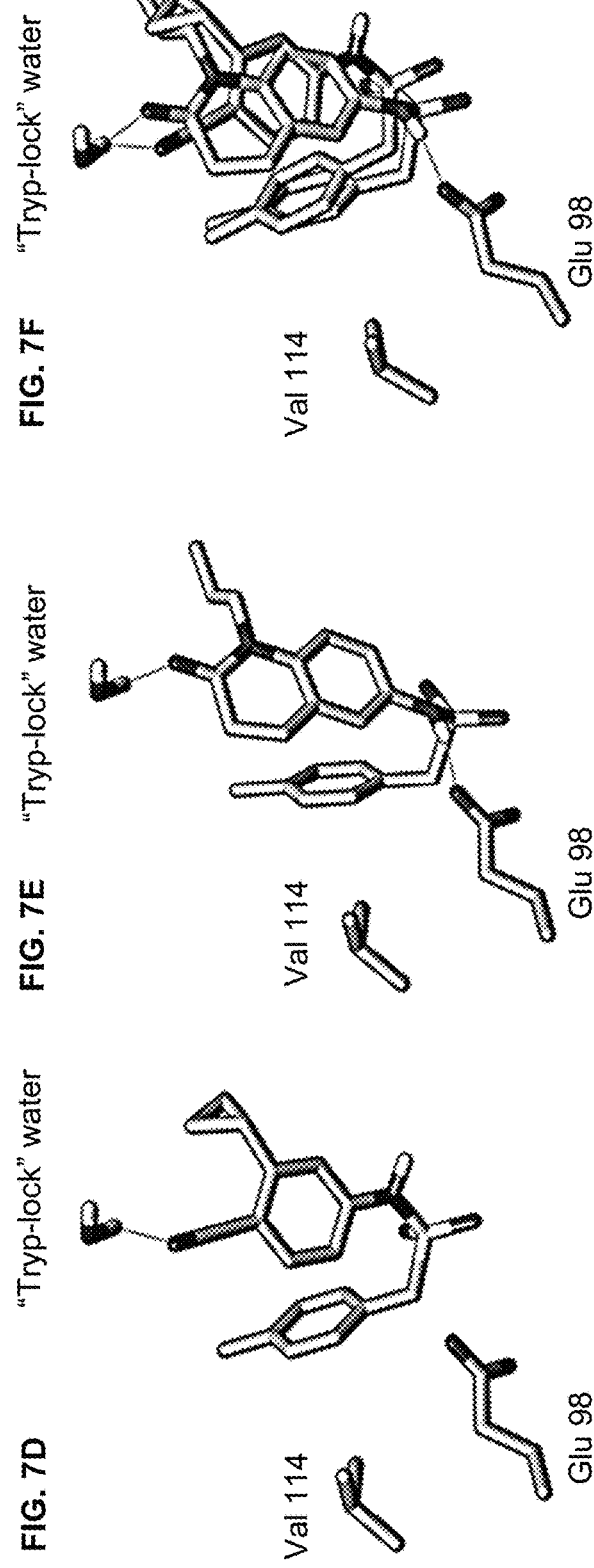

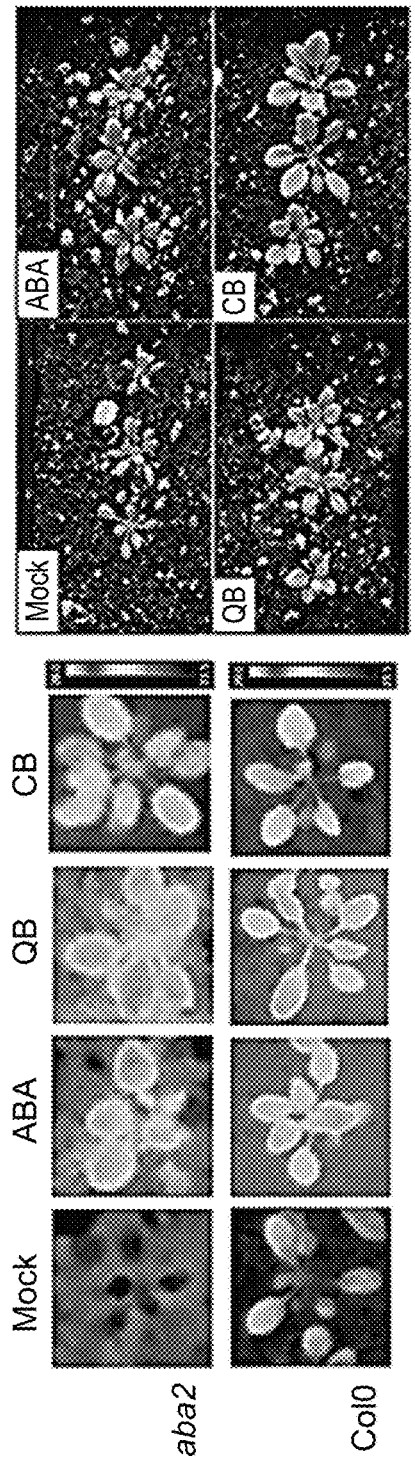
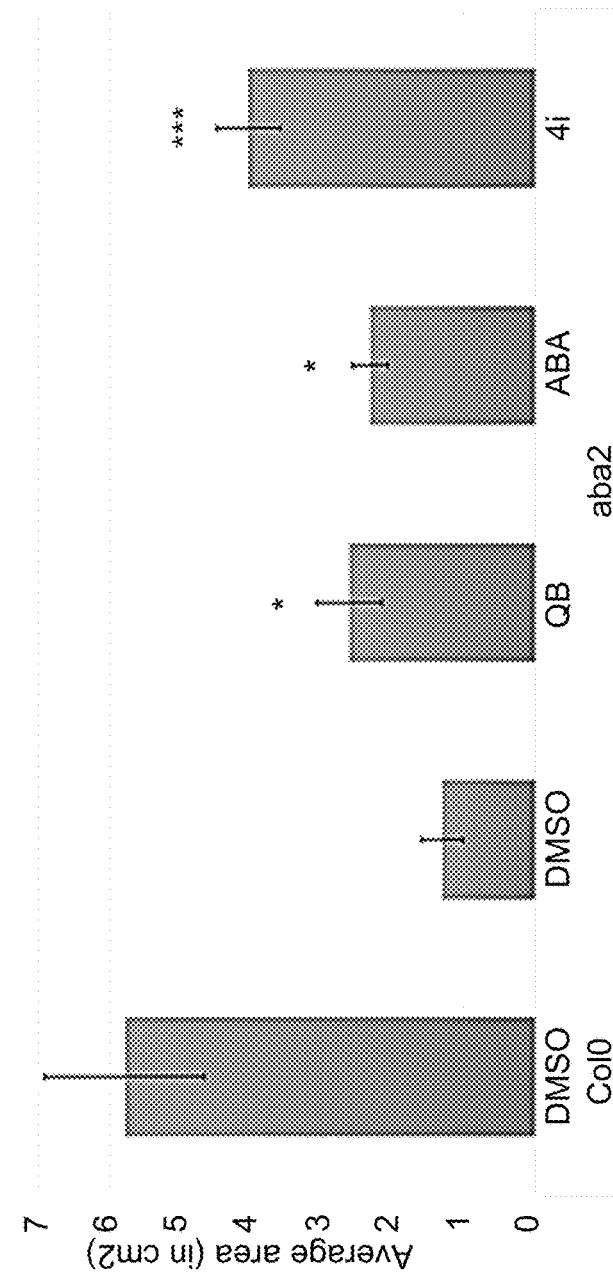
FIG. 8A
FIG. 8B
FIG. 8C

ABA RECEPTOR AGONISTS THAT MODULATE TRANSPIRATION

CROSS-REFERENCE TO RELATED APPLICATIONS

The present patent application claims the benefit of U.S. Provisional Patent Application No. 62/427,064, filed Nov. 28, 2016, the contents of which are incorporated by reference herein for all purposes.

REFERENCE TO A "SEQUENCE LISTING," A TABLE, OR A COMPUTER PROGRAM LISTING APPENDIX SUBMITTED ON A COMPACT DISK

This application includes a Sequence Listing as a text file "081906-1068920-222610US-SEQLIST.txt," machine format IBM-PC, MS-Windows operating system, created Nov. 28, 2017, and containing 225,414 bytes. The material contained in this text file is incorporated by reference in its entirety for all purposes.

BACKGROUND OF THE INVENTION

Abscisic acid (ABA) is a plant hormone that regulates signal transduction associated with abiotic stress responses (Cutler et al., 2010, Abscisic Acid: Emergence of a Core Signaling Network, Annual Review of Plant Biology 61:651-679). The ABA signaling pathway has been exploited to improve plant stress response and associated yield traits via numerous approaches (Yang et al., 2010, "Narrowing Down the Targets: Towards Successful Genetic Engineering of Drought-Tolerant Crops", *Mol. Plant*, 3(3): 469-490). The direct application of ABA to plants improves their water use efficiency (Rademacher et al., 1987, "Water consumption and yield formation in crop plants under the influence of synthetic analogues of abscisic acid," in: Hawkins et al. (ed.) "Plant growth regulators for agricultural and amenity use," BCPC Monograph 36:53-66); for this reason, the discovery of ABA receptor agonists (Park et al., "Abscisic Acid Inhibits Type 2C Protein Phosphatases via the PYR/PYL Family of START Proteins," *Science*, vol. 324, no. 5930, pp. 1068-1071 (2009); Melcher et al., 2010, "Identification and mechanism of ABA receptor antagonism," Nature Structural & Molecular Biology 17(9): 1102-1110) has received increasing attention, as such molecules may be beneficial for improving crop yield (Notman, "Organic compound comes to the aid of thirsty plants", Royal Society of Chemistry at http://www.rsc.org/chemistryworld/News/2009/May/01050901.asp (May 1, 2009; downloaded on Jun. 29, 2015)).

The first synthetic ABA receptor agonist identified was pyrabactin (Park et al., op. cit.), a naphthalene sulfonamide that efficiently activates ABA signaling in seeds, but has limited activity in vegetative tissues, where the most critical aspects of abiotic stress tolerance occur. Sulfonamides highly similar to pyrabactin have been disclosed as ABA receptor agonists (see U.S. Pat. App. Pub. No. 2013/0045952) and abiotic stress modulating compounds (see U.S. Pat. App. Pub. No. 2011/0230350). Non-sulfonamide ABA receptor agonists have also been described (see U.S. Pat. App. Pub. Nos. 2013/0045952 and 2011/0271408). A complementary approach to activating the ABA pathway involves increasing a plant's sensitivity to ABA via genetic methods. For example, conditional antisense of farnesyl transferase beta subunit gene, which increases a plant's ABA sensitivity, improves yield under moderate drought in both canola and *Arabidopsis* (Wang et al., 2005, "Molecular tailoring of farnesylation for plant drought tolerance and yield protection", *The Plant Journal* 43(3):413-424). Thus, the manipulation of ABA signaling to improve traits contributing to yield is now well established.

It has recently been discovered that ABA elicits many of its cellular responses by binding to a soluble family of receptors called PYR/PYL proteins. PYR/PYL proteins belong to a large family of ligand-binding proteins named the START superfamily (Iyer et al., 2001, "Adaptations of the helix-grip fold for ligand binding and catalysis in the START domain superfamily," Proteins: Structure, Function, and Bioinformatics 43(2):134-144); Ponting et al., 1999, "START: a lipid-binding domain in StAR, HD-ZIP and signalling proteins," *Trends Biochem,* 24(4):130-132). These proteins contain a conserved three-dimensional architecture consisting of seven anti-parallel beta sheets, which surround a central alpha helix to form a "helix-grip" motif; together, these structural elements form a ligand-binding pocket for binding ABA or other agonists.

BRIEF SUMMARY OF THE INVENTION

The present invention provides for small molecule ABA receptor agonists, i.e., compounds that activate PYR/PYL proteins. In some aspects, the present invention provides for agricultural formulations and methods comprising the ABA receptor agonists described herein.

In some aspects, the invention presents an agricultural formulation, comprising a compound of Formula I:

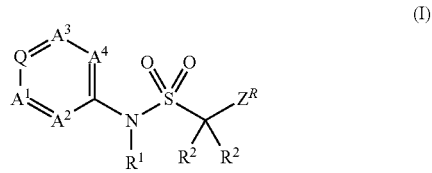

(I)

wherein
  $R^1$ is hydrogen;
  $R^2$ is selected from hydrogen, fluoro, cyclopropyl, and $R^6$;
  Q is $C(R^3)$;
  $A^1$ and $A^3$ are independently selected from N, C(H), and $C(R^4)$, wherein at least one member selected from $A^1$ and $A^3$ is $C(R^4)$;
  $A^2$ and $A^4$ are independently selected from N and $C(R^5)$; wherein at most two members selected from $A^1, A^2, A^3,$ and $A^4$ are N;
  $R^3$ is cyano;
  each $R^4$ is independently selected from halo, $C_{1-3}$ alkyl, $C_{1-3}$ haloalkyl, cyclopropyl, $-OR^6$, $-SR^6$, and $-N(R^6)_2$;
  each $R^5$ is selected from hydrogen, halo, $C_{1-3}$ alkyl, $C_{1-3}$ haloalkyl, $C_{3-7}$ cycloalkyl, $C_{1-6}$ hydroxyalkyl, nitro, $-OR^1, -SR^1,$ and $-N(R^1)_2$;
  each $R^6$ is independently selected from $C_{1-2}$ alkyl, $C_{1-2}$ haloalkyl, $C_{2-3}$ alkenyl, and $C_{2-3}$ alkynyl;
  $Z^R$ is a second ring that is selected from phenyl, naphthyl, pyridyl, pyrazinyl, pyrimidinyl, pyridazinyl, pyrrolyl, pyrazolyl, thiophenyl, and thiazolyl; wherein the second ring has from 0 to 5 $R^5$ substituents;
  or a salt or isomer thereof.

In some preferred embodiments, the compound of Formula I is a compound of Formula II:

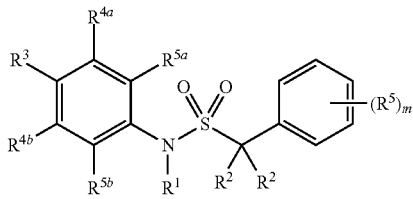

(II)

wherein
$R^{4a}$ and $R^{4b}$ are each independently selected from hydrogen, halo, $C_{1-3}$ alkyl, $C_{1-3}$ haloalkyl, and cyclopropyl; wherein at least one of the $R^{4a}$ and the $R^{4b}$ is not hydrogen;
$R^{5a}$ and $R^{5b}$ are each independently selected from hydrogen, halo, methyl, ethyl, trifluoromethyl, nitro, methoxy, ethoxy, and amino;
m is an integer from 0 to 4;
or a salt or isomer thereof.

In some preferred embodiments, the compound of Formula I is a compound of Formula III:

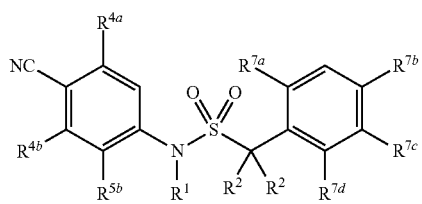

(III)

wherein
$R^{7a}$, $R^{7b}$, $R^{7c}$, and $R^{7d}$ are each independently selected from the group consisting of hydrogen, halo, $C_{1-3}$ alkyl, trifluoromethyl, nitro, —$OR^1$, and —$N(R^1)_2$;
or a salt or isomer thereof.

In some aspects, the invention presents a method of increasing drought tolerance in a plant, the method comprising contacting a plant with a sufficient amount of the agricultural formulation as otherwise disclosed herein, thereby increasing drought tolerance in the plant compared to not contacting the plant with the formulation.

In some aspects, the invention presents a method of bringing a plant in contact with the agricultural formulation as otherwise disclosed herein, comprising contacting the plant with the agricultural formulation.

In some aspects, the invention presents a method of activating a PYR/PYL protein, the method comprising contacting the PYR/PYL protein with a compound of Formula I, II, or III as disclosed herein.

Further aspects, objects, and advantages of the invention will become apparent upon consideration of the detailed description and figures that follow.

In some embodiments, the agricultural formulation further comprises an agricultural chemical that is useful for promoting plant growth, reducing weeds, or reducing pests. In some embodiments, the agricultural formulation further comprises at least one of a fungicide, an herbicide, a pesticide, a nematicide, an insecticide, a plant activator, a synergist, an herbicide safener, a plant growth regulator, an insect repellant, an acaricide, a molluscicide, or a fertilizer.

In some embodiments, the agricultural formulation further comprises a surfactant. In some embodiments, the agricultural formulation further comprises a carrier.

In some aspects, the invention provides methods for increasing abiotic stress tolerance in a plant, the method comprising the step of contacting a plant with a sufficient amount of the above formulations to increase abiotic stress tolerance in the plant compared to the abiotic stress tolerance in the plant when not contacted with the formulation. In some embodiments, the plant is a monocot. In some embodiments, the plant is a dicot. In some embodiments, the abiotic stress tolerance comprises drought tolerance.

In some aspects, the invention provides a method of inhibiting seed germination in a plant, the method comprising the step of contacting a plant, a plant part, or a plant seed with a sufficient amount of the above formulations to inhibit germination.

In some aspects, the invention provides a plant or plant part in contact with the above formulations. In some embodiments, the plant or plant part is a seed.

In some aspects, the invention provides a method of activating a PYR/PYL protein. In some embodiments, the PYR/PYL protein binds a type 2 protein phosphatase (PP2C) polypeptide when the PYR/PYL protein binds the agonist compound quinabactin. In some embodiments, the method comprises the step of contacting the PYR/PYL protein with any of the compounds described herein.

Further aspects, objects, and advantages of the invention will become apparent upon consideration of the detailed description and figures that follow.

BRIEF DESCRIPTION OF THE DRAWINGS

FIGS. 7A, 7B, and 7C show the calculated interactions of Q27 in PYR1 (Example 8). FIGS. 7D, 7E, and 7F show the calculated interactions of Q27 in PYL2 (Example 8).

FIG. 8A and FIG. 8C show the effects of Q27, ABA, and quinabactin in thermal response assays in an ABA-deficient aba2 mutant (Example 9). FIG. 8B shows the effects of Q27, ABA, and quinabactin in a growth complementation assay (Example 9).

DETAILED DESCRIPTION OF THE INVENTION

I. Definitions

Figure 1A:
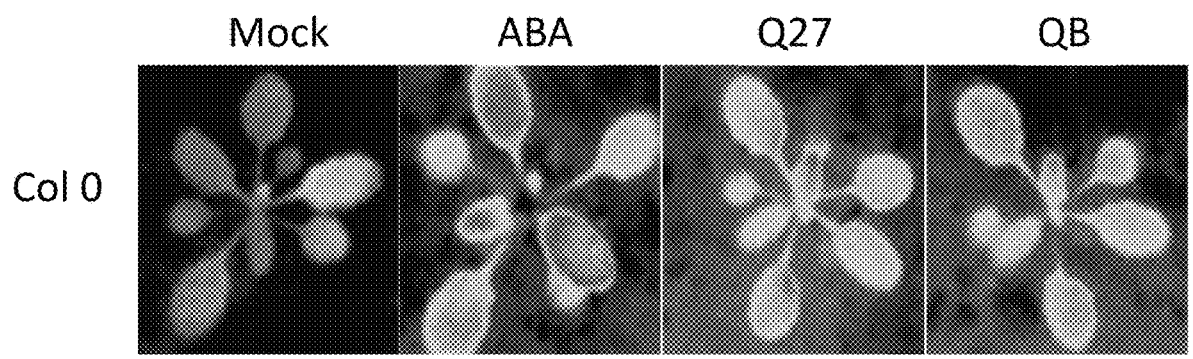
FIG. 1A and FIG. 1B show the thermal response after 24 h elicited in adult plants by an inventive compound sprayed at 50 uM or by a solvent carrier control (Example 3).

"Agonists" are agents that, e.g., induce or activate the expression of a described target protein or bind to, stimulate, increase, open, activate, facilitate, enhance activation, sensitize or up-regulate the activity of one or more plant PYR/PYL proteins (or encoding polynucleotide). Agonists can include naturally occurring and synthetic molecules. In some embodiments, the agonists are combined with agrichemicals to produce and agricultural formulation. Examples of suitable agrichemicals include fungicides, herbicides, pesticides, fertilizers, or surfactants. Assays for determining whether an agonist "agonizes" or "does not agonize" a PYR/PYL protein include, e.g., contacting putative agonists to purified PYR/PYL protein(s) and then determining the functional effects on the PYR/PYL protein activity, as described herein, or contacting putative agonists to cells expressing PYR/PYL protein(s) and then determining the functional effects on the described target protein activity, as described herein. One of skill in the art will be able to determine whether an assay is suitable for determining whether an agonist agonizes or does not agonize a PYR/PYL protein. Samples or assays comprising PYR/PYL proteins that are treated with a putative agonist are compared to control samples without the agonist to examine the extent of effect. Control samples (untreated with agonists) are assigned a relative activity value of 100%. Agonism of the PYR/PYL protein is achieved when the activity value relative to the control is 110%, optionally 150%, optionally 200, 300%, 400%, 500%, or 1000-3000% or more higher.

The term "PYR/PYL receptor polypeptide" refers to a protein characterized in part by the presence of one or more or all of a polyketide cyclase domain 2 (PF10604), a polyketide cyclase domain 1 (PF03364), and a Bet V I domain (PF03364), which in wild-type form mediates abscisic acid (ABA) and ABA analog signaling. A wide variety of PYR/PYL receptor polypeptide sequences are known in the art. In some embodiments, a PYR/PYL receptor polypeptide comprises a polypeptide that is substantially identical to any one of SEQ ID NOs: 1-119. See, e.g., Int. Pat. Pub. No. WO 2011/139798 (U.S. Pat. App. Pub. No. US 2011/0271408).

The term "activity assay" refers to any assay that measures or detects the activity of a PYR/PYL receptor polypeptide. An exemplary assay to measure PYR/PYL receptor activity is a yeast two-hybrid assay that detects binding of a PYR/PYL polypeptide to a type 2 protein phosphatase (PP2C) polypeptide, as described in the Examples.

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11-17 (1988) e.g., as implemented in the program PC/GENE (Intelligenetics, Mountain View, Calif., USA).

The phrase "substantially identical," used in the context of two nucleic acids or polypeptides, refers to a sequence that has at least 60% sequence identity with a reference sequence. Alternatively, percent identity can be any integer from 60% to 100%. Some embodiments include at least: 60%, 65%, 70%, 75%, 80%, 85%, 90%, 91%, 92%, 93%, 94% 95%, 96%, 97%, 98%, or 99%, compared to a reference sequence using the programs described herein; preferably BLAST using standard parameters, as described below. Embodiments of the present invention provide for polypeptides, and nucleic acids encoding polypeptides, that are substantially identical to any of SEQ ID NO: 1-119.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci.* USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

Algorithms that are suitable for determining percent sequence identity and sequence similarity are the BLAST and BLAST 2.0 algorithms, which are described in Altschul et al. (1990) *J. Mol. Biol.* 215: 403-410 and Altschul et al. (1977) *Nucleic Acids Res.* 25: 3389-3402, respectively. Software for performing BLAST analyses is publicly available through the National Center for Biotechnology Information (NCBI) web site. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, *Proc. Natl. Acad. Sci. USA* 89:10915 (1989)).

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.01, more preferably less than about $10^{-5}$, and most preferably less than about $10^{-20}$.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, in a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).
(see, e.g., Creighton, *Proteins* (1984)).

The term "plant" includes whole plants, shoot vegetative organs or structures (e.g., leaves, stems and tubers), roots, flowers and floral organs (e.g., bracts, sepals, petals, stamens, carpels, anthers), ovules (including egg and central cells), seed (including zygote, embryo, endosperm, and seed coat), fruit (e.g., the mature ovary), seedlings, plant tissue (e.g., vascular tissue, ground tissue, and the like), cells (e.g., guard cells, egg cells, trichomes and the like), and progeny of same. The class of plants that can be used in the methods of the invention includes angiosperms (monocotyledonous and dicotyledonous plants), gymnosperms, ferns, bryophytes, and multicellular and unicellular algae. It includes plants of a variety of ploidy levels, including aneuploid, polyploid, diploid, haploid, and hemizygous.

As used herein, the term "transgenic" describes a non-naturally occurring plant that contains a genome modified by man, wherein the plant includes in its genome an exogenous nucleic acid molecule, which can be derived from the same or a different plant species. The exogenous nucleic acid molecule can be a gene regulatory element such as a promoter, enhancer, or other regulatory element, or can contain a coding sequence, which can be linked to a heterologous gene regulatory element. Transgenic plants that arise from sexual cross or by selfing are descendants of such a plant and are also considered "transgenic.".

As used herein, the term "drought-resistance" or "drought-tolerance," including any of their variations, refers to the ability of a plant to recover from periods of drought stress (i.e., little or no water for a period of days). Typically, the drought stress will be at least 5 days and can be as long as, for example, 18 to 20 days or more (e.g., at least 6, 7, 8, 9, 10, 11, 12, 13, 14, 15, 16, 17, 18, 19, 20 days), depending on, for example, the plant species.

As used herein, the terms "abiotic stress," "stress," or "stress condition" refer to the exposure of a plant, plant cell, or the like, to a non-living ("abiotic") physical or chemical agent that has an adverse effect on metabolism, growth, development, propagation, or survival of the plant (collectively, "growth"). A stress can be imposed on a plant due, for example, to an environmental factor such as water (e.g., flooding, drought, or dehydration), anaerobic conditions (e.g., a lower level of oxygen or high level of $CO_2$), abnormal osmotic conditions, salinity, or temperature (e.g., hot/heat, cold, freezing, or frost), a deficiency of nutrients or exposure to pollutants, or by a hormone, second messenger, or other molecule. Anaerobic stress, for example, is due to a reduction in oxygen levels (hypoxia or anoxia) sufficient to produce a stress response. A flooding stress can be due to prolonged or transient immersion of a plant, plant part, tissue, or isolated cell in a liquid medium such as occurs during monsoon, wet season, flash flooding, or excessive irrigation of plants, or the like. A cold stress or heat stress can occur due to a decrease or increase, respectively, in the temperature from the optimum range of growth temperatures for a particular plant species. Such optimum growth temperature ranges are readily determined or known to those skilled in the art. Dehydration stress can be induced by the loss of water, reduced turgor, or reduced water content of a cell, tissue, organ or whole plant. Drought stress can be induced by or associated with the deprivation of water or reduced supply of water to a cell, tissue, organ or organism. Salinity-induced stress (salt-stress) can be associated with or induced by a perturbation in the osmotic potential of the intracellular or extracellular environment of a cell. As used herein, the term "abiotic stress tolerance" or "stress tolerance" refers to a plant's increased resistance or tolerance to abiotic stress as compared to plants under normal conditions and the ability to perform in a relatively superior manner when under abiotic stress conditions.

A polypeptide sequence is "heterologous" to an organism or a second polypeptide sequence if it originates from a foreign species, or, if from the same species, is modified from its original form.

The terms "a," "an," or "the" as used herein not only include aspects with one member, but also (unless specified otherwise) include aspects with more than one member. For example, an embodiment of a method of imaging that comprises using a compound set forth in claim 1 would include an aspect in which the method comprises using two or more compounds set forth in claim 1.

"Alkenyl" as used herein includes a straight or branched aliphatic hydrocarbon group of 2 to about 15 carbon atoms that contains at least one carbon-carbon double bond. Preferred alkenyl groups have 2 to about 6 carbon atoms. More preferred alkenyl groups contain 2 to about 3 carbon atoms. "Lower alkenyl" as used herein includes alkenyl of 2 to about 6 carbon atoms. Representative alkenyl groups include vinyl, allyl, n-butenyl, 2-butenyl, 3-methylbutenyl, n-pentenyl, and the like.

"Alkoxy" as used herein includes an alkyl-O— group wherein the alkyl group is as defined herein. Representative alkoxy groups include methoxy, ethoxy, n-propoxy, i-propoxy, n-butoxy, heptoxy, and the like.

"Alkyl" as used herein includes an aliphatic hydrocarbon group, which may be straight or branched-chain, having about 1 to about 20 carbon atoms in the chain. Preferred alkyl groups have 1 to 8, 1 to 6, 1 to 4, or 1 to 3 carbon atoms in the chain. "Branched-chain" as used herein includes groups in which one or more lower alkyl groups such as methyl, ethyl or propyl are attached to a linear alkyl chain (e.g., 2-methyl-3-pentyl). "Lower alkyl" as used herein includes 1 to about 6 carbon atoms in the chain, which may be straight or branched (e.g., methyl, ethyl, n-propyl, iso-propyl, n-butyl, 2-butyl, t-butyl, n-pentyl, 2-pentyl, 3-pentyl, 2-methyl-2-butyl, and the like). Representative alkyl groups include methyl, ethyl, n-propyl, isopropyl, n-butyl, t-butyl, n-pentyl, and 3-pentyl.

"Alkylthio" as used herein includes an alkyl-S— group wherein the alkyl group is as defined herein. Preferred alkylthio groups are those wherein the alkyl group is lower alkyl. Representative alkylthio groups include methylthio, ethylthio, isopropylthio, heptylthio, and the like.

"Alkynyl" as used herein includes a straight or branched aliphatic hydrocarbon group of 2 to about 15 carbon atoms that contains at least one carbon-carbon triple bond. Preferred alkynyl groups have 2 to about 12 carbon atoms. More preferred alkynyl groups contain 2 to about 6 carbon atoms. "Lower alkynyl" as used herein includes alkynyl of 2 to about 6 carbon atoms. Representative alkynyl groups include propynyl, 2-butynyl, 3-methylbutynyl, n-pentynyl, heptynyl, and the like.

"Amino" as used herein includes a group of formula $Y_1Y_2N$— wherein $Y_1$ and $Y_2$ are independently hydrogen, acyl, aryl, or alkyl; or $Y_1$ and $Y_2$, together with the nitrogen through which $Y_1$ and $Y_2$ are linked, join to form a 4- to 7-membered azaheterocyclyl group (e.g., piperidinyl). Optionally, when $Y_1$ and $Y_2$ are independently hydrogen or alkyl, an additional substituent can be added to the nitrogen, making a quaternary ammonium ion. Representative amino groups include primary amino ($H_2N$—), methylamino, dimethylamino, diethylamino, tritylamino, and the like. Preferably, "amino" is an —NRR' group where R and R' are members independently selected from the group consisting of H and alkyl. Preferably, at least one of R and R' is H.

"Comprises" as used herein is not closed—that is, it does not limit a composition to include only the expressly disclosed components. For example, "a composition comprising A and B" could be a composition containing only A and B; a composition containing A, B, and C; a composition containing A, B, C, and D; and the like.

"Cycloalkyl" as used herein includes a non-aromatic mono- or multicyclic ring system of about 3 to about 10 carbon atoms, preferably of about 3 to about 5 carbon atoms. More preferred cycloalkyl rings include cyclopropyl. A cycloalkyl group optionally comprises at least one $sp^2$-hybridized carbon (e.g., a ring incorporating an endocyclic or exocyclic olefin). Representative monocyclic cycloalkyl groups include cyclopentyl, cyclohexyl, cyclohexenyl, cycloheptyl, and the like. Representative multicyclic cycloalkyl include 1-decalin, norbornyl, adamantyl, and the like.

"Halo" or "halogen" as used herein includes fluoro, chloro, bromo, or iodo. A preferred halogen is fluoro.

"Haloalkyl" as used herein includes an alkyl group wherein the alkyl group includes one or more halo- substituents. For example, "fluoroalkyl" is an alkyl group wherein the alkyl group includes fluoro- substituents (e.g., trifluoromethyl).

When any two substituent groups or any two instances of the same substituent group are "independently selected" from a list of alternatives, they may be the same or different. For example, if $R^a$ and $R^b$ are independently selected from the group consisting of methyl, hydroxymethyl, ethyl, hydroxyethyl, and propyl, then a molecule with two $R^a$ groups and two $R^b$ groups could have all groups be methyl. Alternatively, the first $R^a$ could be methyl, the second $R^a$ could be ethyl, the first $R^b$ could be propyl, and the second $R^b$ could be hydroxymethyl (or any other substituents taken from the group). Alternatively, both $R^a$ and the first $R^b$ could be ethyl, while the second $R^b$ could be hydroxymethyl (i.e., some pairs of substituent groups may be the same, while other pairs may be different).

The prefixes "u" and "µ" are used herein interchangeably to denote "micro." For example, "uM" and "µM" are used interchangeably denote "micromolar."

The present invention is based, in part, on the discovery of selective abscisic acid (ABA) agonists. Unlike previous ABA receptor agonists, the agonists described herein potently activate the ABA pathway in plant vegetative tissues and induce abiotic stress tolerance. The new agonists can be used to induce stress tolerance in crop species of plants. The agonists can be used to induce stress tolerance in monocot and dicot plant species, including but not limited to broccoli, radish, alfalfa, soybean, barley, and corn (maize).

Abscisic acid is a multifunctional phytohormone involved in a variety of phyto-protective functions including bud dormancy, seed dormancy or maturation, abscission of leaves and fruits, and response to a wide variety of biological stresses (e.g. cold, heat, salinity, and drought). ABA is also responsible for regulating stomatal closure by a mechanism independent of $CO_2$ concentration. The PYR/PYL family of ABA receptor proteins mediate ABA signaling. Plants examined to date express more than one PYR/PYL receptor protein family member, which have at least somewhat redundant activity. PYR/PYL receptor proteins mediate ABA signaling as a positive regulator in, for example, seed germination, post-germination growth, stomatal movement and plant tolerance to stress including, but not limited to, drought.

A wide variety of wild-type (naturally occurring) PYR/PYL polypeptide sequences are known in the art. Although PYR1 was originally identified as an abscisic acid (ABA) receptor in *Arabidopsis*, in fact PYR1 is a member of a group of at least 14 proteins (PYR/PYL proteins) in the same protein family in *Arabidopsis* that also mediate ABA signaling. This protein family is also present in other plants (see, e.g., SEQUENCE LISTING) and is characterized in part by the presence of one or more or all of a polyketide cyclase domain 2 (PF10604), a polyketide cyclase domain 1 (PF03364), and a Bet V I domain (PF03364). START/Bet v 1 superfamily domain are described in, for example, Radauer, *BMC Evol. Biol.* 8:286 (2008). In some embodiments of the methods described, a wild-type PYR/PYL receptor polypeptide comprises any of SEQ ID NOs: 1-119. In some embodiments, a wild-type PYR/PYL receptor polypeptide is substantially identical to (e.g., at least 70%, 75%, 80%, 85%, 90%, 91%, 92%, 93%, 94% 95%, 96%, 97%, 98%, or 99% identical to) any of SEQ ID NOs: 1-119. In some embodiments, a PYR/PYL receptor polypeptide is substantially identical to (e.g., at least 70%, 75%, 80%, 85%, 90%, 91%, 92%, 93%, 94% 95%, 96%, 97%, 98%, or 99% identical to) any of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, or 119.

II. ABA Receptor Agonists

The present invention sets forth small-molecule ABA receptor agonists, i.e., compounds that activate PYR/PYL proteins. In some aspects, the present invention provides for agricultural formulations and methods comprising the ABA receptor agonists described herein.

In some aspects, the invention presents an agricultural formulation, comprising a compound of Formula I:

(I)

wherein
$R^1$ is hydrogen;
$R^2$ is selected from hydrogen, fluoro, cyclopropyl, and $R^6$;
Q is $C(R^3)$;
$A^1$ and $A^3$ are independently selected from N, C(H), and $C(R^4)$, wherein at least one member selected from $A^1$ and $A^3$ is $C(R^4)$;

$A^2$ and $A^4$ are independently selected from N and $C(R^5)$; wherein at most two members selected from $A^1$, $A^2$, $A^3$, and $A^4$ are N;
$R^3$ is cyano;
each $R^4$ is independently selected from halo, $C_{1-3}$ alkyl, $C_{1-3}$ haloalkyl, cyclopropyl, —$OR^6$, —$SR^6$, and —$N(R^6)_2$;
each $R^5$ is selected from hydrogen, halo, $C_{1-3}$ alkyl, $C_{1-3}$ haloalkyl, $C_{3-7}$ cycloalkyl, $C_{1-6}$ hydroxyalkyl, nitro, —$OR^1$, —$SR^1$, and —$N(R^1)_2$;
each $R^6$ is independently selected from $C_{1-2}$ alkyl, $C_{1-2}$ haloalkyl, $C_{2-3}$ alkenyl, and $C_{2-3}$ alkynyl;
$Z^R$ is a second ring that is selected from phenyl, naphthyl, pyridyl, pyrazinyl, pyrimidinyl, pyridazinyl, pyrrolyl, pyrazolyl, thiophenyl, and thiazolyl; wherein the second ring has from 0 to 5 $R^5$ substituents;
or a salt or isomer thereof.

In some preferred embodiments, $R^1$ is hydrogen. Without intending to be limited by theory, the sulfonamide may form a hydrogen bond with N173 of PYL2.

In some embodiments, $R^2$ is selected from hydrogen, fluoro, and $R^6$. In some embodiments, $R^2$ is selected from hydrogen, fluoro, cycloalkyl, and $R^6$. In some embodiments, $R^2$ is selected from hydrogen, fluoro, cyclopropyl, and $R^6$. In some embodiments, $R^2$ is hydrogen, fluoro, $C_{1-2}$ alkyl, or $C_{1-2}$ fluoroalkyl. In some embodiments, $R^2$ is hydrogen, methyl, or trifluoromethyl. In some preferred embodiments, $R^2$ is hydrogen.

In some embodiments, $A^1$ is N. In some embodiments, $A^2$ is N. In some embodiments, $A^3$ is N. In some embodiments, $A^4$ is N. In some preferred embodiments, at most one member selected from $A^1$, $A^2$, $A^3$, and $A^4$ is N. In some preferred embodiments, no members are N. In some preferred embodiments, at most one member of the group consisting of $A^1$ and $A^3$ is N.

In some preferred embodiments, $R^3$ is a hydrogen bond acceptor, preferably —CN. Without intending to be limited by theory, the crystal structure of ABA with PYL2 suggests that positioning a hydrogen bond acceptor near the loop subdomain comprising Trp-385 is important for agonist potency. The crystal structure of quinabactin with PYL2 also suggests that the oxygen in quinabactin's dihydroquinolinone ring forms an important hydrogen bond in a "Tryp lock" hydrogen bond network formed by a water molecule, residues P92, R120 in PYL2, and W385 in HAB1. In some preferred embodiments of the present invention, a nitrile para to the sulfonamide (i.e., at $R^3$) can coordinate with the loop subdomain. In some embodiments, the present invention sets forth a method of coordinating a hydrogen-bond acceptor with the PYR/PYL loop subdomain by administering a composition of Formula I.

In some embodiments, $R^4$ is independently selected from halo, $C_{1-3}$ alkyl, $C_{1-3}$ haloalkyl, cyclopropyl, —$OR^6$, —$SR^6$, and —$N(R^6)_2$. In some embodiments, $R^4$ is independently selected from $C_{1-3}$ alkyl, cyclopropyl, —$OR^6$, and —$N(R^6)_2$. In some embodiments, $R^4$ is independently selected from $C_{1-3}$ alkyl, cyclopropyl, and —$OR^6$. In some embodiments, $R^4$ is independently selected from methyl, ethyl, isopropyl, propyl, cyclopropyl, and —$OR^6$, wherein $R^6$ is $C_{1-3}$ alkyl. In some preferred embodiments, $R^4$ is independently selected from methyl, ethyl, propyl, methoxy, and ethoxy. In some preferred embodiments, $R^4$ is independently selected from methyl and methoxy. In some preferred embodiments, $R^4$ is methyl.

In some embodiments, $Z^R$ is naphthyl. In some embodiments, $Z^R$ is pyridyl. In some embodiments, $Z^R$ is pyrazinyl. In some embodiments, $Z^R$ is pyrimidinyl. In some embodiments, $Z^R$ is pyridazinyl. In some embodiments, $Z^R$ is pyrrolyl. In some embodiments, $Z^R$ is pyrazolyl. In some embodiments, $Z^R$ is thiophenyl. In some embodiments, $Z^R$ is thiazolyl. In some embodiments, $Z^R$ is selected from phenyl, naphthyl, and pyridyl. In some preferred embodiments, $Z^R$ is phenyl.

In some preferred embodiments, the compound is a compound of Formula II:

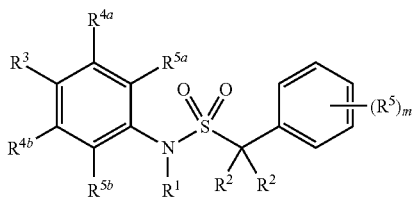

(II)

wherein
$R^{4a}$ and $R^{4b}$ are each independently selected from hydrogen, halo, $C_{1-3}$ alkyl, $C_{1-3}$ haloalkyl, and cyclopropyl; wherein at least one of the $R^{4a}$ and the $R^{4b}$ is not hydrogen;
$R^{5a}$ and $R^{5b}$ are each independently selected from hydrogen, halo, methyl, ethyl, trifluoromethyl, nitro, methoxy, ethoxy, and amino;
m is an integer from 0 to 4;
or a salt or isomer thereof.

Without intending to be limited by theory, the electron density on the ring bearing the nitrile may be important in determining activity towards one or both of the PYR1 and PYL2 receptors. Some embodiments with alkoxy and alkyl substitution ortho- to the nitrile provided better activity with PYR1 and PYL2 as compared to halogen or trifluoromethyl substitution, especially bis-trifluoromethyl substitution.

In some preferred embodiments, at least one substituent ortho- to $R^3$ is electron-donating. In some preferred embodiments, at least on substituent ortho- to $R^3$ is $C_1$-$C_4$ alkyl, cyclopropyl, or $C_1$-$C_4$ alkoxy (e.g., methyl, ethoxy, methoxy, ethyl, propyl, and cyclopropyl).

In some preferred embodiments, no more than one ring substituent ortho- to $R^3$ is halo or haloalkyl. In some preferred embodiments, no ring substituent ortho- to $R^3$ is halo or haloalkyl. In some preferred embodiments, no ring substituent ortho- to $R^3$ is electron-withdrawing (e.g., nitro, perfluoroalkyl, carboxy, halo, and the like).

In some preferred embodiments, each ring substituent ortho- to $R^3$ is selected independently from the group consisting of methyl, ethyl, n-propyl, chloro, bromo, trifluoromethyl, methoxy, and ethoxy.

In some embodiments, each ring substituent meta- to $R^3$ is selected independently from the group consisting of hydrogen, nitro, and —N(R$^6$)$_2$. In some embodiments, each ring substituent meta- to $R^3$ is hydrogen or —N(R$^6$)$_2$ (preferably, hydrogen).

In some preferred embodiments, no more than one ring substituent (i.e., $R^{4a}$, $R^{4b}$, $R^{5a}$, or $R^{5b}$) is halo, haloalkyl, nitro, or —SR$^1$. In some embodiments, no ring substituent is halo, haloalkyl, nitro, or —SR$^1$. In some embodiments, no ring substituent is electron-withdrawing (e.g., halo, haloalkyl, or nitro).

One structural feature present in quinabactin is the n-propyl group attached to the dihydroisoquinolinone ring. Without intending to be limited by theory, during binding with PYL2, the n-propyl group is thought to extend into a small hydrophobic cleft, which is known as the 3' tunnel and is lined with the L87, F61, and V163 residues. In some preferred embodiments, a small hydrophobic substituent ortho to the $R^3$ nitrile may occupy this cleft.

In some preferred embodiments, at least one ring substituent ortho- to $R^3$ is a small hydrophobic substituent, such as a $C_{1-3}$ alkyl group (e.g., methyl). In some embodiments, both substituents are small, hydrophobic substituents (e.g., dimethyl; methyl and methoxy).

In some embodiments, $R^{5a}$ and $R^{5b}$ are each independently selected from hydrogen, halo, methyl, ethyl, trifluoromethyl, nitro, methoxy, ethoxy, and amino. In some embodiments, $R^{5a}$ and $R^{5b}$ are each independently selected from hydrogen, halo, methyl, ethyl, trifluoromethyl, and methoxy. In some embodiments, $R^{5a}$ and $R^{5b}$ are each independently selected from hydrogen, halo, and methyl. In some preferred embodiments, $R^{5a}$ and $R^{5b}$ are hydrogen. In some preferred embodiments, $R^{5b}$ is hydrogen.

In some preferred embodiments, m is 1 or 2 (e.g., 1). In some embodiments, m is 0. In some embodiments, m is 1. In some embodiments, m is 2. In some embodiments, m is 3. In some embodiments, m is 4. In some embodiments, m is 5 (e.g., perfluorophenyl).

In some preferred embodiments, the compound of Formula I or II is a compound of Formula III:

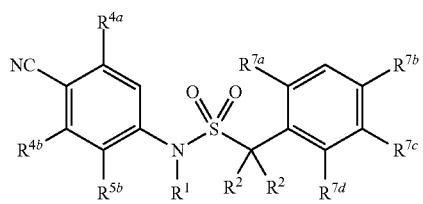

(III)

wherein
$R^{7a}$, $R^{7b}$, $R^{7c}$, and $R^{7d}$ are each independently selected from the group consisting of hydrogen, halo, $C_{1-3}$ alkyl, cyclopropyl, trifluoromethyl, nitro, —OR$^1$, and —N(R$^1$)$_2$;
or a salt or isomer thereof.

In some embodiments, $R^{7a}$ and $R^{7b}$ are each independently selected from halo, nitro, $C_{1-3}$ alkyl, cyclopropyl, —OR$^6$, and —N(R$^6$)$_2$. In some preferred embodiments, $R^{7a}$ is hydrogen or halo. In some preferred embodiments, $R^{7a}$ is hydrogen.

In some preferred embodiments, $R^{7b}$ is not hydrogen. In some preferred embodiments, $R^{7b}$ is $C_{1-3}$ alkyl (e.g., methyl). Without intending to be limited by theory, the calculated position of a methyl group in a 4-methylbenzyl substituent superimposes well with the C-6 methyl group in abscisic acid (ABA).

In some preferred embodiments, $R^{7c}$ and $R^{7d}$ are hydrogen. In some embodiments, $R^{7a}$, $R^{7c}$, and $R^{7d}$ are hydrogen.

The compounds described above can be synthesized using methods known in the art. For example, methods of synthesis are set forth in Intl. Pat. Publ. Nos. WO 2007/068418 A1 and WO 2009/120826 A1; U.S. Pat. App. Publ. Nos. US 2009/0215728 A1 and US 2012/0028923 A1; European Pat. Publ. No. EP 2172456 A1; and Li, Xun et al. Organic Process Research and Development 2009, 13(3), 652-55 as described in U.S. Pat. Nos. 5,498,755 and 6,127,382.

III. ABA Receptor Agonist Formulations

The present invention provides for agricultural chemical formulations formulated for contacting to plants, wherein the formulation comprises an ABA receptor agonist of the present invention. In some embodiments, the plants that are contacted with the agonists comprise or express an endogenous PYR/PYL polypeptide. In some embodiments, the plants that are contacted with the agonists do not comprise or express a heterologous PYR/PYL polypeptide (e.g., the plants are not transgenic or are transgenic but express heterologous proteins other than heterologous PYR/PYL proteins). In some embodiments, the plants that are contacted with the agonists do comprise or express a heterologous PYR/PYL polypeptide as described herein.

In some embodiments, the invention presents the agricultural formulation as otherwise disclosed herein, further comprising at least one of a fungicide, an herbicide, a pesticide, a nematicide, an insecticide, a plant activator, an herbicide safener, a plant growth regulator, an insect repellant, an acaricide, a molluscicide, or a fertilizer.

In some embodiments, the invention presents the agricultural formulation as otherwise disclosed herein, further comprising a surfactant. In some embodiments, the invention presents the agricultural formulation as otherwise disclosed herein, further comprising a a carrier.

In some embodiments, the agricultural formulation further comprises an agricultural chemical that is useful for promoting plant growth, reducing weeds, or reducing pests. In some embodiments, the agricultural formulation further comprises at least one of a fungicide, an herbicide, a pesticide, a nematicide, an insecticide, a plant activator, a synergist, an herbicide safener, a plant growth regulator, an insect repellant, an acaricide, a molluscicide, or a fertilizer.

In some aspects, the invention provides a plant or plant part in contact with the ABA receptor agonist compounds or ABA receptor agonist formulations described herein. In some embodiments, the plant is a seed.

The formulations can be suitable for treating plants or plant propagation material, such as seeds, in accordance with the present invention, e.g., in a carrier. Suitable additives include buffering agents, wetting agents, coating agents, polysaccharides, and abrading agents. Exemplary carriers include water, aqueous solutions, slurries, solids, and dry powders (e.g., peat, wheat, bran, vermiculite, clay, pasteurized soil, many forms of calcium carbonate, dolomite, various grades of gypsum, bentonite and other clay minerals, rock phosphates and other phosphorous compounds, titanium dioxide, humus, talc, alginate and activated charcoal). Any agriculturally suitable carrier known to one skilled in the art would be acceptable and is contemplated for use in the present invention.

In some embodiments, the formulations can also include at least one surfactant, herbicide, fungicide, pesticide, or fertilizer. In some embodiments, the agricultural chemical formulation comprises at least one of a surfactant, an herbicide, a pesticide, such as but not limited to a fungicide, a bactericide, an insecticide, an acaricide, and a nematicide, a plant activator, a synergist, an herbicide safener, a plant growth regulator, an insect repellant, or a fertilizer. In some embodiments, the agricultural chemical formulation comprises at least one of an herbicide, a fungicide, a bactericide, an insecticide, an acaricide, a nematicide, and an insect repellent. In some embodiments, the agricultural chemical formulation comprises a plant activator, an herbicide safener, a plant growth regulator, an insect repellant, or a fertilizer.

In some embodiments, the agricultural chemical formulation comprises an effective amount of one or more herbicides selected from the group consisting of paraquat (592), mesotrione (500), sulcotrione (710), clomazone (159), fentrazamide (340), mefenacet (491), oxaziclomefone (583), indanofan (450), glyphosate (407), prosulfocarb (656), molinate (542), triasulfuron (773), halosulfuron-methyl (414), and pretilachlor (632). The above herbicidal active ingredients are described, for example, in "The Pesticide Manual," 12th ed., C. D. S. Tomlin (ed.), British Crop Protection Council, 2000, under the entry numbers added in parentheses; for example, mesotrione (500) is described therein under entry number 500. The above compounds are described, for example, in U.S. Pat. No. 7,338,920, which is incorporated by reference herein in its entirety.

In some embodiments, the agricultural chemical formulation comprises an effective amount of one or more fungicides selected from the group consisting of: sedaxane, fludioxonil, penthiopyrad, prothioconazole, flutriafol, difenoconazole, azoxystrobin, captan, cyproconazole, cyprodinil, boscalid, diniconazole, epoxiconazole, fluoxastrobin, trifloxystrobin, metalaxyl, metalaxyl-M (mefenoxam), fluquinconazole, fenarimol, nuarimol, pyrifenox, pyraclostrobin, thiabendazole, tebuconazole, triadimenol, benalaxyl, benalaxyl-M, benomyl, carbendazim, carboxin, flutolanil, fuberizadole, guazatine, myclobutanil, tetraconazole, imazalil, metconazole, bitertanol, cymoxanil, ipconazole, iprodione, prochloraz, pencycuron, propamocarb, silthiofam, thiram, triazoxide, triticonazole, tolylfluanid, and a manganese compound (such as mancozeb, maneb). In some embodiments, the agricultural chemical formulation comprises an effective amount of one or more of an insecticide, an acaricide or nematcide selected from the group consisting of: thiamethoxam, imidacloprid, clothianidin, lamda-cyhalothrin, tefluthrin, beta-cyfluthrin, permethrin, abamectin, fipronil, and spinosad. Details (e.g., structure, chemical name, commercial names, etc) of each of the above pesticides with a common name can be found in the e-Pesticide Manual, version 3.1, 13th Edition, Ed. CDC Tomlin, British Crop Protection Council, 2004-05. The above compounds are described, for example, in U.S. Pat. No. 8,124,565, which is incorporated by reference herein in its entirety.

In some embodiments, the agricultural chemical formulation comprises an effective amount of one or more fungicides selected from the group consisting of cyprodinil (i.e., (4-cyclopropyl-6-methyl-pyrimidin-2-yl)-phenyl-amine) (208), dodine (289); chlorothalonil (142); folpet (400); prothioconazole (685); boscalid (88); proquinazid (682); dithianon (279); fluazinam (363); ipconazole (468); and metrafenone. Some of the above compounds are described, for example, in "The Pesticide Manual" [The Pesticide Manual—A World Compendium; Thirteenth Edition; Editor: C. D. S. Tomlin; The British Crop Protection Council, 2003], under the entry numbers added in parentheses. The above compounds are described, for example, in U.S. Pat. No. 8,349,345, which is incorporated by reference herein in its entirety.

In some embodiments, the agricultural chemical formulation comprises an effective amount of one or more fungicides selected from fludioxonil, metalaxyl and a strobilurin fungicide, or a mixture thereof. In some embodiments, the strobilurin fungicide is azoxystrobin, picoxystrobin, kresoxim-methyl, or trifloxystorbin. In some embodiments, the agricultural chemical formulation comprises an effective amount of one or more of an insecticide selected from a phenylpyrazole and a neonicotinoid. In some embodiments, the phenylpyrazole is fipronil and the neonicotinoid is selected from thiamethoxam, imidacloprid, thiacloprid, clothianidin, nitenpyram and acetamiprid. The above compounds are described, for example, in U.S. Pat. No. 7,071,188, which is incorporated by reference herein in its entirety.

In some embodiments, the agricultural chemical formulation comprises an effective amount of one or more biological pesticide, including but not limited to, *Pasteuria* spp., *Paeciliomyces, Pochonia chlamydosporia, Myrothecium* metabolites, *Muscodor* volatiles, *Tagetes* spp., *bacillus firmus*, including *bacillus firmus* CNCM I-1582.

IV. Application to Plants

The ABA receptor agonist formulations and compositions can be applied to plants using a variety of known methods, e.g., by spraying, atomizing, dipping, pouring, irrigating, dusting or scattering the compositions over the propagation material, or brushing or pouring or otherwise contacting the compositions over the plant or, for a seed, by coating, encapsulating, spraying, dipping, immersing the seed in a liquid composition, or otherwise treating the seed. In an alternative to directly treating a plant or seed before planting, the formulations of the invention can also be introduced into the soil or other media into which the seed is to be planted. For example, the formulations can be introduced into the soil by spraying, scattering, pouring, irrigating or otherwise treating the soil.

In some embodiments, a carrier is also used. The carrier can be solid or liquid, as noted above. In some embodiments peat is suspended in water as a carrier of the ABA receptor agonist, and this mixture is sprayed into the soil or planting media or over the seed as it is planted.

The types of plant that can be treated with the ABA receptor agonists described herein include both monocotyledonous (i.e., monocot) and dicotyledonous (i.e., dicot) plant species including cereals such as barley, rye, sorghum, tritcale, oats, rice, wheat, soybean and corn; beets (for example, sugar beet and fodder beet); cucurbits including cucumber, muskmelon, canteloupe, squash and watermelon; cale crops including broccoli, cabbage, cauliflower, bok choi, and other leafy greens, other vegetables including tomato, pepper, lettuce, beans, pea, onion, garlic and peanut; oil crops including canola, peanut, sunflower, rape, and soybean; solanaceous plants including tobacco; tuber and root crops including potato, yam, radish, beets, carrots and sweet potatoes; fruits including strawberry; fiber crops including cotton and hemp; other plants including coffee, bedding plants, perennials, woody ornamentals, turf and cut flowers including carnation and roses; sugar cane; containerized tree crops; evergreen trees including fir and pine; deciduous trees including maple and oak; and fruit and nut trees including cherry, apple, pear, almond, peach, walnut and citrus.

It will be understood that the ABA receptor agonists described herein mimic the function of ABA on cells. Thus, it is expected that one or more cellular responses triggered by contacting the cell with ABA will also be triggered be contacting the cell with the ABA receptor agonists described herein. The ABA receptor agonists described herein mimic the function of ABA and are provided in a useful formulation.

In some aspects, the invention presents a method of bringing a plant in contact with the agricultural formulation as otherwise disclosed herein, comprising contacting the plant with the agricultural formulation.

V. Methods of Increasing Abiotic Stress Tolerance in Plants

The present invention also provides methods of increasing abiotic stress tolerance in a plant. Thus, in some embodiments, a plant is contacted with an ABA receptor agonist described herein, or an ABA receptor agonist formulation, in sufficient amount to increase the abiotic stress tolerance in the plant. The amount of the ABA receptor agonist formulation applied to the plant can be sufficient to increase the abiotic stress tolerance compared to not contacting the plant with the ABA receptor agonist formulation. The plant can be contacted with the ABA formulation using any of the methods described herein. The increase in abiotic stress tolerance can improve the plants growth or survival to abiotic stress conditions that adversely effect the plant's growth or survival. Abiotic stress includes physical or chemical conditions described herein, but preferably is drought resistance or drought tolerance.

In some embodiments, application of the ABA receptor agonists or ABA receptor agonist formulations described herein increases the abiotic stress resistance of a plant.

In some aspects, the invention presents a method of increasing drought tolerance in a plant, the method comprising contacting a plant with a sufficient amount of the agricultural formulation as otherwise disclosed herein, thereby increasing drought tolerance in the plant compared to not contacting the plant with the formulation.

In some aspects, the invention provides methods for increasing abiotic stress tolerance in a plant, the method comprising the step of contacting a plant with a sufficient amount of the above formulations to increase abiotic stress tolerance in the plant compared to the abiotic stress tolerance in the plant when not contacted with the formulation. In some embodiments, the plant is a monocot. In some embodiments, the plant is a dicot. In some embodiments, the abiotic stress tolerance comprises drought tolerance.

Abiotic stress resistance can assayed according to any of a number of well-known techniques. For example, for drought tolerance, plants can be grown under conditions in which less than optimum water is provided to the plant. Drought resistance can be determined by any of a number of standard measures including turgor pressure, growth, yield, and the like.

VI. Methods of Inhibiting Seed Germination in a Plant

The present invention also provides methods of inhibiting seed germination. Thus, in some embodiments, a plant, plant part, or a seed is contacted with an ABA receptor agonist formulation in an amount sufficient to inhibit seed germination. The seed can be contacted with the ABA receptor agonist formulation using any of the methods described herein. In some embodiments, the seed is directly contacted with the ABA receptor agonist formulation. In some embodiments, the ground or soil is contacted with the ABA receptor agonist formulation either prior to or after planting or sowing the seeds. In some embodiments, a plant is contacted with sufficient ABA receptor agonist formulation to inhibit germination of seeds that later develop from the plant.

In some aspects, the invention provides a method of inhibiting seed germination in a plant, the method comprising the step of contacting a plant, a plant part, or a plant seed with a sufficient amount of the above formulations to inhibit germination. In some embodiments, application of the ABA receptor agonists described herein to seeds inhibits germination of the seeds.

VII. Methods of Activating PYR/PYL Receptor Polypeptides

The present invention also provides methods of activating a PYR/PYL receptor polypeptide. In some embodiments, a PYR/PYL polypeptide is contacted with a compound described above, and the activated PYR/PYL polypeptide binds to a PP2C polypeptide. In some embodiments, the PYR/PYL polypeptide is capable of being activated by the agonist compound quinabactin. In some embodiments, the PYR/PYL protein that is activated is substantially identical to any one of SEQ ID NOs:1-119. Examples of sequences of ABA receptors from various plants are provided in U.S. Pat. App. Pub. 2011/0271408, which is incorporated by reference herein in its entirety.

In some aspects, the invention provides a method of activating a PYR/PYL protein. In some embodiments, the method comprises the step of contacting the PYR/PYL protein with any of the compounds described herein (e.g., a compound of Formula I, II, or III as disclosed herein).

In some embodiments, the PYR/PYL protein is expressed by a cell. In some embodiments, the PYR/PYL protein is expressed by a plant cell. In some embodiments, the PYR/PYL protein is an endogenous protein. In some embodiments, the PYR/PYL protein is a heterologous protein. In some embodiments, the cell further expresses a type 2 protein phosphatase (PP2C). In some embodiments, the type 2 protein phosphatase is HAB1 (Homology to ABI1), ABI1 (Abscisic acid insensitive 1), or ABI2 (Abscisic acid insensitive 2).

In some embodiments, the method activates a PYR/PYL receptor in a cell free in vitro assay. In some embodiments, the method activates a PYR/PYL receptor expressed in a cell. In some embodiments, the cell is a plant cell. In some embodiments, the cell is an animal or mammalian cell. In some embodiments, the cell expresses an endogenous PYR/PYL protein. In some embodiments, the cell is engineered to express a heterologous PYR/PYL polypeptide. In some embodiments, the cell expresses a heterologous PP2C polypeptide. In some embodiments, the cell expresses a PP2C polypeptide selected from HAB1 (homology to ABI1), ABI1, or ABI2.

In some embodiments, the activated PYR/PYL polypeptide induces expression of heterologous genes. In some embodiments, the heterologous genes are ABA-responsive genes. In some embodiments, the induced gene expression occurs in cells that express an endogenous PYR/PYL polypeptide. In some embodiments, the induced gene expression occurs in cells that express a heterologous PYR/PYL polypeptide.

VIII. Screening for New ABA Receptor Agonists and Antagonists

For the present invention, an agent agonizes a PYR/PYL receptor if, when the agent is present at a concentration no greater than 200 µM, contacting the agent to the PYR/PYL receptor results in activation or up-regulation of the activity of the PYR/PYL receptor. If an agent does not induce activation or up-regulation of a PYR/PYL receptor protein's activity when the agent is present at a concentration no greater than 200 µM, then the agent does not significantly agonize the PYR/PYL receptor.

As used herein, "activation" requires a minimum threshold of activity to be induced by the agent. Determining whether this minimum threshold of activity has been met can be accomplished, e.g., by using an enzymatic phosphatase assay that sets a minimum value for the level of enzymatic activity that must be induced, or by using an enzymatic phosphatase assay in the presence of a colorimetric detection reagent (e.g., para-nitrophenylphosphate) wherein the minimum threshold of activity has been met if a color change is observed.

A number of different screening protocols can be utilized to identify agents that agonize or antagonize a PYR/PYL polypeptide. Screening can take place using isolated, purified or partially purified reagents. In some embodiments, purified or partially purified PYR/PYL polypeptide can be used.

Alternatively, cell-based methods of screening can be used. For example, cells that naturally-express a PYR/PYL polypeptide or that recombinantly express a PYR/PYL polypeptide can be used. In some embodiments, the cells used are plant cells, animal cells, bacterial cells, fungal cells, including but not limited to yeast cells, insect cells, or mammalian cells. In general terms, the screening methods involve screening a plurality of agents to identify an agent that modulates the activity of a PYR/PYL polypeptide by, e.g., binding to PYR/PYL polypeptide, or activating a PYR/PYL polypeptide or increasing expression of a PYR/PYL polypeptide, or a transcript encoding a PYR/PYL polypeptide.

1. PYR/PYL Polypeptide Binding Assays

Optionally, preliminary screens can be conducted by screening for agents capable of binding to a PYR/PRL polypeptide, as at least some of the agents so identified are likely PYR/PYL polypeptide modulators.

Binding assays can involve contacting a PYR/PYL polypeptide with one or more test agents and allowing sufficient time for the protein and test agents to form a binding complex. Any binding complexes formed can be detected using any of a number of established analytical techniques. Protein binding assays include, but are not limited to, methods that measure co-precipitation or co-migration on non-denaturing SDS-polyacrylamide gels, and co-migration on Western blots (see, e.g., Bennet, J. P. and Yamamura, H. I. (1985) "Neurotransmitter, Hormone or Drug Receptor Binding Methods," in *Neurotransmitter Receptor Binding* (Yamamura, H. I., et al., eds.), pp. 61-89). Other binding assays involve the use of mass spectrometry or NMR techniques to identify molecules bound to PYR/PYL polypeptide or displacement of labeled substrates (e.g., labeled ABA). The PYR/PYL polypeptide protein utilized in such assays can be naturally expressed, cloned or synthesized.

2. Activity

PYR/PYL polypeptide agonists can be identified by screening for agents that activate or increase activity of a PYR/PYL polypeptide. Antagonists can be identified by reducing activity.

One activity assay involves testing whether a candidate agonist can induce binding of a PYR/PYL protein to a type 2 protein phosphatase (PP2C) polypeptide in an agonist-specific fashion. Mammalian or yeast two-hybrid approaches (see, e.g., Bartel, P. L. et. al. *Methods Enzymol*, 254:241 (1995)) can be used to identify polypeptides or other molecules that interact or bind when expressed together in a cell. In some embodiments, agents that agonize a PYR/PYL polypeptide are identified in a two-hybrid assay between a PYR/PYL polypeptide and a type 2 protein phosphatase (PP2C) polypeptide (e.g., ABI1 or 2 or orthologs thereof, e.g., from the group A subfamily of PP2Cs), wherein an ABA receptor agonist is identified as an agent that activates or enables binding of the PYR/PYL polypeptide and the PP2C polypeptide. Thus, the two polypeptides bind in the presence, but not in the absence of the agent. In some embodiments, a chemical compound or agent is identified as an agonist of a PYR/PYL protein if the yeast cell turns blue in the yeast two hybrid assay, The biochemical function of PYR1, and PYR/PYL proteins in general, is to inhibit PP2C activity. This can be measured in live cells using the yeast two hybrid or other cell-based methods. It can also be measured in vitro using enzymatic phosphatase assays in the presence of a colorimetric detection reagent (for example, para-nitrophenylphosphate). The yeast-based assay used above provides an indirect indicator of ligand binding. To address this potential limitation, one can use in vitro competition assays, or cell based assays using other organisms, as alternate approaches for identifying weak binding target compounds.

3. Expression Assays

Screening for a compound that increases the expression of a PYR/PYL polypeptide is also provided. Screening methods generally involve conducting cell-based or plant-based assays in which test compounds are contacted with one or more cells expressing PYR/PYL polypeptide, and then detecting an increase in PYR/PYL expression (either transcript or translation product). Assays can be performed with cells that naturally express PYR/PYL or in cells recombinantly altered to express PYR/PYL, or in cells recombinantly altered to express a reporter gene under the control of the PYR/PYL promoter.

Various controls can be conducted to ensure that an observed activity is authentic including running parallel reactions with cells that lack the reporter construct or by not contacting a cell harboring the reporter construct with test compound.

4. Validation

Agents that are initially identified by any of the foregoing screening methods can be further tested to validate the apparent activity or determine other biological effects of the agent. In some cases, the identified agent is tested for the ability to effect plant stress (e.g., drought tolerance), seed germination, or another phenotype affected by ABA. A number of such assays and phenotypes are known in the art and can be employed according to the methods of the invention.

EXAMPLES

Example 1: Preparation of 4-Cyanophenyl Sulfonamides

A small library of sulfonamide analogs was assembled via a coupling reaction between various substituted 4-cyanoanilines (5-19) and 4-substituted benzylsulfonyl chloride (Scheme 1). While anilines 5-9 were commercially available, anilines 10, 11 and 13-16 were synthesized according to protocols specified in the literature. Aniline 17 and 19 were synthesized using high-yielding Suzuki coupling reactions with either triethylborane or cyclopropylboronic acids using substrates 16. Negishi coupling reactions were performed with substrates 7 and 16, using n-propylzincbromide solution to yield anilines 12 and 18.

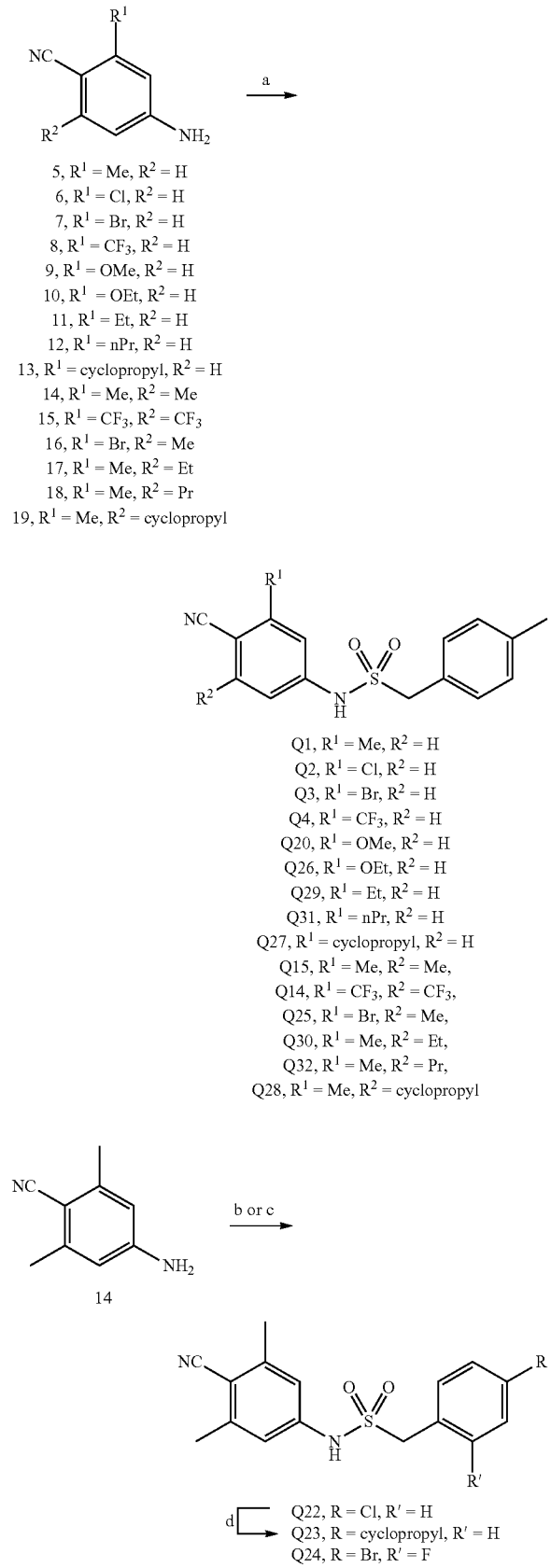

Scheme 1

-continued

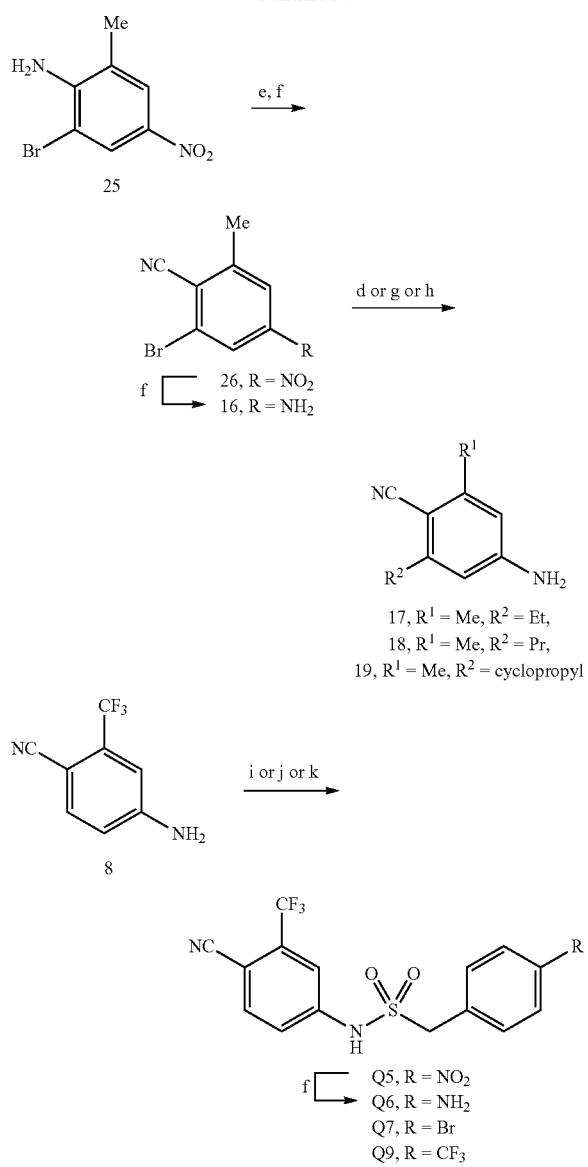

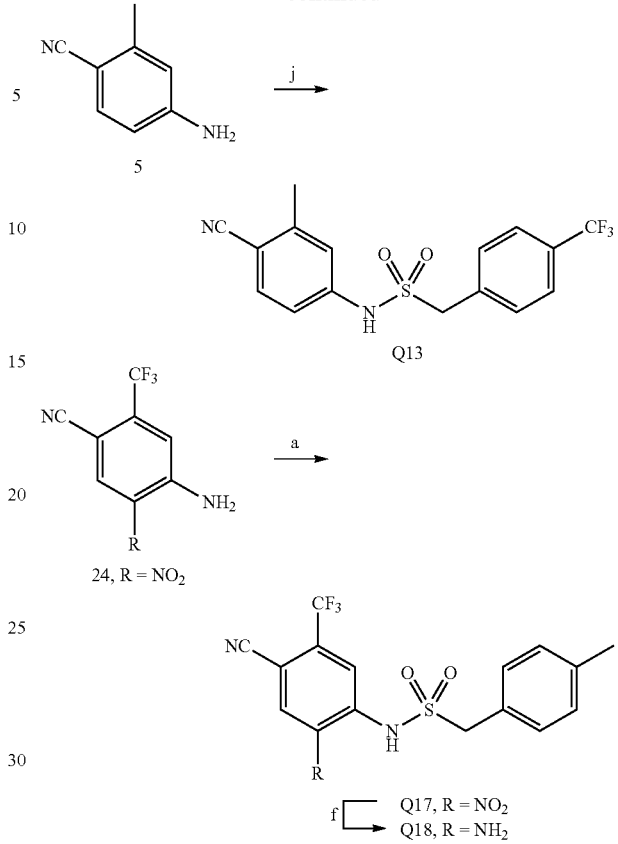

Reagents and Conditions: (a) p-methylbenzylsulfonyl chloride, DIPEA, DCM, 0° C.-RT, 12 h; (b) p-chlorobenzylsulfonyl chloride, DIPEA, DCM, 0° C.-RT, 12 h; (c) 4-bromo-2-fluorobenzylsulfonyl chloride, DIPEA, DCM, 0° C.-RT, 12 h; (d) cyclopropylboronic acid, P(Cy)$_3$, K$_3$PO$_4$, Pd(OAc)$_2$, THF, 100° C., 12 h; (e) CuCN, t-butylnitrite, acetonitrile, 70° C., 2 h (f) Zn, ammonium formate, MeOH, RT, 30 min; (g) triethylborane, CsOAc, Pd(dppf)Cl$_2$, THF, reflux, 12 h; (h) nPrZnBr, Pd(OAc)$_2$, XPhos, THF, 50° C., 2 h; (i)p-nitrobenzylsulfonyl chloride, DIPEA, DCM, 0° C.-RT, 12 h; (j) p-trifluoromethylbenzylsulfonyl chloride, DIPEA, DCM, 0° C.-RT, 12 h; (k) p-bromobenzylsulfonyl chloride, DIPEA, DCM, 0° C.-RT, 12 h (l) acetyl chloride, pyridine, 0° C.-RT, 3 h; (m) n-propanal, sulfuric acid, sodium borohydride, 0° C.-RT, 6 h.

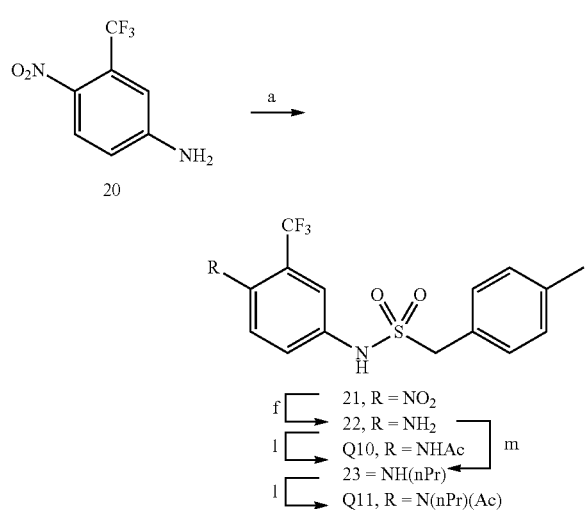

General Procedures

Unless stated otherwise, all reactions were carried out under an atmosphere of argon in oven-dried glassware. Indicated reaction temperatures refer to those of the reaction bath, while room temperature (RT or rt) is noted as 25° C. All other solvents were of commercially available anhydrous quality and used as received. Pure reaction products were typically dried under high vacuum. Commercially available starting materials and reagents were used as received unless specified otherwise. Analytical thin layer chromatography (TLC) was performed with (5×20 cm, 60 Å, 250 µm). Visualization was accomplished using a 254 nm UV lamp.

Intermediates 5, 6, 7, 8, 9, 20, and several substituted benzyl sulfonyl chlorides listed in the reagents and conditions section were commercially available. Intermediates 10, 11, 13-15, and 24 were synthesized according literature protocols given in Int'l Pat. Pub. No. WO 2007/068418 A1/U.S. Pat. App. Pub. No. 2008/0312230 (compound 10), Int'l Pat. Pub. No. WO 2009/120826 A1/U.S. Pat. App. Pub. No. 2009/0270363 (compound 11), U.S. Pat. App. Pub. Nos.

US 2009/0215728 A1 and 2012/0028923 A1, as well as European Pat. Pub. No. EP 2172456 A1/U.S. Pat. App. Pub. No. 2010/0179172 (compounds 13-15); and Li, Xun; Ng, Raymond; Zhang, YongSheng; Russel, Ronald; Sui, Zhihua. Organic Process Research and Development 2009, 13(3), 652-55 (compound 24).

$^1$H NMR spectra were recorded on a 400 MHz spectrophotometer. Chemical shifts are reported in ppm with the solvent resonance as internal standard ([DMSO-d6 2.5 ppm] for $^1$H, $^{13}$C respectively). Data are reported as follows: chemical shift, multiplicity (s=singlet, d=doublet, dd=doublet of doublet, t=triplet, q=quartet, br=broad, m=multiplet), number of protons, and coupling constants. All compounds submitted for biological testing were found to be ≥95% pure.

General Procedure for Sulfonamide Coupling Reaction

To a cold solution of aryl amine (1 equiv) in anhydrous DCM was added (3 equiv) of diisopropylethylamine followed by the desired sulfonyl chloride. The solution was stirred for 12 h, and the reaction was quenched by adding dilute hydrochloric acid (2N). The reaction mixture was extracted in dichloromethane, dried over anhydrous sodium sulfate, and concentrated in vacuo. The residue was purified by silica gel flash chromatography using a hexanes/ethyl acetate gradient from 0%-50% to yield pure compounds as yellowish white powders in 60-80% yields.

Exemplary Procedure for Suzuki Coupling with Triethylborane

Triethylborane solution (8.36 mL, 2.8 equiv) was added to a solution of aryl bromide, amine 16 (0.63 g, 1 equiv), Pd(dppf)Cl$_2$ (43.2 mg, 0.02 equiv), and CsOAc (1.15 g, 2.0 equiv) in THF. The mixture was heated at reflux overnight until all the starting material was consumed. After cooling, the reaction mixture was diluted with ethyl acetate and washed with sodium bicarbonate solution and brine, dried over anhydrous sodium sulfate, and concentrated. The residue was purified by silica gel flash chromatography with a hexanes/ethyl acetate gradient from 0%-60%, which yielded 17 (0.4 g) as a white solid in 85% yield.

General Procedure for Suzuki Coupling with Cyclopropylboronic Acid

To a solution of 16 or Q22 (1 equiv), boronic acid (2.5 equiv), potassium phosphate (4.0 equiv), and tricylohexylphosphine (0.1 equiv) in toluene/water (1:20 v/v) was added palladium actetate (0.05 equiv). The mixture was heated at 100° C. overnight and then cooled to room temperature. Water was added to the reactions, and the mixture was extracted with ethyl acetate; the combined extracts were washed with brine, dried over anhydrous sodium sulfate, and concentrated in vacuo. The residue was purified using silica gel flash chromatography to afford 19 and Q23 as white solids in 75% and 70% yields respectively.

General Procedure for Negishi Coupling

To a solution of aryl bromide 7 or 16 (1 equiv), Pd(OAc)$_2$ (0.05 equiv), and XPhos (0.1 equiv) at 0° C. was added a solution of n-propylzinc bromide (1.8 equiv) in THF. The mixture was then heated in an oil bath at 50° C. for 2 h. The reaction was cooled and quenched slowly by addition of water, the reaction mixture was extracted with ethyl acetate, and the combined extracts were dried over sodium sulfate and concentrated in vacuo. The residue was purified by silica gel flash chromatography using a hexanes/ethyl acetate gradient to yield anilines 12 and 18 in 65% and 60% yields respectively.

General Procedure for Reduction of Nitro Derivatives

To a cold solution of the aryl nitro derivative (1 equiv) in methanol, was added ammonium formate (10 equiv), followed by slow addition of powdered zinc dust (10 equiv). The reaction was stirred for 30 min and concentrated in vacuo. The residue was adsorbed on silica gel and purified using flash chromatography (hexanes/ethyl acetate gradient from 0-60%) to yield products in near-quantitative yields.

Procedure for Reductive Amination for Synthesis of Amine 23

To a cold solution of amine 22 (500 mg, 1 equiv) in 3 mL of 3 M H$_2$SO$_4$ was added n-propanal (130 uL, 1.2 equiv). The mixture was stirred for 30 min at 0° C.; thereafter, sodium borohydride (137 mg, 2.5 equiv) was added portionwise, and the reaction was slowly brought to room temperature over 6 h. The reaction was quenched with saturated bicarbonate solution and extracted with ethyl acetate; the combined extracts were dried over sodium sulfate and concentrated in vacuo. The residue was purified using silica gel flash chromatography to yield the yellowish product in 70% yield.

General Procedure for Synthesis of Amides Q10 and Q11

To a cold solution of anilines 22 or 23 (1 equiv) in pyridine was added acetyl chloride (1.5 equiv). The reaction was stirred for 3 h and then diluted with water. The reaction mixture was extracted with three times with ethyl acetate, and the combined extracts were dried over sodium sulfate and concentrated in vacuo. The residue was purified using silica gel flash chromatography to yield off-white powders Q10 and Q11 in 75% and 78% yield respectively.

Synthesis of Intermediate 26 Via Diazotization/Cyanation of 25

To a solution of CuCN (1.94 g, 2.5 equiv), in acetonitrile (50 mL) was added t-butyl nitrite (2.06 mL, 2.0 equiv). The mixture was cooled to 0° C. and intermediate 25 (2 g, 1 equiv) was added portionwise over 10 min. The mixture was heated for 2 h at 70° C., quenched with a 10% solution of sodium carbonate, and the pH was adjusted to 11 using a 1 M solution of NaOH. The reaction was extracted with ethyl acetate; the combined organic extracts were washed with brine, dried over sodium sulfate, and concentrated in vacuo. The residue was purified using flash chromatography using hexanes/ethyl acetate gradient (0-50%) to give compound as a yellow solid in 65% yield.

N-(4-Cyano-3-methylphenyl)-1-(4-methylphenyl)methanesulfonamide (Q1)

$^1$H NMR (400 MHz, DMSO-d6) δ ppm 2.25 (s, 3H) 2.37 (s, 3H) 4.52 (s, 2H) 6.99-7.07 (m, 2H) 7.07-7.14 (m, 4H)

7.63 (d, J=8.58 Hz, 1H), 10.31 (s, 1H) ESI HRMS [M+NH$_4$]$^+$ for C$_{16}$H$_{16}$N$_2$O$_2$S found 318.1312.

N-(3-Chloro-4-cyanophenyl)-1-(4-methylphenyl)methanesulfonamide (Q2)

$^1$H NMR (400 MHz, DMSO-d6) δ ppm 2.25 (s, 3H) 4.60 (s, 2H) 7.05-7.18 (m, 6H) 7.79 (d, J=8.58 Hz, 1H) 10.62 (s, 1H) ESI HRMS [M+NH$_4$]$^+$ for C$_{15}$H$_{13}$ClN$_2$O$_2$S found 338.0721.

N-(3-Bromo-4-cyanophenyl)-1-(4-methylphenyl)methanesulfonamide (Q3)

$^1$H NMR (400 MHz, DMSO-d6) δ ppm 2.25 (s, 3H) 4.59 (s, 2H) 7.05-7.20 (m, 5H) 7.26 (d, J=2.34 Hz, 1H) 7.76 (d, J=8.58 Hz, 1H) 10.58 (s, 1H) ESI HRMS [M+NH$_4$]$^+$ for C$_{15}$H$_{13}$BrN$_2$O$_2$S found 384.0338.

N-(4-Cyano-3-(trifluoromethyl)-phenyl)-1-(4-methylphenyl)methanesulfonamide (Q4)

$^1$H NMR (400 MHz, DMSO-d6) δ ppm 2.21 (s, 3H) 4.63 (s, 2H) 7.01-7.15 (m, 4H) 7.31-7.41 (m, 2H) 7.96 (d, J=7.80 Hz, 1H) 10.79 (s, 1H) ESI HRMS [M+NH$_4$]$^+$ for C$_{16}$H$_{13}$F$_3$N$_2$O$_2$S found 372.0968.

N-(4-Cyano-3-methoxyphenyl)-1-(4-methylphenyl)methanesulfonamide (Q20)

$^1$H NMR (400 MHz, DMSO-d6) d ppm 2.25 (s, 3H) 3.79 (s, 3H) 4.55 (s, 2H) 6.72-6.85 (m, 2H) 7.11 (s, 4H) 7.58 (d, J=8.58 Hz, 1H) 10.36 (s, 1H) ESI HRMS [M+NH$_4$]$^+$ for C$_{16}$H$_{16}$N$_2$O$_3$S found 334.1262.

N-(4-Cyano-3-ethoxyphenyl)-1-(4-methylphenyl)methanesulfonamide (Q26)

$^1$H NMR (400 MHz, DMSO-d6) δ ppm 1.33 (t, J=7.02 Hz, 3H) 2.25 (s, 3H) 4.03 (d, J=7.02 Hz, 2H) 4.54 (s, 2H) 6.72-6.83 (m, 2H) 7.10 (s, 4H) 7.57 (d, J=8.58 Hz, 1H) 10.33 (s, 1H) ESI HRMS [M+NH$_4$]$^+$ for C$_{17}$H$_{18}$N$_2$O$_3$S found 348.1458.

N-(4-Cyano-3-ethylphenyl)-1-(4-methylphenyl)methanesulfonamide (Q29)

$^1$H NMR (400 MHz, DMSO-d6) δ ppm 1.15 (t, J=7.80 Hz, 3H) 2.24 (s, 3H) 2.67 (q, J=7.28 Hz, 2H) 4.52 (s, 2H) 7.02-7.14 (m, 6H) 7.63 (d, J=8.58 Hz, 1H) 10.31 (s, 1H) ESI HRMS [M+NH$_4$]$^+$ for C$_{17}$H$_{18}$N$_2$O$_2$S found 332.1511.

N-(4-Cyano-3-propylphenyl)-1-(4-methylphenyl)methanesulfonamide (Q31)

$^1$H NMR (400 MHz, DMSO-d6) δ ppm 0.89 (t, J=7.41 Hz, 3H) 1.57 (m, 2H) 2.24 (s, 3H) 2.63 (t, J=8 Hz, 2H) 4.51 (s, 2H) 7.01-7.13 (m, 6H) 7.64 (d, J=8.58 Hz, 1H) 10.30 (s, 1H) ESI HRMS [M+NH$_4$]$^+$ for C$_{18}$H$_{20}$N$_2$O$_2$S found 346.1654.

N-(4-Cyano-3-cyclopropylphenyl)-1-(4-methylphenyl)methanesulfonamide (Q27)

$^1$H NMR (400 MHz, DMSO-d6) δ ppm 0.56-0.65 (m, 2H) 1.03-1.12 (m, 2H) 2.03-2.12 (m, 1H) 2.22 (s, 3H) 4.48 (s, 2H) 6.63 (d, J=2.34 Hz, 1H) 6.99-7.13 (m, 5H) 7.61 (d, J=8.58 Hz, 1H) 10.22 (s, 1H) ESI HRMS [M+NH$_4$]$^+$ for C$_{18}$H$_{18}$N$_2$O$_2$S found 344.1499.

N-(4-Cyano-3, 5-dimethylphenyl)-1-(4-methylphenyl)methanesulfonamide (Q15)

$^1$H NMR (400 MHz, DMSO-d6) δ ppm 2.25 (s, 3H) 2.35 (s, 6H) 4.52 (s, 2H) 6.85 (m, 2H) 7.10 (m, 4H) 10.22 (s, 1H) ESI HRMS [M+NH$_4$]$^+$ for C$_{17}$H$_{18}$N$_2$O$_2$S found 332.1523.

N-(4-Cyano-3, 5-(bistrifluoromethyl)phenyl)-1-(4-methylphenyl) methanesulfonamide (Q14)

$^1$H NMR (400 MHz, DMSO-d6) δ ppm 2.18 (s, 3H) 4.73 (s, 2H) 7.00 (d, J=8.58 Hz, 2H) 7.11-7.27 (m, 3H) 7.52 (s, 2H) 11.20 (br. s., 1H) ESI HRMS [M+NH$_4$]$^+$ for C$_{17}$H$_{12}$F$_6$N$_2$O$_2$S found 440.0778.

N-(3-Bromo-4-cyano-5-methylphenyl)-1-(4-methylphenyl)methanesulfonamide (Q25)

$^1$H NMR (400 MHz, DMSO-d6) δ ppm 2.25 (s, 3H) 2.39 (s, 3H) 4.59 (s, 2H) 7.14-7.10 (m, 6H) 10.49 (s, 1H)) ESI HRMS [M+NH$_4$]$^+$ for C$_{16}$H$_{15}$BrN$_2$O$_2$S found 398.0362.

N-(4-Cyano-3-ethyl-5-methylphenyl)-1-(4-methylphenyl)methanesulfonamide (Q30)

$^1$H NMR (400 MHz, DMSO-d6) δ ppm 1.14 (t, J=7.41 Hz, 3H) 2.24 (s, 3H) 2.35 (s, 3H) 2.66 (q, J=7.80 Hz, 2H) 4.52 (s, 2H) 6.87 (d, J=6.24 Hz, 2H) 7.10 (s, 4H) 10.23 (s, 1H) ESI HRMS [M+NH$_4$]$^+$ for C$_{18}$H$_{20}$N$_2$O$_2$S found 346.1640.

N-(4-Cyano-3-methyl-5-propylphenyl)-1-(4-methylphenyl)methanesulfonamide (Q32)

$^1$H NMR (400 MHz, DMSO-d6) δ ppm 0.87 (t, J=8 Hz, 3H) 1.55 (m, 2H) 2.24 (s, 3H) 2.35 (s, 3H) 2.62 (t, J=8 Hz, 2H) 4.51 (s, 2H) 6.81-6.92 (m, 2H) 7.09 (m, 4H) 10.22 (s, 1H) ESI HRMS [M+NH$_4$]$^+$ for C$_{19}$H$_{22}$N$_2$O$_2$S found 360.1831.

N-(4-Cyano-3-cyclopropyl-5-methylphenyl)-1-(4-methylphenyl) methanesulfonamide (Q28)

$^1$H NMR (400 MHz, DMSO-d6) δ ppm 0.54-0.64 (m, 2H) 0.99-1.09 (m, 2H) 2.01-2.12 (m, 1H) 2.27 (s, 3H) 2.35 (s, 3H) 4.48 (s, 2H) 6.41-6.48 (m, 1H) 6.84 (s, 1H) 7.04-7.11 (m, 4H) 10.13 (s, 1H) ESI HRMS [M+NH$_4$]$^+$ for C$_{19}$H$_{20}$N$_2$O$_2$S found 358.1586.

1-(4-Chlorophenyl)-N-(4-cyano-3,5-dimethylphenyl)methanesulfonamide (Q22)

$^1$H NMR (400 MHz, DMSO-d6) δ ppm 2.36 (s, 6H) 4.62 (s, 2H) 6.86 (s, 2H) 7.20-7.27 (m, 2H) 7.33-7.40 (m, 2H) 10.28 (s, 1H) ESI HRMS [M+NH$_4$]$^+$ for C$_{16}$H$_{15}$ClN$_2$O$_2$S found 352.0886.

N-(4-Cyano-3,5-dimethylphenyl)-1-(4-cyclopropylphenyl)methanesulfonamide (Q23)

$^1$H NMR (400 MHz, DMSO-d6) δ ppm 0.54-0.64 (m, 2H) 0.88-0.96 (m, 2H) 1.79-1.90 (m, 1H) 2.34 (s, 6H) 4.51 (s,

1-(4-Bromo-2-fluorophenyl)-N-(4-cyano-3,5-dimethylphenyl)methanesulfonamide (Q24)

$^1$H NMR (400 MHz, DMSO-d6) δ ppm 2.35 (s, 6H) 4.63 (s, 2H) 6.87 (m, 2H) 7.30 (t, J=8.19 Hz, 1H) 7.41 (dd, J=7.80, 1.56 Hz, 1H) 7.49 (dd, J=9.36, 1.56 Hz, 1H) 10.44 (s, 1H) ESI HRMS [M+NH$_4$]$^+$ for C$_{16}$H$_{14}$BrFN$_2$O$_2$S found 416.0266.

N-[4-Cyano-3-(trifluoromethyl)phenyl]-1-(4-nitrophenyl)methanesulfonamide (Q5)

$^1$H NMR (400 MHz, DMSO-d6) δ ppm 4.94 (s, 2H) 7.39-7.47 (m, 2H) 7.51-7.59 (m, 2H) 8.02 (d, J=8.58 Hz, 1H) 8.10-8.18 (m, 2H) 10.97 (s, 1H) ESI HRMS [M+NH$_4$]$^+$ for C$_{15}$H$_{10}$F$_3$N$_3$O$_4$S found 403.0688.

1-(4-Aminophenyl)-N-[4-cyano-3-(trifluoromethyl)phenyl]methanesulfonamide (Q6)

$^1$H NMR (400 MHz, DMSO-d6) δ ppm 4.41 (s, 2H) 6.40 (d, J=8.58 Hz, 2H) 6.83 (d, J=8.58 Hz, 2H) 7.33-7.49 (m, 2H) 7.96 (d, J=8.58 Hz, 1H) ESI HRMS [M+NH$_4$]$^+$ for C$_{15}$H$_{12}$F$_3$N$_3$O$_2$S found 373.0946.

1-(4-Bromophenyl)-N-[4-cyano-3-(trifluoromethyl)phenyl]methanesulfonamide (Q7)

$^1$H NMR (400 MHz, DMSO-d6) δ ppm 4.71 (s, 2H) 7.16-7.26 (m, 2H) 7.37-7.51 (m, 4H) 7.99 (d, J=7.80 Hz, 1H) 10.85 (s, 1H) ESI HRMS [M+NH$_4$]$^+$ for C$_{15}$H$_{10}$BrF$_3$N$_2$O$_2$S found 437.9921.

N-[4-Cyano-3-(trifluoromethyl)phenyl]-1-[4-(trifluoromethyl)phenyl]methanesulfonamide (Q9)

$^1$H NMR (400 MHz, DMSO-d6) δ ppm 4.87 (s, 2H) 7.37-7.44 (m, 2H) 7.49 (m, J=8.58 Hz, 2H) 7.63 (m, J=7.80 Hz, 2H) 7.97 (d, J=8.58 Hz, 1H) 10.91 (s, 1H) ESI HRMS [M+NH$_4$]$^+$ for C$_{16}$H$_{10}$F$_6$N$_2$O$_2$S found 426.0710.

N-[4-{[(4-Methylbenzyl)sulfonyl]amino}-2-(trifluoromethyl)phenyl]acetamide (Q10)

$^1$H NMR (400 MHz, DMSO-d6) δ ppm 2.03 (s, 3H) 2.25 (s, 3H) 4.47 (s, 2H) 7.06-7.18 (m, 4H) 7.28-7.34 (m, 3H) 9.42 (br. s., 1H) 10.10 (s, 1H) ESI HRMS [M+NH$_4$]$^+$ for C$_{17}$H$_{17}$F$_3$N$_2$O$_3$S found 404.1255.

N-[4-{[(4-Methylbenzyl)sulfonyl]amino}-2-(trifluoromethyl)phenyl]-N-propylacetamide (Q11)

$^1$H NMR (400 MHz, DMSO-d6) δ ppm 0.83 (t, J=7.41 Hz, 3H) 1.41-1.55 (m, 2H) 1.80 (s, 3H) 2.31 (s, 3H) 3.10 (q, J=6.24 Hz, 2H) 4.93 (s, 2H) 5.69 (s, 1H) 6.12 (d, J=2.34 Hz, 1H) 6.67 (d, J=9.36 Hz, 1H) 6.93 (dd, J=8.58, 2.34 Hz, 1H) 7.18-7.25 (m, 4H) ESI HRMS [M+NH$_4$]$^+$ for C$_{20}$H$_{23}$F$_3$N$_2$O$_3$S found 446.1725.

N-(4-Cyano-3-methylphenyl)-1-[4-(trifluoromethyl)phenyl]methanesulfonamide (Q13)

$^1$H NMR (400 MHz, DMSO-d6) δ ppm 2.36 (s, 3H) 4.75 (s, 2H) 7.00-7.10 (m, 2H) 7.46 (d, J=7.80 Hz, 2H) 7.58-7.72 (m, 3H) 10.41 (s, 1H) ESI HRMS [M+NH$_4$]$^+$ for C$_{16}$H$_{13}$F$_3$N$_2$O$_2$S found 372.0993.

N-[2-Amino-4-cyano-5-(trifluoromethyl)phenyl]-1-(4-methylphenyl)methanesulfonamide (Q18)

$^1$H NMR (400 MHz, DMSO-d6) δ ppm 2.23 (s, 3H) 4.46 (s, 2H) 6.18 (br. s., 2H) 7.07 (d, J=7.80 Hz, 2H) 7.12-7.22 (m, 3H) 7.30 (s, 1H) 9.30 (br. s., 1H) ESI HRMS [M+NH$_4$]$^+$ for C$_{16}$H$_{14}$F$_3$N$_3$O$_2$S found 387.1102.

N-[4-Cyano-2-nitro-5-(trifluoromethyl)phenyl]-1-(4-methylphenyl)methanesulfonamide (Q17)

$^1$H NMR (400 MHz, DMSO-d6) δ ppm 2.16 (s, 3H) 4.66 (s, 2H) 7.01 (d, J=7.80 Hz, 2H) 7.16-7.24 (m, 2H) 7.36 (s, 1H) 8.60 (s, 1H) ESI HRMS [M+NH$_4$]$^+$ for C$_{16}$H$_{12}$F$_3$N$_3$O$_4$S found 417.0844.

4-Amino-2-ethyl-6-methylbenzonitrile (17)

$^1$H NMR (400 MHz, DMSO-d6) δ ppm 1.12 (t, J=8.0 Hz, 3H) 2.24 (s, 3H) 2.55 (q, J=7.28 Hz, 2H) 5.91 (s, 2H) 6.30 (m, 2H).

4-Amino-2-methyl-6-propylbenzonitrile (18)

$^1$H NMR (400 MHz, DMSO-d6) δ ppm 0.87 (t, J=8.0 Hz, 3H) 1.49-1.59 (m, 2H) 2.24 (s, 3H) 2.51 (d, J=7.80 Hz, 2H) 5.90 (s, 2H) 6.24-6.33 (m, 2H).

4-Amino-2-cyclopropyl-6-methylbenzonitrile (19)

$^1$H NMR (400 MHz, DMSO-d6) δ ppm 0.54-0.63 (m, 2H) 0.90-1.01 (m, 2H) 1.92-2.01 (m, 1H) 2.24 (s, 3H) 5.84 (s, 2H) 5.94 (d, J=1.56 Hz, 1H) 6.26 (d, J=1.56 Hz, 1H).

4-Amino-2-propylbenzonitrile (12)

$^1$H NMR (400 MHz, DMSO-d6) δ ppm 0.87 (t, J=7.41 Hz, 3H) 1.55 (m, 2H) 2.52 (t, J=7.80 Hz, 2H) 6.00 (br. s., 2H) 6.39-6.48 (m, 2H) 7.24-7.32 (m, 1H).

1-(4-Methylphenyl)-N-[4-nitro-3-(trifluoromethyl)phenyl]methanesulfonamide (21)

$^1$H NMR (400 MHz, DMSO-d6) δ ppm 2.21 (s, 3H) 4.64 (s, 2H) 7.05 (m, J=7.80 Hz, 2H) 7.13 (m, J=7.80 Hz, 2H) 7.35-7.47 (m, 2H) 8.06 (d, J=8.58 Hz, 1H) 10.82 (s, 1H).

N-[4-Amino-3-(trifluoromethyl)phenyl]-1-(4-methylphenyl)methanesulfonamide (22)

$^1$H NMR (400 MHz, DMSO-d6) δ ppm 2.26 (s, 3H) 4.25 (s, 2H) 5.46 (s, 2H) 6.77 (d, J=9.36 Hz, 1H) 7.02-7.16 (m, 6H) 9.31 (s, 1H).

1-(4-Methylphenyl)-N-[4-(propylamino)-3-(trifluoromethyl)phenyl]methanesulfonamide (23)

¹H NMR (400 MHz, DMSO-d6) δ ppm 0.87 (t, J=7.41 Hz, 3H) 1.43-1.61 (m, 2H) 2.26 (s, 3H) 3.09 (q, J=6.76 Hz, 2H) 4.25 (s, 2H) 5.19 (t, J=5.46 Hz, 1H) 6.75 (d, J=9.36 Hz, 1H) 7.09-7.17 (m, 5H) 7.21 (dd, J=9.36, 2.34 Hz, 1H) 9.35 (s, 1H).

2-Bromo-6-methyl-4-nitrobenzonitrile (26)

¹H NMR (400 MHz, DMSO-d6) δ ppm 2.63 (s, 3H) 8.34 (d, J=2.34 Hz, 1H) 8.45 (d, J=2.34 Hz, 1H).

Example 2: PP2C Inhibition Assays

The compounds from Example 1 were screened against PYR1 and PYL2 using recombinant receptors and PP2C using an absorbance based assay with p-nitrophenolphosphate as a substrate for the PP2C (Table 1). The newly synthesized ligands exhibited activity ranging from 48 nM to 8242 nM on PYR1 and 969 nM to 31400 nM on PYL2.

1. Abscisic acid

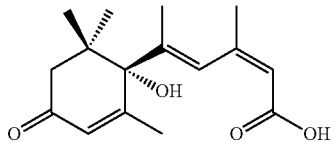

2. Pyrabactin

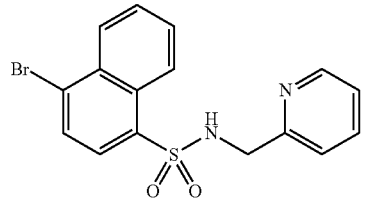

3. Quinabactin

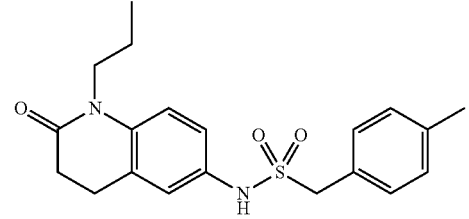

4. Q series scaffold

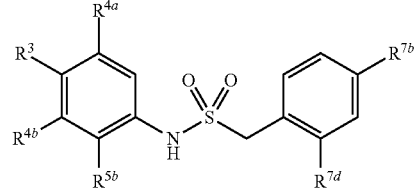

TABLE 1

IC$_{50}$s of various analogs of the Q series on the PYR1 and PYL2 receptor.

| Ligand | R$^{4a}$ | R$^{3}$ | R$^{4b}$ | R$^{5b}$ | R$^{7b}$ | R$^{7b}$ | PYR1 (nM) | PYL2 (nM) | MIC (μM) Germination | Thermal Response |
|---|---|---|---|---|---|---|---|---|---|---|
| Q1 | Me | CN | H | H | H | Me | 246 ± 60 | 20000 ± 1080 | 10 | − |
| Q2 | Cl | CN | H | H | H | Me | 3909 ± 122 | >50000 | 25 | − |
| Q3 | Br | CN | H | H | H | Me | 2504 ± 151 | >50000 | >25 | − |
| Q4 | CF$_3$ | CN | H | H | H | Me | 258 ± 19 | 9581 ± 102 | 10 | − |
| Q20 | OMe | CN | H | H | H | Me | 130 ± 9 | 11793 ± 1122 | 5 | − |
| Q26 | OEt | CN | H | H | H | Me | 112 ± 15 | 7459 ± 469 | 10 | ++ |
| Q29 | Et | CN | H | H | H | Me | 48 ± 0.3 | 2695 ± 64 | 5 | + |
| Q31 | nPr | CN | H | H | H | Me | 100 ± 0.4 | 2909 ± 270 | 10 | + |
| Q27 | Δ | CN | H | H | H | Me | 87 ± 3 | 3266 ± 13 | 5 | +++ |
| Q15 | Me | CN | Me | H | H | Me | 98 ± 7 | 2583 ± 222 | 10 | + |
| Q14 | CF$_3$ | CN | CF$_3$ | H | H | Me | >50000 | >50000 | >25 | − |
| Q25 | Br | CN | Me | H | H | Me | 355 ± 34 | 16700 ± 788 | 25 | − |
| Q30 | Me | CN | Et | H | H | Me | 72 ± 15 | 969 ± 77 | 10 | +++ |
| Q32 | Me | CN | nPr | H | H | Me | 220 ± 18 | 1605 ± 23 | 10 | + |
| Q28 | Me | CN | Δ | H | H | Me | 210 ± 36 | 1656 ± 46 | 10 | − |
| Q22 | Me | CN | Me | H | H | Cl | 197 ± 9 | 5633 ± 800 | 10 | − |
| Q23 | Me | CN | Me | H | H | Δ | 203 ± 25 | 20140 ± 1457 | 10 | − |
| Q25 | Me | CN | Me | H | F | Br | 188 ± 19 | 11853 ± 1473 | 10 | − |
| Q5 | CF$_3$ | CN | H | H | H | NO$_2$ | 8242 ± 520 | >50000 | >25 | − |
| Q6 | CF$_3$ | CN | H | H | H | NH$_2$ | 3400 ± 200 | >50000 | >25 | − |
| Q7 | CF$_3$ | CN | H | H | H | Br | 326 ± 7.7 | 31400 ± 3400 | 10 | − |
| Q9 | CF$_3$ | CN | H | H | H | CF$_3$ | 3400 ± 270 | >50000 | 10 | − |
| Q10 | CF$_3$ | NHAc | H | H | H | Me | >50000 | >50000 | >25 | − |
| Q11 | CF$_3$ | N(nPr)Ac | H | H | H | Me | >50000 | >50000 | >25 | − |
| Q13 | Me | CN | H | H | H | CF$_3$ | 1102 ± 183 | >50000 | >25 | − |
| Q17 | CF$_3$ | CN | H | NO$_2$ | H | Me | >50000 | >50000 | >25 | − |
| Q18 | CF$_3$ | CN | H | NH$_2$ | H | Me | >50000 | >50000 | >25 | − |
| ABA | — | — | — | — | — | — | 111 ± 3.8 | 39 ± 2.3 | 1 | ++ |
| QB | — | — | — | — | — | — | 85 ± 6.9 | 211 ± 41 | 3 | +++ |

MIC: Minimal Inhibitory Concentration;
NA: Not active;
QB: Quinabactin;
Δ: Cyclopropyl substituent PP2C activity assays using recombinant receptors and PP2Cs were carried out as follows: Purified proteins were pre-incubated for 30 minutes at room temperature in 160 μl assay buffer (100 mM Tris-HCl-pH 7.9, 100 mM NaCl, 3 μg bovine serum albumin, and 0.1% 2-mercaptoethanol) containing 1 mM $MnCl_2$ with quinabactin or compounds of Example 1. Reactions were started by adding 40 μL of a reaction solution containing 25 mM 4-nitrophenyl phosphate in assay buffer, after which absorbance measurements were immediately collected using a 405 nm on Wallac plate reader. Reactions contained 100 nM PP2C and 200 nM PYR/PYL proteins. For $IC_{50}$ calculation, the different concentration of quinabactin or Example 1 compound from 50 μM to 4 nM were used to measure PP2C activity. The dose response data was fitted to a log (inhibitor) vs response- (variable slope) model using non-linear regression to infer the $IC_{50}$ values using Graph Pad Prism 6.0.

Example 3: Thermal Imaging Assays

Molecules that elicit ABA-like effects in vivo typically close guard cells, which arrests transpirational water loss, resulting in less efficient cooling of the leaf surface and a concomitant increase in leaf surface temperature. Infrared thermography has recently emerged as an attractive, noninvasive technique to evaluate plant leaf surface temperature. When sprayed at 50 uM dose on adult *Arabidopsis* plants, the compounds Q26, Q27, Q30 and (to a lesser extent) Q29, Q31, and Q32 were able to increase the leaf surface temperature significantly and comparably to the changes elicited by quinabactin and ABA at the same dose (Table 1 and FIG. 1A).

For the adult plants used for thermal imaging, seeds were sterilized as described in Example 3. Afterwards, the seeds were spread onto 0.7% agar MS plant growth medium containing one-half MS salts and 0.5% sucrose. After 4 d of stratification at 4° C., these plates were transferred to a growth chamber in light and allowed to germinate and grow for 7 d. The seedlings then were transferred into soil, and plants of 3-4 wk old were used for thermal imaging. Before thermal imaging, topical spraying of the plants was performed with a water solution containing an active agent (50 μM ABA, quinabactin, or a test compound of interest), 0.5% DMSO, and 0.02% polyalkyleneoxide modified heptamethyltrisiloxane surfactant (Silwet-77). Thermal images were collected just before spraying, 24 h after treatment, and 48 h after treatment. Treated plants were compared to mock-treated plants that had been sprayed with water containing 0.5% DMSO and 0.02% Silwet-77.

Figure 1B:
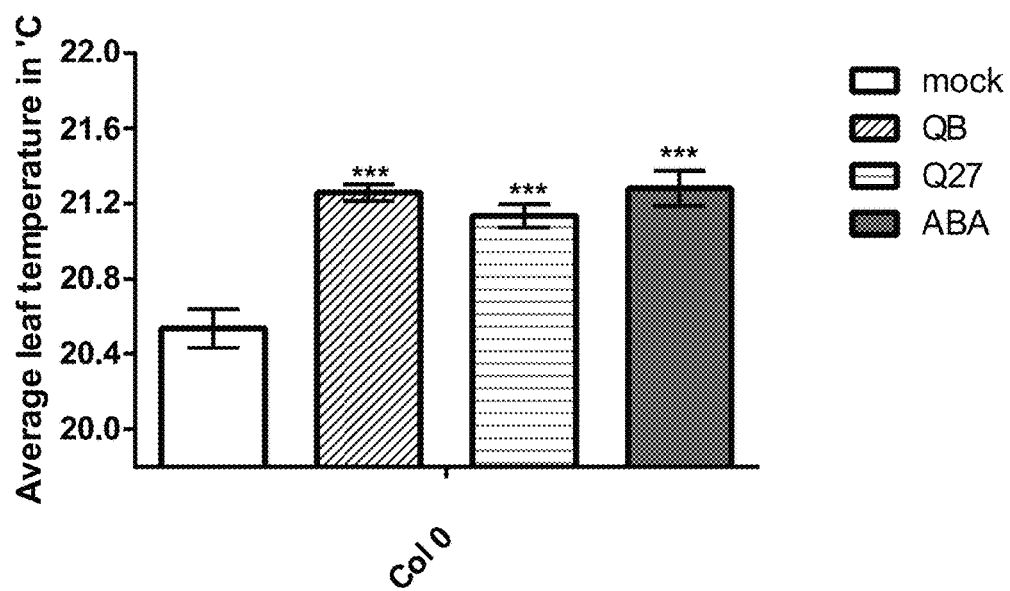

Thermal images were collected at 16 h after treatment. Thermal images were quantified using the Flir tools software version 5.2.15161.1001 by measuring the average leaf temperature of 5-6 leaves per plant. Average temperatures were calculated for 10 replicate plants (in 5 pots) per treatment. Statistical comparisons between the treated and the mock-treated plants were performed using pairwise t-tests. In the graphs represented in FIG. 1B, error bars represent the standard error of mean, asterisks symbols indicate statistical significance, and * indicates $p \leq 0.05$,  for $p \leq 0.01$, * for $p \leq 0.001$.

Example 4: pMAPKKK18::LUC+ Assays

Figure 2:
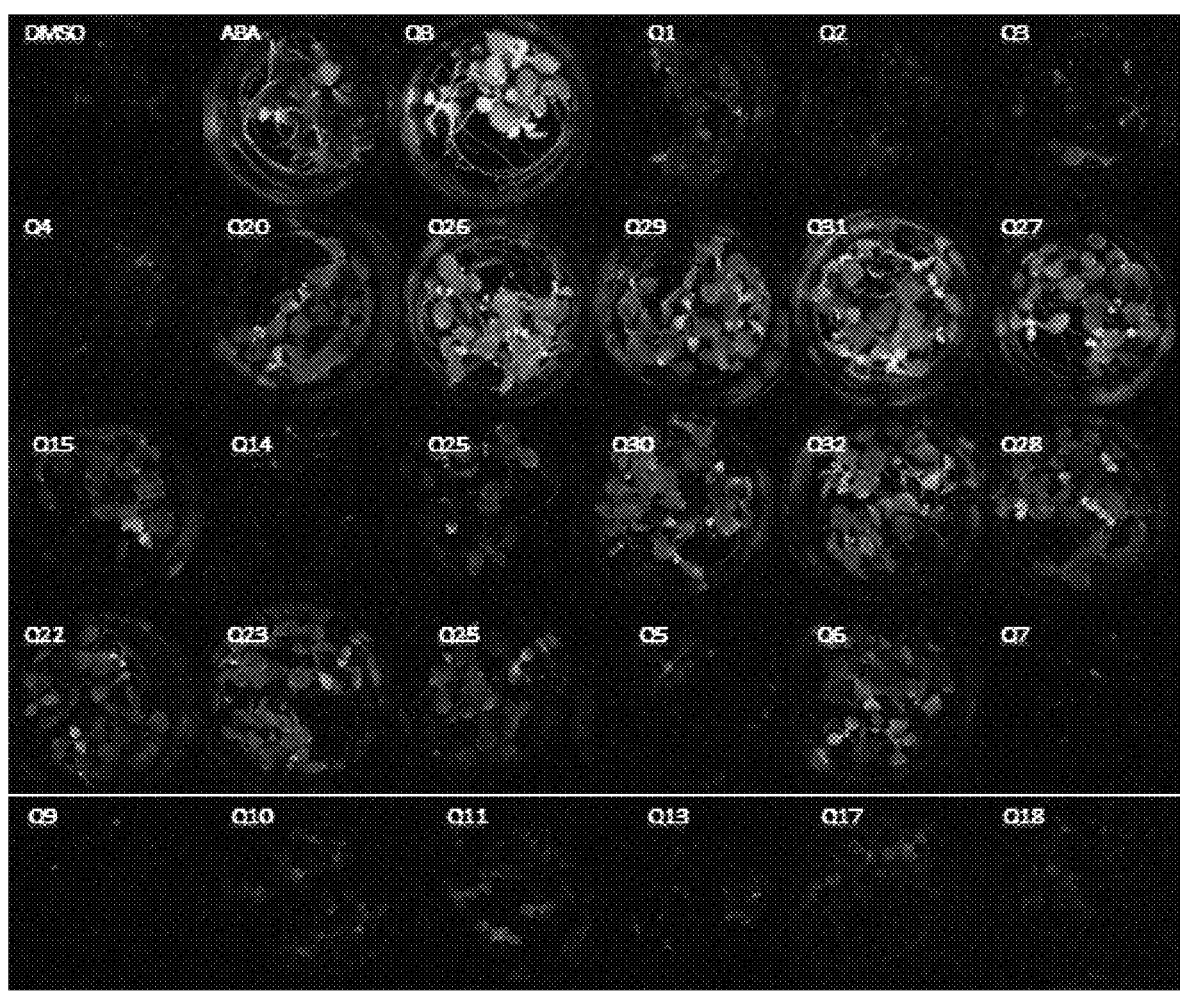
FIG. 2 shows the luciferase activity of the compounds or a solvent carrier control in MAPKKK18:luc seedlings after 6 h treatment at 25 uM dose (Example 4).

To assess the tissue-level response induced by the ligands, transgenic *Arabidopsis* plants were constructed in which an ABA responsive promoter (MAPKKK18, see Okamoto, M. et al., "Activation of Dimeric ABA Receptors Elicits Guard Cell Closure, ABA-Regulated Gene Expression, and Drought Tolerance," Proc. Natl. Acad. Sci. 2013, 110 (29), 12132-12137) drives expression of an enhanced luciferase (Luc+). Q26, Q27, and Q29-Q32 induced a significant luciferase response in the pMAPKKK18::Luc+ line, indicating the compounds activate an ABA transcriptional response (FIG. 2).

pMAPKKK18::Luc+ activity was measured with 8-d-old seedlings that had been grown in plant growth liquid medium (½ MS plant growth medium and 0.5% sucrose) under 16-h-light and 8-h-dark conditions. Seedlings were transferred to new plant growth liquid medium with the test chemical at 25 μM concentration and 100 μM luciferin. Luciferase assay image were taken at 6 h in the dark by camera (SONY α a7s) with FE1.8/55 lense (FE 55 mm F1.8 ZA; SEL55F18Z).

Example 5: Germination Assays

Germination experiments were performed with *Arabidopsis thaliana* seeds of wildtype Col0, Ler, or mutant backgrounds.

Seeds were sterilized by 30 sec incubation in 70% ethanol solution followed by a 5 min inhibition (while vigorously shaking) in a bleach-Tween solution. Afterwards, the sterilizing solutions were removed, and five washes were performed with sterile distilled water. To enhance complete removal of the solutions between the different steps, short centrifuge spins were performed. Finally, the now surface-sterilized seeds were re-suspended in an aseptic 0.1% agar solution to simplify distribution over multiwall plates. One drop of the solution contained on average 20-30 seeds.

Figure 3A:
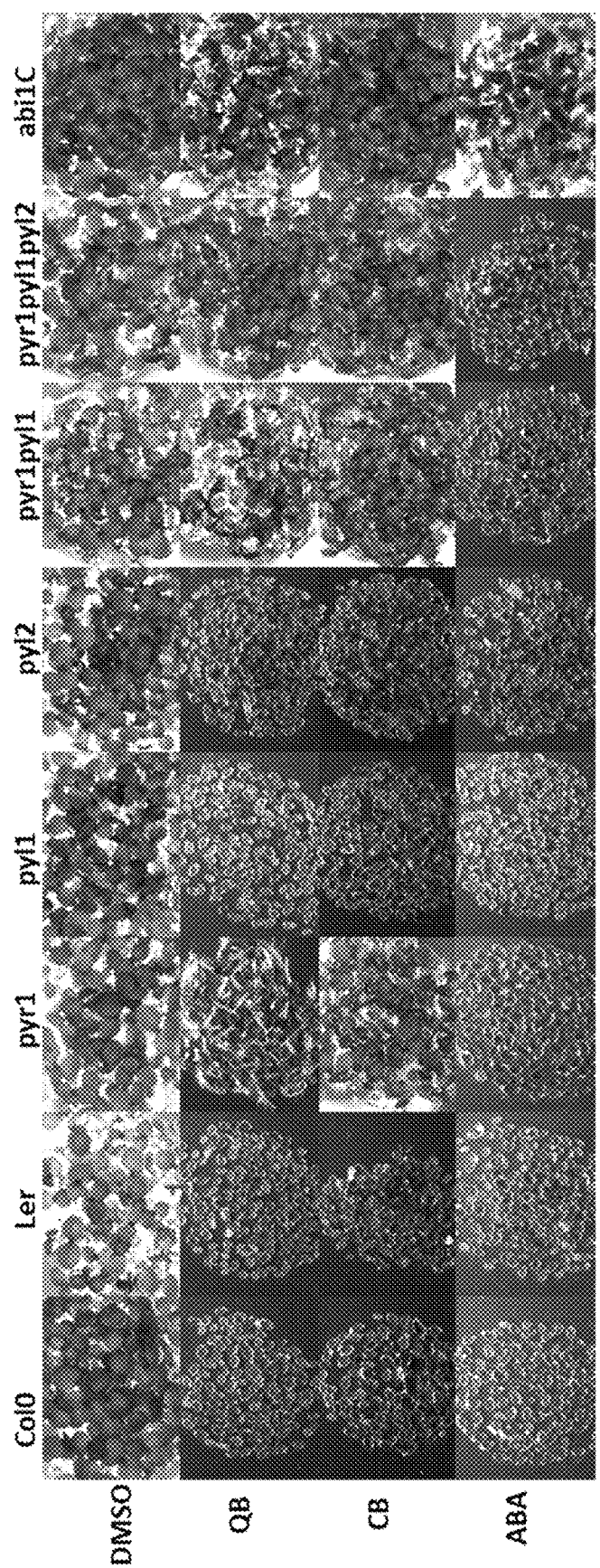
FIG. 3A and FIG. 3B show the results of a germination study (Example 5).
Figure 3B:
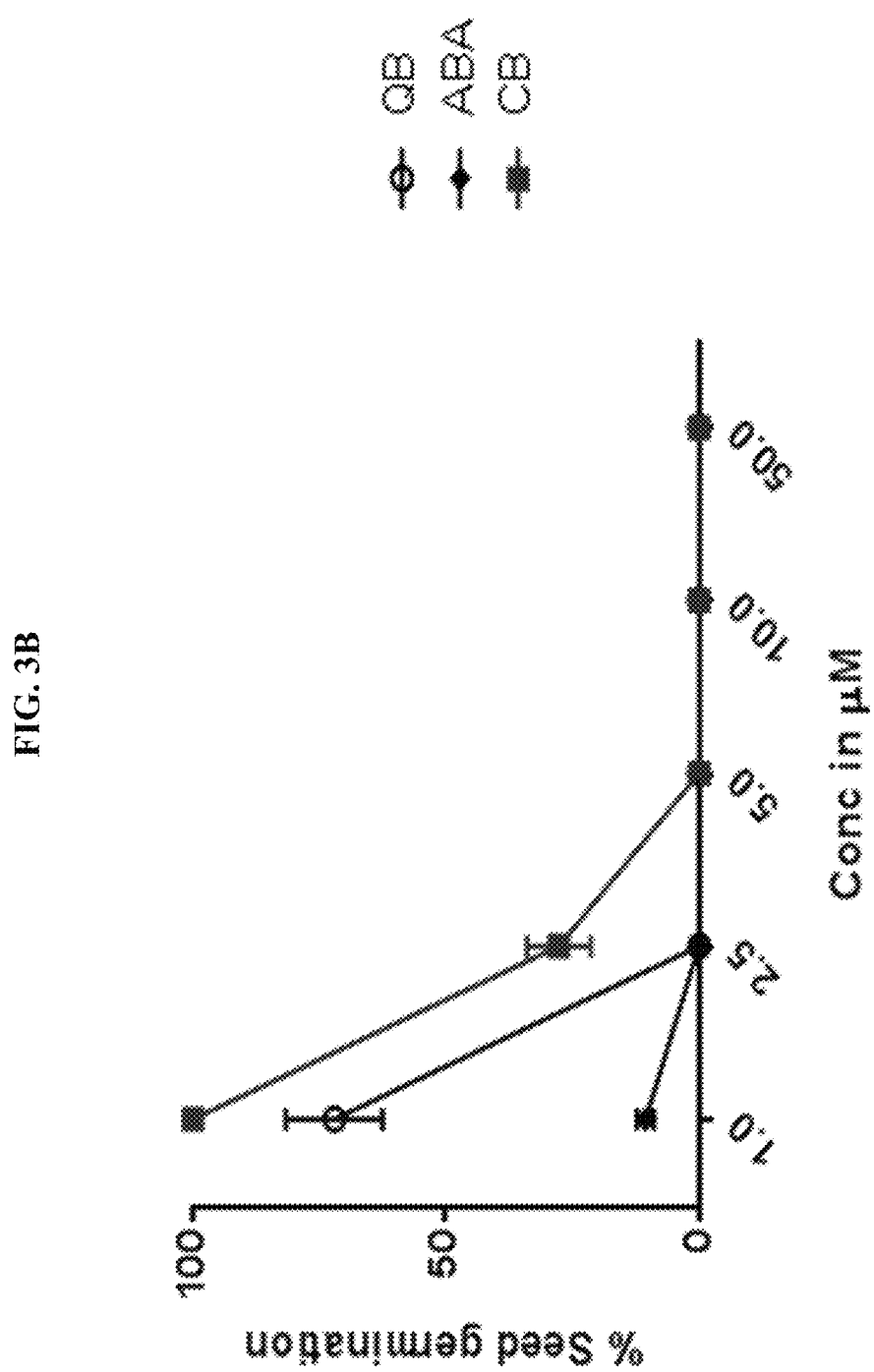

In the multiwell plates, seeds were plated onto 0.7% agar Murashige amd Skoog (MS) plant growth medium containing one-half MS salts and 0.5% sucrose containing different concentrations of ABA, quinabactin, or the compound of interest. After 4 d of stratification at 4° C., the plates were transferred to a growth chamber in darkness and allowed to germinate for 3 d before germination was evaluated. The results are shown above in Table 1 and FIGS. 3A and 3B.

Example 6: Thermodyanamic Parameters for Binding of PYR1 to Q27

Thermodyanamic parameters for binding of PYR1 to Q27 ("CB/cyanabactin") were determined using a Nano ITC Low Volume calorimeter, with the data acquisition software ITCRun v3.2 and data analysis software NanoAnalyze v3.6.

Reverse titration experiments were performed due to the low ligand solubility at 35° C. All solutions were degassed to avoid bubbles and equilibrated to the corresponding temperature for each experiment. The ligand solution in the calorimetric cell was titrated with PYR1 protein in dialysis buffer [aqueous 100 mM 3-(N-morpholino)propanesulfonic acid (MOPS), 1 mM β-mercaptoethanol, pH 7.0]. PYR1 was assayed at protein concentrations from 300-450 uM, and the Q26 ligand dissolved in dialysis buffer was assayed at concentrations between 15-30 uM. The titrations were done in a series of 20 injections of 2.5 ul each. The heat produced from each injection was acquired from the integration of the calorimetric peak. The heat due to protein-ligand binding was obtained as the difference between the heat of the reaction and the corresponding heat of dilution from buffer into Q27 ligand.

Figure 4:
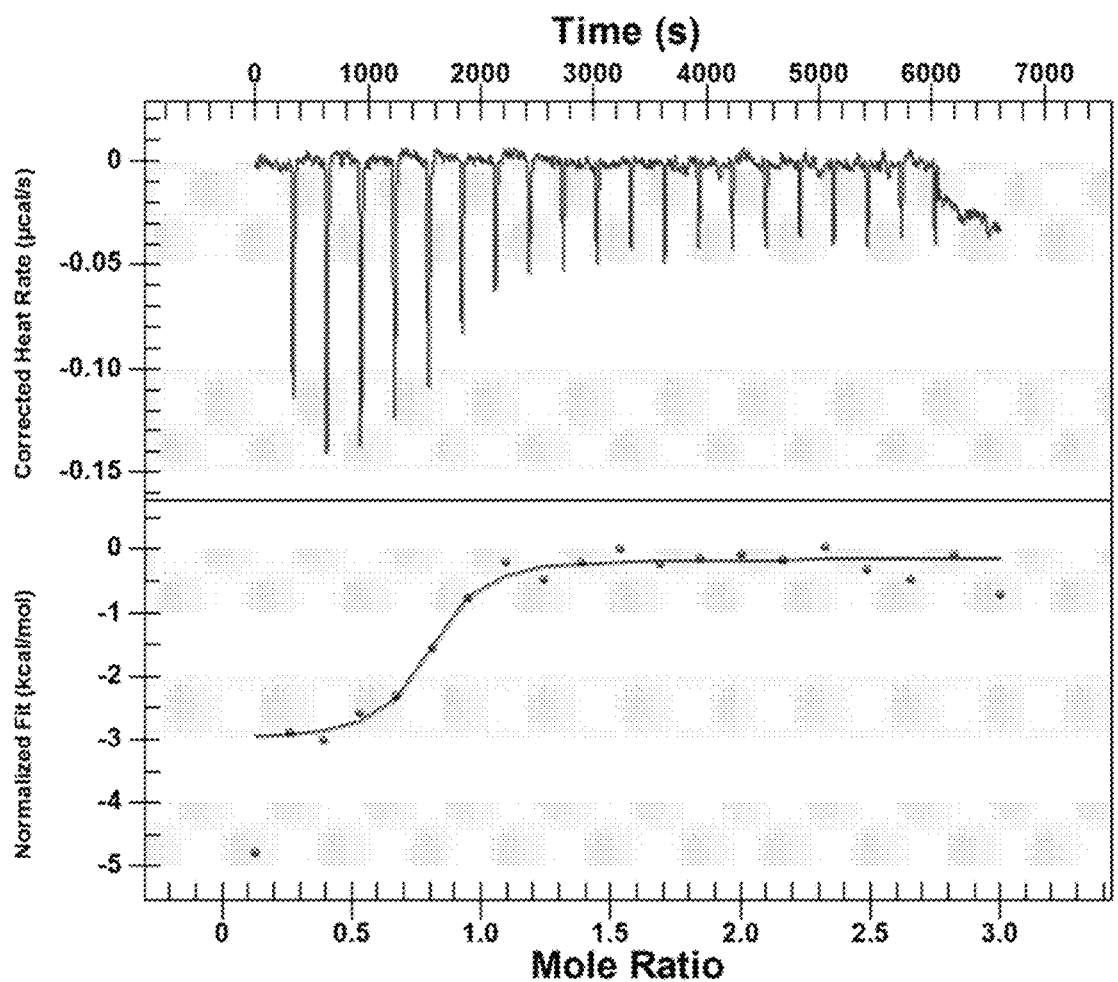
FIG. 4 shows a representative thermogram and binding curve for compound Q27 (Example 6).

The resulting binding isotherms were analyzed by blank constant fitting of the data to an independent one-site sites model with NanoAnalyze. FIG. 4 shows a representative thermogram and binding curve. Data shown are the average of three independent experiments±standard error.

Example 7: qRT-PCR Analysis of Compound Q27

To further investigate if Q27/CB, quinabactin/QB and ABA treatments induced ABA-responsive genes in vegetative tissues, qRT-PCR analysis was performed.

Figure 5:
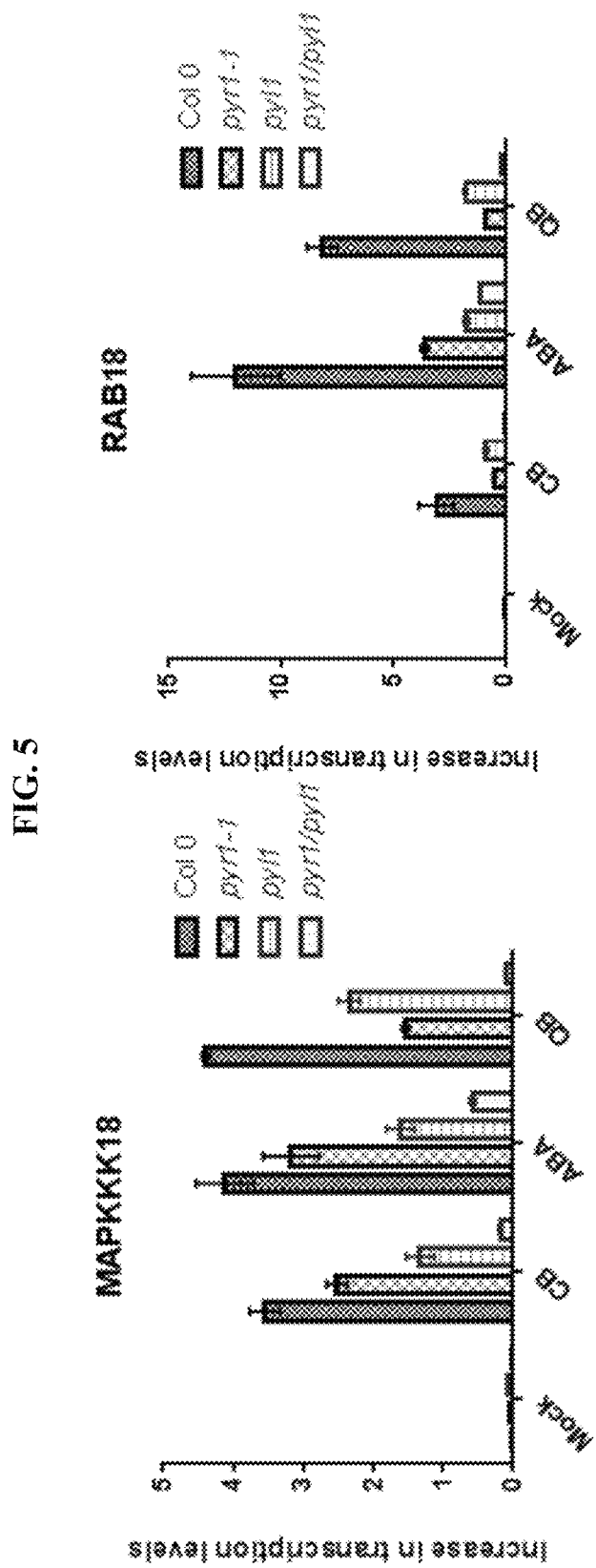
FIG. 5 shows changes in MAPKKK18 and RAB18 transcription levels following different chemical treatments in different genotypes (Example 7).

A plant RNA purification kit (Invitrogen) was used to isolate total RNA from plant tissue as per manufacturer's instructions. A QantiTec reverse transcription kit was used to synthesize cDNA from 1 μg of total RNA. Real-time PCR was performed using Maxima SYBR Green/Fluorescein qPCR Master Mix (Fermentas) with the iQ5 real-time PCR detection system. The relative amounts of target mRNAs were determined using the relative standard curve method and were normalized by relative amount of internal control mRNA. Biological triplicate experiments were performed. FIG. 5 shows changes in MAPKKK18 and RAB18 transcription levels following different chemical treatments in different genotypes.

Example 8: Binding of Cyanabactin in PYR1 and PYL2

Without intending to be bound by theory, subtle changes in the binding pockets of PYR1/PYL2 proteins can dictate the orientation of pyrabactin and contribute towards its selectivity towards PYR1 vs PYL2. In particular, a PYR1$^{I110V}$ mutant dramatically loses pyrabactin responsiveness as compared to wild-type (WT) PYR1. and the reciprocal PYL2$^{V114I}$ mutant gains pyrabactin responsiveness as compared to WT PYL2, while ABA retained responsiveness in all mutants. Cyanabactin's activity was tested with the PYR1$^{I110V}$ and the reciprocal PYL2$^{V114I}$ mutants to provide possible insights into its selectivity for PYR1 vs PYL2.

Recombinant PYR1$^{I110V}$ and PYL2$^{V114I}$ proteins were prepared using a previously described protocol previously (Peterson Peterson, F. C. et al., "Structural Basis for Selective Activation of ABA Receptors," Nat. Struct. Mol. Biol. 2010, 17 (99), 1109-1113) and tested in absorbance based phosphatase inhibition assay using p-nitrophenol phosphate as substrate as previously described.

Figure 6:
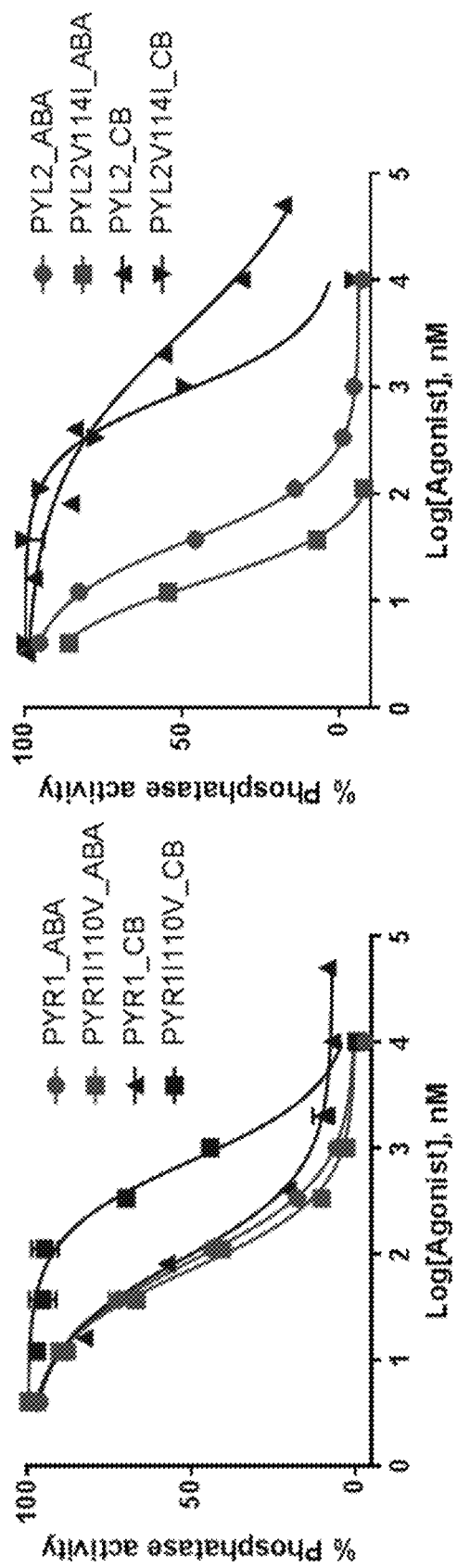
FIG. 6 shows the results of a test of Q27's activity with $PYR1^{I110V}$ and reciprocal $PYL2^{V114I}$ mutants (Example 8).

Q27 was approximately 9-fold less active in the PYR1$^{I110V}$ mutant with an IC$_{50}$ of 787 nM as compared to WT PYR1 with an IC50 of 87 nM and was 3.3-fold more active in the PYL2$^{V114I}$ mutant with an IC$_{50}$ of 981 nM as compared to 3266 nM in WT PYL2 (FIG. 6). These results suggest that Ile110 in PYR1 and Val114 residues in PYL2 were important in contributing selectivity of cyanabactin for PYR1 vs PYL2.

To further gain insights into the probable binding of cyanabactin in PYR1 and PYL2 and rationalize its apparent selectivity towards PYR1 vs PYL2, a model of cyanabactin docked to the binding site of PYR1 (PDB: 3K3K) and PYL2 (PDB: 4LA7) was prepared using Glide. For preparing crystal structures, Protein Preparation Wizard (Schrödinger Release 2015-1: Schrödinger Suite 2015-1 Protein Prepara-tion Wizard; Epik version 3.1; Impact version 6.6; Prime version 3.9) was used with default settings; only the gate-latch water molecule was retained. The Glide settings (Small-Molecule Drug Discovery Suite 2015-1: Glide, version 6.6) were used as default except that "Enhance planarity of conjugated pi groups" was used. The prepared crystal structures of 4LA7 and halo-3K3K (Chain B) were used for docking and posing. Docking poses and hydrogen bond calculations were performed with the UCSF Chimera package.

Cyanabactin and quinabactin had identical calculated interactions in PYR1, with the nitrile nitrogen in cyanabactin and the oxygen of the dihydroisoquinolinone ring in cyanabactin forming hydrogen bond with a water molecule within the "tryptophan lock." Additionally, hydrogen bonds were observed with Glu 94 and Lys 59 with the sulfonamide linkage in both molecules. The cyclopropyl moiety in cyanabactin and the propyl chain extended into the 3'-tunnel and formed hydrophobic interactions with Leu 87 and Phe 61 and (FIGS. 7A, 7B, and 7C). Molecular docking also revealed that unlike quinabactin, the sulfonamide NH in cyanabactin does not form a crucial hydrogen bond with Glu 98 in PYL2, which may further the rationale for selectivity of cyanabactin for PYR1 vs PYL2. (FIGS. 7D, 7E, and 7F).

Example 9: Growth Complementation and Thermal Response in ABA-Deficient Mutant

The effects of Q27, ABA and quinabactin were assessed in growth complementation and thermal response assays in ABA-deficient aba2 mutant.

For the complementation assay, wild-type and aba2 mutant of *Arabidopsis* Columbia accession were grown on plate containing 1× MS basal salt mixture, 1% sucrose and 0.4% gellan gum (Gelzan) at 22° C. under the 16/8-h light/dark cycle for 10 days after germination. Seedlings were grown on the pot containing a 1:1 ratio of peat-based, general-purpose growing medium (PRO-MIX BX (Premier)) and vermiculite at 22/18° C., 70/85% relative humidity and 14/10-h light/dark cycle into the plant growth chamber for 5 days. Then 10 mL of 25 μM chemical solutions containing 0.05% Tween-20 were sprayed against plants at daily intervals over a 3-day period five times. Three-week-old plants were photographed and the average rosette area calculated using Image J. Thermal response assays were carried out as described in Example 3. All ligands complemented growth in the aba2 mutants and induced a significant thermal response in leaves of aba2 mutants (FIGS. 8A, 8B, and 8C).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An agricultural formulation, comprising a compound of Formula I:

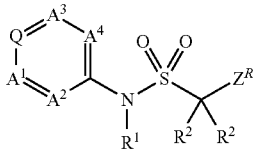

(I)

wherein
- $R^1$ is hydrogen;
- $R^2$ is selected from the group consisting of hydrogen, fluoro, cyclopropyl, and $R^6$;
- Q is $C(R^3)$;
- $A^1$ and $A^3$ are independently selected from the group consisting N, C(H), and $C(R^4)$, wherein at least one member selected from the group consisting of $A^1$ and $A^3$ is $C(R^4)$;
- $A^2$ and $A^4$ are independently selected from the group consisting of N and $C(R^5)$;
wherein at most two members selected from the group consisting of $A^1$, $A^2$, $A^3$, and $A^4$ are N;
- $R^3$ is cyano;
- each $R^4$ is independently selected from the group consisting of halo, $C_{1-3}$ alkyl, $C_{1-3}$ haloalkyl, cyclopropyl, $-OR^6$, $-SR^6$, and $-N(R^6)_2$;
- each $R^5$ is selected from the group consisting of hydrogen, halo, $C_{1-3}$ alkyl, $C_{1-3}$ haloalkyl, $C_{3-7}$ cycloalkyl, $C_{1-6}$ hydroxyalkyl, nitro, $-OR^1$, $-SR^1$, and $-N(R^1)_2$;
- each $R^6$ is independently selected from the group consisting of $C_{1-2}$ alkyl, $C_{1-2}$ haloalkyl, $C_{2-3}$ alkenyl, and $C_{2-3}$ alkynyl;
- $Z^R$ is a second ring that is selected from the group consisting of phenyl, naphthyl, pyridyl, pyrazinyl, pyrimidinyl, pyridazinyl, pyrrolyl, pyrazolyl, thiophenyl, and thiazolyl;
wherein the second ring has from 0 to 5 $R^5$ substituents;
or a salt or isomer thereof.

2. The agricultural formulation of claim 1, wherein $Z^R$ is phenyl.

3. The agricultural formulation of claim 1, wherein at most one member selected from the group consisting of $A^1$, $A^2$, $A^3$, and $A^4$ is N.

4. The agricultural formulation of claim 1, wherein the compound of Formula I is a compound of Formula II:

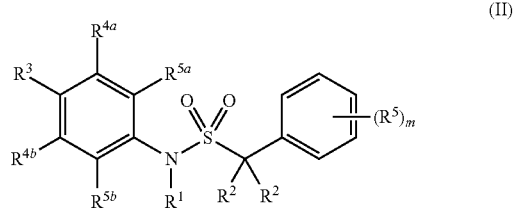

(II)

wherein
- $R^{4a}$ and $R^{4b}$ are each independently selected from the group consisting of hydrogen, halo, $C_{1-3}$ alkyl, $C_{1-3}$ haloalkyl, and cyclopropyl; wherein at least one of the $R^{4a}$ and the $R^{4b}$ is not hydrogen;
- $R^{5a}$ and $R^{5b}$ are each independently selected from the group consisting of hydrogen, halo, methyl, ethyl, trifluoromethyl, nitro, methoxy, ethoxy, and amino;
- m is an integer from 0 to 4;
or a salt or isomer thereof.

5. The agricultural formulation of claim 1, wherein no more than one ring substituent ortho- to $R^3$ is halo or haloalkyl.

6. The agricultural formulation of claim 1, wherein no more than one ring substituent is halo, haloalkyl, nitro, or —$SR^1$.

7. The agricultural formulation of 1, wherein at least one ring substituent ortho- to $R^3$ is methyl.

8. The agricultural formulation of 1, wherein the compound of Formula I is a compound of Formula III:

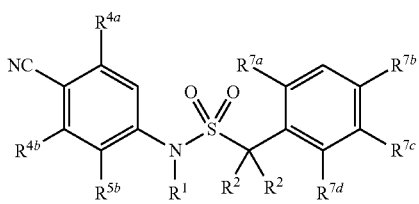

(III)

wherein
- $R^{4a}$ and $R^{4b}$ are each independently selected from the group consisting of hydrogen, halo, $C_{1-3}$ alkyl, $C_{1-3}$ haloalkyl, and cyclopropyl; wherein at least one of the $R^{4a}$ and the $R^{4b}$ is not hydrogen;
- $R^{5b}$ is selected from the group consisting of hydrogen, halo, methyl, ethyl, trifluoromethyl, nitro, methoxy, ethoxy, and amino;
- $R^{7a}$, $R^{7b}$, $R^{7c}$, and $R^{7d}$ are each independently selected from the group consisting of hydrogen, halo, $C_{1-3}$ alkyl, trifluoromethyl, cyclopropyl, nitro, —$OR^1$, and —$N(R^1)_2$;

or a salt or isomer thereof.

9. The agricultural formulation of claim 1, wherein $R^{5b}$ is hydrogen.

10. The agricultural formulation of claim 1, wherein $R^{7c}$ and $R^{7d}$ are hydrogen.

11. The agricultural formulation of claim 1, wherein $R^{7a}$ and $R^{7b}$ are each independently selected from the group consisting of halo, nitro, $C_{1-3}$ alkyl, cyclopropyl, —$OR^6$, and —$N(R^6)_2$.

12. The agricultural formulation of claim 1, wherein $R^{7a}$ is hydrogen or halo.

13. The agricultural formulation of claim 1, wherein $R^{7b}$ is $C_{1-3}$ alkyl.

14. The agricultural formulation of claim 13, wherein $R^{7b}$ is methyl.

15. The agricultural formulation of claim 1, wherein each ring substituent ortho- to $R^3$ is selected independently from the group consisting of methyl, ethyl, n-propyl, chloro, bromo, trifluoromethyl, methoxy, and ethoxy.

16. The agricultural formulation of claim 1, wherein each ring substituent meta- to $R^3$ is selected independently from the group consisting of hydrogen, nitro, and —$N(R^6)_2$.

17. The agricultural formulation of claim 1, further comprising at least one of a fungicide, an herbicide, a pesticide, a nematicide, an insecticide, a plant activator, an herbicide safener, a plant growth regulator, an insect repellant, an acaricide, a molluscicide, or a fertilizer.

18. The agricultural formulation of claim 1, further comprising a surfactant.

19. The agricultural formulation of claim 1, further comprising a carrier.

20. A method of increasing drought tolerance in a plant, the method comprising contacting a plant with a sufficient amount of the agricultural formulation according to claim 1, thereby increasing drought tolerance in the plant compared to not contacting the plant with the formulation.

21. A method of bringing a plant in contact with an agricultural formulation, comprising contacting the plant with the agricultural formulation of claim 1.

* * * * *

SEQUENCE LISTING

<160> NUMBER OF SEQ ID NOS: 119

<210> SEQ ID NO 1
<211> LENGTH: 191
<212> TYPE: PRT
<213> ORGANISM: Arabidopsis thaliana
<220> FEATURE:
<223> OTHER INFORMATION: thale cress PYR/PYL receptor, Pyrabactin
      resistance 1, abscisic acid receptor PYR1 (PYR1), ABI1-binding
      protein 6 (ABIP6), regulatory components of ABA receptor 11
      (RCAR11), At4g17870, T6K21.50

<400> SEQUENCE: 1

Met Pro Ser Glu Leu Thr Pro Glu Glu Arg Ser Glu Leu Lys Asn Ser
1               5                   10                  15

Ile Ala Glu Phe His Thr Tyr Gln Leu Asp Pro Gly Ser Cys Ser Ser
            20                  25                  30

Leu His Ala Gln Arg Ile His Ala Pro Pro Glu Leu Val Trp Ser Ile
        35                  40                  45

Val Arg Arg Phe Asp Lys Pro Gln Thr Tyr Lys His Phe Ile Lys Ser
    50                  55                  60

Cys Ser Val Glu Gln Asn Phe Glu Met Arg Val Gly Cys Thr Arg Asp
65                  70                  75                  80

Val Ile Val Ile Ser Gly Leu Pro Ala Asn Thr Ser Thr Glu Arg Leu
                85                  90                  95

Asp Ile Leu Asp Asp Glu Arg Arg Val Thr Gly Phe Ser Ile Ile Gly
            100                 105                 110

Gly Glu His Arg Leu Thr Asn Tyr Lys Ser Val Thr Thr Val His Arg
        115                 120                 125

Phe Glu Lys Glu Asn Arg Ile Trp Thr Val Val Leu Glu Ser Tyr Val
    130                 135                 140

Val Asp Met Pro Glu Gly Asn Ser Glu Asp Asp Thr Arg Met Phe Ala
145                 150                 155                 160

Asp Thr Val Val Lys Leu Asn Leu Gln Lys Leu Ala Thr Val Ala Glu
                165                 170                 175

Ala Met Ala Arg Asn Ser Gly Asp Gly Ser Gly Ser Gln Val Thr
            180                 185                 190

<210> SEQ ID NO 2
<211> LENGTH: 221
<212> TYPE: PRT
<213> ORGANISM: Arabidopsis thaliana
<220> FEATURE:
<223> OTHER INFORMATION: thale cress PYR/PYL receptor, abscisic acid
      receptor PYL1, PYR1-like protein 1 (PYL1), ABI1-binding protein 6
      (ABIP6), regulatory components of ABA receptor 9 (RCAR12),
      At5g46790, MZA15.21

<400> SEQUENCE: 2

Met Ala Asn Ser Glu Ser Ser Ser Ser Pro Val Asn Glu Glu Glu Asn
1               5                   10                  15

Ser Gln Arg Ile Ser Thr Leu His His Gln Thr Met Pro Ser Asp Leu
            20                  25                  30

Thr Gln Asp Glu Phe Thr Gln Leu Ser Gln Ser Ile Ala Glu Phe His
        35                  40                  45

Thr Tyr Gln Leu Gly Asn Gly Arg Cys Ser Ser Leu Leu Ala Gln Arg
    50                  55                  60

Ile His Ala Pro Pro Glu Thr Val Trp Ser Val Val Arg Arg Phe Asp
65                  70                  75                  80

```
Arg Pro Gln Ile Tyr Lys His Phe Ile Lys Ser Cys Asn Val Ser Glu
                85                  90                  95

Asp Phe Glu Met Arg Val Gly Cys Thr Arg Asp Val Asn Val Ile Ser
            100                 105                 110

Gly Leu Pro Ala Asn Thr Ser Arg Glu Arg Leu Asp Leu Leu Asp Asp
        115                 120                 125

Asp Arg Arg Val Thr Gly Phe Ser Ile Thr Gly Gly Glu His Arg Leu
    130                 135                 140

Arg Asn Tyr Lys Ser Val Thr Thr Val His Arg Phe Glu Lys Glu Glu
145                 150                 155                 160

Glu Glu Glu Arg Ile Trp Thr Val Val Leu Glu Ser Tyr Val Val Asp
                165                 170                 175

Val Pro Glu Gly Asn Ser Glu Glu Asp Thr Arg Leu Phe Ala Asp Thr
            180                 185                 190

Val Ile Arg Leu Asn Leu Gln Lys Leu Ala Ser Ile Thr Glu Ala Met
        195                 200                 205

Asn Arg Asn Asn Asn Asn Asn Ser Ser Gln Val Arg
    210                 215                 220

<210> SEQ ID NO 3
<211> LENGTH: 190
<212> TYPE: PRT
<213> ORGANISM: Arabidopsis thaliana
<220> FEATURE:
<223> OTHER INFORMATION: thale cress PYR/PYL receptor, abscisic acid
      receptor PYL2, PYR1-like protein 2 (PYL2), ABI1-binding protein 6
      (ABIP6), regulatory components of ABA receptor 14 (RCAR14), Bet v
      I allergen family protein, At2g26040, T19L18.15

<400> SEQUENCE: 3

Met Ser Ser Ser Pro Ala Val Lys Gly Leu Thr Asp Glu Glu Gln Lys
1               5                   10                  15

Thr Leu Glu Pro Val Ile Lys Thr Tyr His Gln Phe Glu Pro Asp Pro
            20                  25                  30

Thr Thr Cys Thr Ser Leu Ile Thr Gln Arg Ile His Ala Pro Ala Ser
        35                  40                  45

Val Val Trp Pro Leu Ile Arg Arg Phe Asp Asn Pro Glu Arg Tyr Lys
    50                  55                  60

His Phe Val Lys Arg Cys Arg Leu Ile Ser Gly Asp Gly Asp Val Gly
65                  70                  75                  80

Ser Val Arg Glu Val Thr Val Ile Ser Gly Leu Pro Ala Ser Thr Ser
                85                  90                  95

Thr Glu Arg Leu Glu Phe Val Asp Asp Asp His Arg Val Leu Ser Phe
            100                 105                 110

Arg Val Val Gly Gly Glu His Arg Leu Lys Asn Tyr Lys Ser Val Thr
        115                 120                 125

Ser Val Asn Glu Phe Leu Asn Gln Asp Ser Gly Lys Val Tyr Thr Val
    130                 135                 140

Val Leu Glu Ser Tyr Thr Val Asp Ile Pro Glu Gly Asn Thr Glu Glu
145                 150                 155                 160

Asp Thr Lys Met Phe Val Asp Thr Val Val Lys Leu Asn Leu Gln Lys
                165                 170                 175

Leu Gly Val Ala Ala Thr Ser Ala Pro Met His Asp Asp Glu
            180                 185                 190

<210> SEQ ID NO 4
<211> LENGTH: 209
```

```
<212> TYPE: PRT
<213> ORGANISM: Arabidopsis thaliana
<220> FEATURE:
<223> OTHER INFORMATION: thale cress PYR/PYL receptor, abscisic acid
      receptor PYL3, PYR1-like protein 3 (PYL3), regulatory components
      of ABA receptor 13 (RCAR13), At1g73000, F3N23.20

<400> SEQUENCE: 4

Met Asn Leu Ala Pro Ile His Asp Pro Ser Ser Ser Thr Thr Thr
1               5                   10                  15

Thr Ser Ser Ser Thr Pro Tyr Gly Leu Thr Lys Asp Glu Phe Ser Thr
                20                  25                  30

Leu Asp Ser Ile Ile Arg Thr His His Thr Phe Pro Arg Ser Pro Asn
                35                  40                  45

Thr Cys Thr Ser Leu Ile Ala His Arg Val Asp Ala Pro Ala His Ala
    50                  55                  60

Ile Trp Arg Phe Val Arg Asp Phe Ala Asn Pro Asn Lys Tyr Lys His
65                  70                  75                  80

Phe Ile Lys Ser Cys Thr Ile Arg Val Asn Gly Asn Gly Ile Lys Glu
                85                  90                  95

Ile Lys Val Gly Thr Ile Arg Glu Val Ser Val Val Ser Gly Leu Pro
                100                 105                 110

Ala Ser Thr Ser Val Glu Ile Leu Glu Val Leu Asp Glu Glu Lys Arg
                115                 120                 125

Ile Leu Ser Phe Arg Val Leu Gly Gly Glu His Arg Leu Asn Asn Tyr
                130                 135                 140

Arg Ser Val Thr Ser Val Asn Glu Phe Val Val Leu Glu Lys Asp Lys
145                 150                 155                 160

Lys Lys Arg Val Tyr Ser Val Val Leu Glu Ser Tyr Ile Val Asp Ile
                165                 170                 175

Pro Gln Gly Asn Thr Glu Glu Asp Thr Arg Met Phe Val Asp Thr Val
                180                 185                 190

Val Lys Ser Asn Leu Gln Asn Leu Ala Val Ile Ser Thr Ala Ser Pro
                195                 200                 205

Thr

<210> SEQ ID NO 5
<211> LENGTH: 207
<212> TYPE: PRT
<213> ORGANISM: Arabidopsis thaliana
<220> FEATURE:
<223> OTHER INFORMATION: thale cress PYR/PYL receptor, abscisic acid
      receptor PYL4, PYR1-like protein 4 (PYL4), ABI1-binding protein 2
      (ABIP2), regulatory components of ABA receptor 10 (RCAR10),
      At2g38310, T19C21.20

<400> SEQUENCE: 5

Met Leu Ala Val His Arg Pro Ser Ser Ala Val Ser Asp Gly Asp Ser
1               5                   10                  15

Val Gln Ile Pro Met Met Ile Ala Ser Phe Gln Lys Arg Phe Pro Ser
                20                  25                  30

Leu Ser Arg Asp Ser Thr Ala Ala Arg Phe His Thr His Glu Val Gly
                35                  40                  45

Pro Asn Gln Cys Cys Ser Ala Val Ile Gln Glu Ile Ser Ala Pro Ile
    50                  55                  60

Ser Thr Val Trp Ser Val Val Arg Arg Phe Asp Asn Pro Gln Ala Tyr
65                  70                  75                  80

Lys His Phe Leu Lys Ser Cys Ser Val Ile Gly Gly Asp Gly Asp Asn
```

```
                85                  90                  95
Val Gly Ser Leu Arg Gln Val His Val Val Ser Gly Leu Pro Ala Ala
            100                 105                 110

Ser Ser Thr Glu Arg Leu Asp Ile Leu Asp Asp Glu Arg His Val Ile
            115                 120                 125

Ser Phe Ser Val Val Gly Asp His Arg Leu Ser Asn Tyr Arg Ser
        130                 135                 140

Val Thr Thr Leu His Pro Ser Pro Ile Ser Gly Thr Val Val Val Glu
145                 150                 155                 160

Ser Tyr Val Val Asp Val Pro Pro Gly Asn Thr Lys Glu Glu Thr Cys
                165                 170                 175

Asp Phe Val Asp Val Ile Val Arg Cys Asn Leu Gln Ser Leu Ala Lys
            180                 185                 190

Ile Ala Glu Asn Thr Ala Ala Glu Ser Lys Lys Lys Met Ser Leu
            195                 200                 205

<210> SEQ ID NO 6
<211> LENGTH: 203
<212> TYPE: PRT
<213> ORGANISM: Arabidopsis thaliana
<220> FEATURE:
<223> OTHER INFORMATION: thale cress PYR/PYL receptor, abscisic acid
      receptor PYL5, PYR1-like protein 5 (PYL5), ABI1-binding protein 3
      (ABIP3), regulatory components of ABA receptor 8 (RCAR8), Bet v I
      allergen family protein, At5g05440, K18I23.25

<400> SEQUENCE: 6

Met Arg Ser Pro Val Gln Leu Gln His Gly Ser Asp Ala Thr Asn Gly
1               5                   10                  15

Phe His Thr Leu Gln Pro His Asp Gln Thr Asp Gly Pro Ile Lys Arg
            20                  25                  30

Val Cys Leu Thr Arg Gly Met His Val Pro Glu His Val Ala Met His
        35                  40                  45

His Thr His Asp Val Gly Pro Asp Gln Cys Cys Ser Ser Val Val Gln
    50                  55                  60

Met Ile His Ala Pro Pro Glu Ser Val Trp Ala Leu Val Arg Arg Phe
65                  70                  75                  80

Asp Asn Pro Lys Val Tyr Lys Asn Phe Ile Arg Gln Cys Arg Ile Val
                85                  90                  95

Gln Gly Asp Gly Leu His Val Gly Asp Leu Arg Glu Val Met Val Val
            100                 105                 110

Ser Gly Leu Pro Ala Val Ser Ser Thr Glu Arg Leu Glu Ile Leu Asp
            115                 120                 125

Glu Glu Arg His Val Ile Ser Phe Ser Val Val Gly Gly Asp His Arg
        130                 135                 140

Leu Lys Asn Tyr Arg Ser Val Thr Thr Leu His Ala Ser Asp Asp Glu
145                 150                 155                 160

Gly Thr Val Val Val Glu Ser Tyr Ile Val Asp Val Pro Pro Gly Asn
                165                 170                 175

Thr Glu Glu Glu Thr Leu Ser Phe Val Asp Thr Ile Val Arg Cys Asn
            180                 185                 190

Leu Gln Ser Leu Ala Arg Ser Thr Asn Arg Gln
            195                 200

<210> SEQ ID NO 7
<211> LENGTH: 215
<212> TYPE: PRT
```

<213> ORGANISM: Arabidopsis thaliana
<220> FEATURE:
<223> OTHER INFORMATION: thale cress PYR/PYL receptor, abscisic acid
      receptor PYL6, PYR1-like protein 6 (PYL6), ABI1-binding protein 5
      (ABIP5), regulatory components of ABA receptor 9 (RCAR9), Bet v I
      allergen family protein, At2g40330, T7M7.15

<400> SEQUENCE: 7

Met Pro Thr Ser Ile Gln Phe Gln Arg Ser Ser Thr Ala Ala Glu Ala
1               5                   10                  15

Ala Asn Ala Thr Val Arg Asn Tyr Pro His His Gln Lys Gln Val
            20                  25                  30

Gln Lys Val Ser Leu Thr Arg Gly Met Ala Asp Val Pro Glu His Val
        35                  40                  45

Glu Leu Ser His Thr His Val Val Gly Pro Ser Gln Cys Phe Ser Val
    50                  55                  60

Val Val Gln Asp Val Glu Ala Pro Val Ser Thr Val Trp Ser Ile Leu
65                  70                  75                  80

Ser Arg Phe Glu His Pro Gln Ala Tyr Lys His Phe Val Lys Ser Cys
                85                  90                  95

His Val Val Ile Gly Asp Gly Arg Glu Val Gly Ser Val Arg Glu Val
            100                 105                 110

Arg Val Val Ser Gly Leu Pro Ala Ala Phe Ser Leu Glu Arg Leu Glu
        115                 120                 125

Ile Met Asp Asp Asp Arg His Val Ile Ser Phe Ser Val Val Gly Gly
    130                 135                 140

Asp His Arg Leu Met Asn Tyr Lys Ser Val Thr Thr Val His Glu Ser
145                 150                 155                 160

Glu Glu Asp Ser Asp Gly Lys Lys Arg Thr Arg Val Val Glu Ser Tyr
                165                 170                 175

Val Val Asp Val Pro Ala Gly Asn Asp Lys Glu Glu Thr Cys Ser Phe
            180                 185                 190

Ala Asp Thr Ile Val Arg Cys Asn Leu Gln Ser Leu Ala Lys Leu Ala
        195                 200                 205

Glu Asn Thr Ser Lys Phe Ser
    210                 215

<210> SEQ ID NO 8
<211> LENGTH: 211
<212> TYPE: PRT
<213> ORGANISM: Arabidopsis thaliana
<220> FEATURE:
<223> OTHER INFORMATION: thale cress PYR/PYL receptor, abscisic acid
      receptor PYL7, PYR1-like protein 7 (PYL7), ABI1-binding protein 7
      (ABIP7), regulatory components of ABA receptor 2 (RCAR2),
      At4g01026

<400> SEQUENCE: 8

Met Glu Met Ile Gly Gly Asp Asp Thr Asp Thr Glu Met Tyr Gly Ala
1               5                   10                  15

Leu Val Thr Ala Gln Ser Leu Arg Leu Arg His Leu His His Cys Arg
            20                  25                  30

Glu Asn Gln Cys Thr Ser Val Leu Val Lys Tyr Ile Gln Ala Pro Val
        35                  40                  45

His Leu Val Trp Ser Leu Val Arg Arg Phe Asp Gln Pro Gln Lys Tyr
    50                  55                  60

Lys Pro Phe Ile Ser Arg Cys Thr Val Asn Gly Asp Pro Glu Ile Gly
65                  70                  75                  80

```
Cys Leu Arg Glu Val Asn Val Lys Ser Gly Leu Pro Ala Thr Thr Ser
                 85                  90                  95

Thr Glu Arg Leu Glu Gln Leu Asp Asp Glu Glu His Ile Leu Gly Ile
            100                 105                 110

Asn Ile Ile Gly Gly Asp His Arg Leu Lys Asn Tyr Ser Ser Ile Leu
            115                 120                 125

Thr Val His Pro Glu Met Ile Asp Gly Arg Ser Gly Thr Met Val Met
        130                 135                 140

Glu Ser Phe Val Val Asp Val Pro Gln Gly Asn Thr Lys Asp Asp Thr
145                 150                 155                 160

Cys Tyr Phe Val Glu Ser Leu Ile Lys Cys Asn Leu Lys Ser Leu Ala
                165                 170                 175

Cys Val Ser Glu Arg Leu Ala Ala Gln Asp Ile Thr Asn Ser Ile Ala
            180                 185                 190

Thr Phe Cys Asn Ala Ser Asn Gly Tyr Arg Glu Lys Asn His Thr Glu
        195                 200                 205

Thr Asn Leu
    210

<210> SEQ ID NO 9
<211> LENGTH: 188
<212> TYPE: PRT
<213> ORGANISM: Arabidopsis thaliana
<220> FEATURE:
<223> OTHER INFORMATION: thale cress PYR/PYL receptor, abscisic acid
      receptor PYL8, PYR1-like protein 8 (PYL8), ABI1-binding protein 1
      (ABIP1), regulatory components of ABA receptor 3 (RCAR3),
      At5g53160, MFH8.10

<400> SEQUENCE: 9

Met Glu Ala Asn Gly Ile Glu Asn Leu Thr Asn Pro Asn Gln Glu Arg
1               5                   10                  15

Glu Phe Ile Arg Arg His His Lys His Glu Leu Val Asp Asn Gln Cys
            20                  25                  30

Ser Ser Thr Leu Val Lys His Ile Asn Ala Pro Val His Ile Val Trp
        35                  40                  45

Ser Leu Val Arg Arg Phe Asp Gln Pro Gln Lys Tyr Lys Pro Phe Ile
    50                  55                  60

Ser Arg Cys Val Val Lys Gly Asn Met Glu Ile Gly Thr Val Arg Glu
65                  70                  75                  80

Val Asp Val Lys Ser Gly Leu Pro Ala Thr Arg Ser Thr Glu Arg Leu
                85                  90                  95

Glu Leu Leu Asp Asp Asn Glu His Ile Leu Ser Ile Arg Ile Val Gly
            100                 105                 110

Gly Asp His Arg Leu Lys Asn Tyr Ser Ser Ile Ile Ser Leu His Pro
        115                 120                 125

Glu Thr Ile Glu Gly Arg Ile Gly Thr Leu Val Ile Glu Ser Phe Val
    130                 135                 140

Val Asp Val Pro Glu Gly Asn Thr Lys Asp Glu Thr Cys Tyr Phe Val
145                 150                 155                 160

Glu Ala Leu Ile Lys Cys Asn Leu Lys Ser Leu Ala Asp Ile Ser Glu
                165                 170                 175

Arg Leu Ala Val Gln Asp Thr Thr Glu Ser Arg Val
            180                 185

<210> SEQ ID NO 10
<211> LENGTH: 187
```

<212> TYPE: PRT
<213> ORGANISM: Arabidopsis thaliana
<220> FEATURE:
<223> OTHER INFORMATION: thale cress PYR/PYL receptor, abscisic acid
      receptor PYL9, PYR1-like protein 9 (PYL9), ABI1-binding protein 4
      (ABIP4), regulatory components of ABA receptor 1 (RCAR1),
      At1g01360, F6F3.16

<400> SEQUENCE: 10

Met Met Asp Gly Val Glu Gly Thr Ala Met Tyr Gly Gly Leu Glu
1               5                   10                  15

Thr Val Gln Tyr Val Arg Thr His His Gln His Leu Cys Arg Glu Asn
                20                  25                  30

Gln Cys Thr Ser Ala Leu Val Lys His Ile Lys Ala Pro Leu His Leu
            35                  40                  45

Val Trp Ser Leu Val Arg Arg Phe Asp Gln Pro Gln Lys Tyr Lys Pro
    50                  55                  60

Phe Val Ser Arg Cys Thr Val Ile Gly Asp Pro Glu Ile Gly Ser Leu
65                  70                  75                  80

Arg Glu Val Asn Val Lys Ser Gly Leu Pro Ala Thr Thr Ser Thr Glu
                85                  90                  95

Arg Leu Glu Leu Leu Asp Asp Glu Glu His Ile Leu Gly Ile Lys Ile
            100                 105                 110

Ile Gly Gly Asp His Arg Leu Lys Asn Tyr Ser Ser Ile Leu Thr Val
        115                 120                 125

His Pro Glu Ile Ile Glu Gly Arg Ala Gly Thr Met Val Ile Glu Ser
130                 135                 140

Phe Val Val Asp Val Pro Gln Gly Asn Thr Lys Asp Glu Thr Cys Tyr
145                 150                 155                 160

Phe Val Glu Ala Leu Ile Arg Cys Asn Leu Lys Ser Leu Ala Asp Val
                165                 170                 175

Ser Glu Arg Leu Ala Ser Gln Asp Ile Thr Gln
            180                 185

<210> SEQ ID NO 11
<211> LENGTH: 183
<212> TYPE: PRT
<213> ORGANISM: Arabidopsis thaliana
<220> FEATURE:
<223> OTHER INFORMATION: thale cress PYR/PYL receptor, abscisic acid
      receptor PYL10, PYR1-like protein 10 (PYL10), ABI1-binding protein
      8 (ABIP8), regulatory components of ABA receptor 4 (RCAR4),
      At4g27920, T13J8.30

<400> SEQUENCE: 11

Met Asn Gly Asp Glu Thr Lys Lys Val Glu Ser Glu Tyr Ile Lys Lys
1               5                   10                  15

His His Arg His Glu Leu Val Glu Ser Gln Cys Ser Ser Thr Leu Val
                20                  25                  30

Lys His Ile Lys Ala Pro Leu His Leu Val Trp Ser Ile Val Arg Arg
            35                  40                  45

Phe Asp Glu Pro Gln Lys Tyr Lys Pro Phe Ile Ser Arg Cys Val Val
        50                  55                  60

Gln Gly Lys Lys Leu Glu Val Gly Ser Val Arg Glu Val Asp Leu Lys
65                  70                  75                  80

Ser Gly Leu Pro Ala Thr Lys Ser Thr Glu Val Leu Glu Ile Leu Asp
                85                  90                  95

Asp Asn Glu His Ile Leu Gly Ile Arg Ile Val Gly Gly Asp His Arg
            100                 105                 110

```
Leu Lys Asn Tyr Ser Ser Thr Ile Ser Leu His Ser Glu Thr Ile Asp
        115                 120                 125

Gly Lys Thr Gly Thr Leu Ala Ile Glu Ser Phe Val Val Asp Val Pro
    130                 135                 140

Glu Gly Asn Thr Lys Glu Thr Cys Phe Phe Val Glu Ala Leu Ile
145                 150                 155                 160

Gln Cys Asn Leu Asn Ser Leu Ala Asp Val Thr Glu Arg Leu Gln Ala
                165                 170                 175

Glu Ser Met Glu Lys Lys Ile
            180
```

<210> SEQ ID NO 12
<211> LENGTH: 161
<212> TYPE: PRT
<213> ORGANISM: Arabidopsis thaliana
<220> FEATURE:
<223> OTHER INFORMATION: thale cress PYR/PYL receptor, abscisic acid
      receptor PYL11, PYR1-like protein 11 (PYL11), regulatory
      components of ABA receptor 5 (RCAR5), Bet v I allergen family
      protein, At5g45860, K15I22.6

<400> SEQUENCE: 12

```
Met Glu Thr Ser Gln Lys Tyr His Thr Cys Gly Ser Thr Leu Val Gln
1               5                   10                  15

Thr Ile Asp Ala Pro Leu Ser Leu Val Trp Ser Ile Leu Arg Arg Phe
            20                  25                  30

Asp Asn Pro Gln Ala Tyr Lys Gln Phe Val Lys Thr Cys Asn Leu Ser
        35                  40                  45

Ser Gly Asp Gly Gly Glu Gly Ser Val Arg Glu Val Thr Val Val Ser
    50                  55                  60

Gly Leu Pro Ala Glu Phe Ser Arg Glu Arg Leu Asp Glu Leu Asp Asp
65                  70                  75                  80

Glu Ser His Val Met Met Ile Ser Ile Ile Gly Gly Asp His Arg Leu
                85                  90                  95

Val Asn Tyr Arg Ser Lys Thr Met Ala Phe Val Ala Ala Asp Thr Glu
            100                 105                 110

Glu Lys Thr Val Val Val Glu Ser Tyr Val Val Asp Val Pro Glu Gly
        115                 120                 125

Asn Ser Glu Glu Glu Thr Thr Ser Phe Ala Asp Thr Ile Val Gly Phe
    130                 135                 140

Asn Leu Lys Ser Leu Ala Lys Leu Ser Glu Arg Val Ala His Leu Lys
145                 150                 155                 160

Leu
```

<210> SEQ ID NO 13
<211> LENGTH: 159
<212> TYPE: PRT
<213> ORGANISM: Arabidopsis thaliana
<220> FEATURE:
<223> OTHER INFORMATION: thale cress PYR/PYL receptor, abscisic acid
      receptor PYL12, PYR1-like protein 12 (PYL12), regulatory
      components of ABA receptor 6 (RCAR6), Bet v I allergen family
      protein, At5g45870, K15I22.7

<400> SEQUENCE: 13

```
Met Lys Thr Ser Gln Glu Gln His Val Cys Gly Ser Thr Val Val Gln
1               5                   10                  15

Thr Ile Asn Ala Pro Leu Pro Leu Val Trp Ser Ile Leu Arg Arg Phe
            20                  25                  30
```

```
Asp Asn Pro Lys Thr Phe Lys His Phe Val Lys Thr Cys Lys Leu Arg
            35                  40                  45

Ser Gly Asp Gly Gly Glu Gly Ser Val Arg Glu Val Thr Val Val Ser
    50                  55                  60

Asp Leu Pro Ala Ser Phe Ser Leu Glu Arg Leu Asp Glu Leu Asp Asp
65                  70                  75                  80

Glu Ser His Val Met Val Ile Ser Ile Ile Gly Gly Asp His Arg Leu
                85                  90                  95

Val Asn Tyr Gln Ser Lys Thr Thr Val Phe Val Ala Ala Glu Glu Glu
            100                 105                 110

Lys Thr Val Val Val Glu Ser Tyr Val Val Asp Val Pro Glu Gly Asn
            115                 120                 125

Thr Glu Glu Glu Thr Thr Leu Phe Ala Asp Thr Ile Val Gly Cys Asn
130                 135                 140

Leu Arg Ser Leu Ala Lys Leu Ser Glu Lys Met Met Glu Leu Thr
145                 150                 155

<210> SEQ ID NO 14
<211> LENGTH: 164
<212> TYPE: PRT
<213> ORGANISM: Arabidopsis thaliana
<220> FEATURE:
<223> OTHER INFORMATION: thale cress PYR/PYL receptor, abscisic acid
      receptor PYL13, PYR1-like protein 13 (PYL13), regulatory
      components of ABA receptor 7 (RCAR7), At4g18620, F28A21.30

<400> SEQUENCE: 14

Met Glu Ser Ser Lys Gln Lys Arg Cys Arg Ser Ser Val Val Glu Thr
1               5                   10                  15

Ile Glu Ala Pro Leu Pro Leu Val Trp Ser Ile Leu Arg Ser Phe Asp
            20                  25                  30

Lys Pro Gln Ala Tyr Gln Arg Phe Val Lys Ser Cys Thr Met Arg Ser
            35                  40                  45

Gly Gly Gly Gly Gly Lys Gly Gly Glu Gly Lys Gly Ser Val Arg Asp
    50                  55                  60

Val Thr Leu Val Ser Gly Phe Pro Ala Asp Phe Ser Thr Glu Arg Leu
65                  70                  75                  80

Glu Glu Leu Asp Asp Glu Ser His Val Met Val Val Ser Ile Ile Gly
                85                  90                  95

Gly Asn His Arg Leu Val Asn Tyr Lys Ser Lys Thr Lys Val Val Ala
            100                 105                 110

Ser Pro Glu Asp Met Ala Lys Lys Thr Val Val Val Glu Ser Tyr Val
            115                 120                 125

Val Asp Val Pro Glu Gly Thr Ser Glu Glu Asp Thr Ile Phe Phe Val
            130                 135                 140

Asp Asn Ile Ile Arg Tyr Asn Leu Thr Ser Leu Ala Lys Leu Thr Lys
145                 150                 155                 160

Lys Met Met Lys

<210> SEQ ID NO 15
<211> LENGTH: 191
<212> TYPE: PRT
<213> ORGANISM: Brassica oleracea
<220> FEATURE:
<223> OTHER INFORMATION: wild cabbage Streptomyces cyclase/dehydrase
      family protein, locus tag 40.t00062, GenBank Accession No.
      ABD65175.1
```

```
<400> SEQUENCE: 15

Met Pro Ser Gln Leu Thr Pro Glu Glu Arg Ser Glu Leu Ala Gln Ser
1               5                   10                  15

Ile Ala Glu Phe His Thr Tyr His Leu Gly Pro Gly Ser Cys Ser Ser
                20                  25                  30

Leu His Ala Gln Arg Ile His Ala Pro Pro Glu Ile Val Trp Ser Val
            35                  40                  45

Val Arg Arg Phe Asp Lys Pro Gln Thr Tyr Lys His Phe Ile Lys Ser
50                  55                  60

Cys Ser Val Glu Asp Gly Phe Glu Met Arg Val Gly Cys Thr Arg Ala
65                  70                  75                  80

Val Asn Val Ile Ser Gly Leu Pro Ala Asn Thr Ser Thr Glu Arg Leu
                85                  90                  95

Asp Ile Leu Asp Asp Glu Arg Arg Val Thr Gly Phe Ser Ile Ile Gly
            100                 105                 110

Gly Glu His Arg Leu Thr Asn Tyr Lys Ser Val Thr Thr Val His Arg
        115                 120                 125

Phe Glu Lys Glu Arg Arg Ile Trp Thr Val Val Leu Glu Ser Tyr Val
130                 135                 140

Val Asp Met Pro Glu Gly Asn Ser Glu Asp Asp Thr Arg Met Phe Ala
145                 150                 155                 160

Asp Thr Val Val Lys Leu Asn Leu Gln Lys Leu Ala Thr Val Thr Glu
                165                 170                 175

Ala Met Ala Arg Asn Ala Gly Asp Gly Ser Gly Ala Gln Val Thr
            180                 185                 190

<210> SEQ ID NO 16
<211> LENGTH: 281
<212> TYPE: PRT
<213> ORGANISM: Brassica oleracea
<220> FEATURE:
<223> OTHER INFORMATION: wild cabbage Streptomyces cyclase/dehydrase
      family protein, locus tag 23.t00047, GenBank Accession No.
      ABD65631.1

<400> SEQUENCE: 16

Met Pro Ser Glu Leu Thr Gln Glu Glu Arg Ser Lys Leu Thr Gln Ser
1               5                   10                  15

Ile Ser Glu Phe His Thr Tyr His Leu Gly Pro Gly Ser Cys Ser Ser
                20                  25                  30

Leu His Ala Gln Arg Ile His Ala Pro Pro Glu Ile Val Trp Ser Val
            35                  40                  45

Val Arg Gln Phe Asp Lys Pro Gln Thr Tyr Lys His Phe Ile Lys Ser
50                  55                  60

Cys Ser Val Glu Glu Gly Phe Glu Met Arg Val Gly Cys Thr Arg Asp
65                  70                  75                  80

Val Ile Val Ile Ser Gly Leu Pro Ala Asn Thr Ser Thr Glu Arg Leu
                85                  90                  95

Asp Met Leu Asp Asp Glu Arg Arg Val Thr Gly Phe Ser Ile Ile Gly
            100                 105                 110

Gly Glu His Arg Leu Lys Asn Tyr Lys Ser Val Thr Thr Val His Arg
        115                 120                 125

Phe Glu Arg Glu Arg Arg Ile Trp Thr Val Val Leu Glu Ser Tyr Val
130                 135                 140

Val Asp Met Pro Glu Gly Asn Ser Glu Asp Asp Thr Arg Met Phe Ala
145                 150                 155                 160
```

```
Asp Thr Val Val Lys Leu Asn Leu Gln Lys Leu Ala Thr Val Thr Glu
            165                 170                 175

Ala Met Ala Arg Asn Ala Gly Asp Gly Arg Gly Ser Arg Glu Thr Thr
        180                 185                 190

Cys Arg Glu Ser Phe His Leu Ile Thr Ala Phe Glu Lys Gln Arg Gln
    195                 200                 205

Ile Thr Glu Pro Thr Val Tyr Gln Asn Pro Tyr His Thr Gly Met
210                 215                 220

Thr Pro Glu Pro Arg Thr Ser Thr Val Phe Ile Glu Leu Glu Asp His
225                 230                 235                 240

Arg Thr Leu Pro Gly Asn Leu Thr Pro Thr Thr Glu Glu His Leu Gln
            245                 250                 255

Arg Met Tyr Gln Arg Phe Trp Gly Ile Arg Gln Leu Gln Arg Pro Arg
        260                 265                 270

Gln Ser Phe Gly Glu Arg Gln Ser Ile
    275                 280

<210> SEQ ID NO 17
<211> LENGTH: 453
<212> TYPE: PRT
<213> ORGANISM: Vitis vinifera
<220> FEATURE:
<223> OTHER INFORMATION: wine grape cultivar PN40024 unnamed protein
      product, locus tag GSVIVT00015766001, GenBank Accession No.
      CAO63410.1

<400> SEQUENCE: 17

Met Gln Met Lys Tyr Leu Glu Gly Lys Gln Asn Leu Met Glu Glu Lys
1               5                   10                  15

Gly Glu Lys Gln Cys Ile Pro Met Asp Leu Ala Val Arg Glu Ala Gln
            20                  25                  30

Phe Lys Gly Ser Leu Leu Asp Arg Ile Thr Trp Leu Glu Gln Arg Leu
        35                  40                  45

His Lys Leu Ser Leu Gln Leu Glu Thr Arg Ser Lys Gln Gln Pro His
    50                  55                  60

Pro Ser Arg Met Gln Thr Ala Gly Glu Thr Ser Ser Arg His Gly Pro
65                  70                  75                  80

Lys Lys Glu Leu Ser Cys Ser Phe Pro Val Phe Ser Thr Arg Asn His
                85                  90                  95

Asn His Gly His Lys Gln Thr Ser Gln Phe His Val Pro Arg Phe Glu
            100                 105                 110

Tyr Gln Glu Gly Gly Arg Glu Asn Pro Ala Val Val Ile Thr Lys Leu
        115                 120                 125

Thr Pro Phe His His Pro Lys Ile Ile Thr Ile Leu Phe Pro Ile Ser
    130                 135                 140

Asn Tyr Phe Ile Ile Phe Phe Phe Leu Thr Phe Asp Thr Lys Lys Gln
145                 150                 155                 160

Tyr Pro Leu Leu Phe Pro Ile Leu Pro Ser Arg Phe Leu Pro Ile Ser
                165                 170                 175

His Leu Ile Thr Gln Glu Ile Glu Lys Tyr Lys Thr Ser Ser His Phe
            180                 185                 190

Ser Ser Pro Ala Ser Leu Phe Ala Ala Met Asn Lys Ala Glu Thr Ser
        195                 200                 205

Ser Met Ala Glu Ala Glu Ser Glu Asp Ser Glu Thr Thr Thr Pro Thr
    210                 215                 220
```

```
Thr His His Leu Thr Ile Pro Pro Gly Leu Thr Gln Pro Glu Phe Gln
225                 230                 235                 240

Glu Leu Ala His Ser Ile Ser Glu Phe His Thr Tyr Gln Val Gly Pro
            245                 250                 255

Gly Gln Cys Ser Ser Leu Leu Ala Gln Arg Val His Ala Pro Leu Pro
        260                 265                 270

Thr Val Trp Ser Val Val Arg Arg Phe Asp Lys Pro Gln Thr Tyr Lys
    275                 280                 285

His Phe Ile Lys Ser Cys His Val Glu Asp Gly Phe Glu Met Arg Val
290                 295                 300

Gly Cys Leu Arg Asp Val Asn Val Ile Ser Gly Leu Pro Ala Glu Thr
305                 310                 315                 320

Ser Thr Glu Arg Leu Asp Ile Leu Asp Asp Glu Arg His Val Thr Gly
            325                 330                 335

Phe Ser Ile Ile Gly Gly Glu His Arg Leu Arg Asn Tyr Arg Ser Val
        340                 345                 350

Thr Thr Asn His Gly Gly Glu Ile Trp Thr Val Val Leu Glu Ser Tyr
    355                 360                 365

Val Val Asp Met Pro Glu Gly Asn Thr Glu Glu Asp Thr Arg Leu Phe
370                 375                 380

Ala Asp Thr Val Val Lys Leu Asn Leu Gln Lys Leu Ala Ser Val Thr
385                 390                 395                 400

Glu Val Ser Gln Ser Cys Asn Tyr Pro Cys Gln Phe His Ile Ile Glu
            405                 410                 415

Asn Glu Asp Ile Gln Pro Glu Glu Met Asn Leu Gly Val Leu Thr Thr
        420                 425                 430

Ser Ile Glu Glu Gln Arg Lys Lys Lys Arg Val Val Ala Met Lys Asp
    435                 440                 445

Gly Ser Thr Ser Ser
        450

<210> SEQ ID NO 18
<211> LENGTH: 195
<212> TYPE: PRT
<213> ORGANISM: Vitis vinifera
<220> FEATURE:
<223> OTHER INFORMATION: wine grape cultivar Pinot Noir hypothetical
      protein, clone ENTAV 115, locus tag VITISV_033963, GenBank
      Accession No. CAN64657.1
<220> FEATURE:
<221> NAME/KEY: VARIANT
<222> LOCATION: (193)...(193)
<223> OTHER INFORMATION: Xaa = any amino acid

<400> SEQUENCE: 18

Met Ala Glu Ala Glu Ser Glu Asp Ser Glu Thr Thr Thr Pro Thr Thr
1               5                   10                  15

His His Leu Thr Ile Pro Pro Gly Leu Thr Gln Pro Glu Phe Gln Glu
            20                  25                  30

Leu Ala His Ser Ile Ser Glu Phe His Thr Tyr Gln Val Gly Pro Gly
        35                  40                  45

Gln Cys Ser Ser Leu Leu Ala Gln Arg Val His Ala Pro Leu Pro Thr
    50                  55                  60

Val Trp Ser Val Val Arg Arg Phe Asp Lys Pro Gln Thr Tyr Lys His
65                  70                  75                  80

Phe Ile Lys Ser Cys His Val Glu Asp Gly Phe Glu Met Arg Val Gly
                85                  90                  95
```

```
Cys Leu Arg Asp Val Asn Val Ile Ser Gly Leu Pro Ala Glu Thr Ser
                100                 105                 110

Thr Glu Arg Leu Asp Ile Leu Asp Asp Glu Arg His Val Thr Gly Phe
            115                 120                 125

Ser Ile Ile Gly Gly Glu His Arg Leu Arg Asn Tyr Arg Ser Val Thr
        130                 135                 140

Thr Val His Glu Tyr Gln Asn His Gly Gly Glu Ile Trp Thr Val Val
145                 150                 155                 160

Leu Glu Ser Tyr Val Val Asp Met Pro Glu Gly Asn Thr Glu Glu Asp
                165                 170                 175

Thr Arg Leu Phe Ala Asp Thr Val Val Lys Leu Asn Leu Ser Glu Ala
            180                 185                 190

Xaa Arg Arg
    195
```

<210> SEQ ID NO 19
<211> LENGTH: 217
<212> TYPE: PRT
<213> ORGANISM: Medicago truncatula
<220> FEATURE:
<223> OTHER INFORMATION: barrel medic unknown protein, clone
     MTYFD_FE_FF_FG1G-N-24, GenBank Accession No. ACJ85026.1

<400> SEQUENCE: 19

```
Met Glu Lys Ala Glu Ser Ser Thr Ala Ser Thr Ser Asp Gln Asp Ser
1               5                   10                  15

Asp Glu Asn His Arg Thr Gln His Leu Thr Leu Pro Ser Gly Leu
            20                  25                  30

Arg Gln His Glu Phe Asp Ser Leu Ile Pro Phe Ile Asn Ser His His
        35                  40                  45

Thr Tyr Leu Ile Gly Pro Asn Gln Cys Ser Thr Leu Leu Ala Gln Arg
    50                  55                  60

Ile His Ala Pro Pro Gln Thr Val Trp Ser Val Val Arg Ser Phe Asp
65                  70                  75                  80

Lys Pro Gln Ile Tyr Lys His Ile Ile Lys Ser Cys Ser Leu Lys Glu
                85                  90                  95

Gly Phe Gln Met Lys Val Gly Cys Thr Arg Asp Val Asn Val Ile Ser
                100                 105                 110

Gly Leu Pro Ala Ala Thr Ser Thr Glu Arg Leu Asp Val Leu Asp Asp
            115                 120                 125

Glu Arg Arg Val Thr Gly Phe Ser Ile Ile Gly Gly Glu His Arg Leu
        130                 135                 140

Lys Asn Tyr Arg Ser Val Thr Ser Val His Gly Phe Gly Asp Gly Asp
145                 150                 155                 160

Asn Gly Gly Glu Ile Trp Thr Val Val Leu Glu Ser Tyr Val Val Asp
                165                 170                 175

Val Pro Glu Gly Asn Thr Glu Glu Asp Thr Arg Leu Phe Ala Asp Thr
            180                 185                 190

Val Val Lys Leu Asn Leu Gln Lys Leu Ala Ser Val Thr Glu Gly Lys
        195                 200                 205

Asn Arg Asp Gly Asp Gly Lys Ser His
    210                 215
```

<210> SEQ ID NO 20
<211> LENGTH: 212
<212> TYPE: PRT
<213> ORGANISM: Oryza sativa
<220> FEATURE:
<223> OTHER INFORMATION: rice Japonica Group, cultivar Nipponbare,
      conserved hypothetical protein Os10g0573400, GenBank Accession No.
      NP_00106570.1

<400> SEQUENCE: 20

Met Glu Gln Gln Glu Glu Val Pro Pro Pro Ala Gly Leu Gly Leu
1               5                   10                  15

Thr Ala Glu Glu Tyr Ala Gln Val Arg Ala Thr Val Glu Ala His His
            20                  25                  30

Arg Tyr Ala Val Gly Pro Gly Gln Cys Ser Ser Leu Leu Ala Gln Arg
        35                  40                  45

Ile His Ala Pro Pro Ala Ala Val Trp Ala Val Val Arg Arg Phe Asp
50                  55                  60

Cys Pro Gln Val Tyr Lys His Phe Ile Arg Ser Cys Val Leu Arg Pro
65                  70                  75                  80

Asp Pro His His Asp Asp Asn Gly Asn Asp Leu Arg Pro Gly Arg Leu
                85                  90                  95

Arg Glu Val Ser Val Ile Ser Gly Leu Pro Ala Ser Thr Ser Thr Glu
            100                 105                 110

Arg Leu Asp Leu Leu Asp Asp Ala His Arg Val Phe Gly Phe Thr Ile
        115                 120                 125

Thr Gly Gly Glu His Arg Leu Arg Asn Tyr Arg Ser Val Thr Thr Val
130                 135                 140

Ser Gln Leu Asp Glu Ile Cys Thr Leu Val Leu Glu Ser Tyr Ile Val
145                 150                 155                 160

Asp Val Pro Asp Gly Asn Thr Glu Asp Thr Arg Leu Phe Ala Asp
                165                 170                 175

Thr Val Ile Arg Leu Asn Leu Gln Lys Leu Lys Ser Val Ser Glu Ala
            180                 185                 190

Asn Ala Asn Ala Ala Ala Ala Ala Ala Pro Pro Pro Pro Pro
        195                 200                 205

Ala Ala Ala Glu
    210

<210> SEQ ID NO 21
<211> LENGTH: 212
<212> TYPE: PRT
<213> ORGANISM: Zea mays
<220> FEATURE:
<223> OTHER INFORMATION: maize cyclase/dehydrase family protein, clone
      306819, GenBank Accession No. ACG40002.1

<400> SEQUENCE: 21

Met Asp Gln Gln Gly Ala Gly Gly Asp Ala Glu Val Pro Ala Gly Leu
1               5                   10                  15

Gly Leu Thr Ala Ala Glu Tyr Glu Gln Leu Arg Ser Thr Val Asp Ala
            20                  25                  30

His His Arg Tyr Ala Val Gly Glu Gly Gln Cys Ser Ser Leu Leu Ala
        35                  40                  45

Gln Arg Ile His Ala Pro Pro Glu Ala Val Trp Ala Val Val Arg Arg
50                  55                  60

Phe Asp Cys Pro Gln Val Tyr Lys His Phe Ile Arg Ser Cys Ala Leu
65                  70                  75                  80

Arg Pro Asp Pro Glu Ala Gly Asp Ala Leu Cys Pro Gly Arg Leu Arg
                85                  90                  95

Glu Val Ser Val Ile Ser Gly Leu Pro Ala Ser Thr Ser Thr Glu Arg

```
                    100                 105                 110
Leu Asp Leu Leu Asp Asp Ala Ala Arg Val Phe Gly Phe Ser Ile Thr
            115                 120                 125
Gly Gly Glu His Arg Leu Arg Asn Tyr Arg Ser Val Thr Thr Val Ser
            130                 135                 140
Glu Leu Ala Val Pro Ala Ile Cys Thr Val Val Leu Glu Ser Tyr Val
145                 150                 155                 160
Val Asp Val Pro Asp Gly Asn Thr Glu Asp Asp Thr Arg Leu Phe Ala
                165                 170                 175
Asp Thr Val Ile Arg Leu Asn Leu Gln Lys Leu Lys Ser Val Ala Glu
                180                 185                 190
Ala Asn Ala Ala Glu Ala Ala Ala Thr Thr Asn Ser Val Leu Leu Pro
            195                 200                 205
Arg Pro Ala Glu
            210

<210> SEQ ID NO 22
<211> LENGTH: 212
<212> TYPE: PRT
<213> ORGANISM: Zea mays
<220> FEATURE:
<223> OTHER INFORMATION: maize cyclase/dehydrase family protein, clone
      241996, GenBank Accession No. ACG34473.1
<220> FEATURE:
<221> NAME/KEY: VARIANT
<222> LOCATION: (11)...(11)
<223> OTHER INFORMATION: Xaa = any amino acid

<400> SEQUENCE: 22

Met Asp Gln Gln Gly Ala Gly Gly Asp Ala Xaa Val Pro Ala Gly Leu
1               5                   10                  15
Gly Leu Thr Ala Ala Glu Tyr Glu Gln Leu Arg Ser Thr Val Asp Ala
            20                  25                  30
His His Arg Tyr Ala Val Gly Glu Gly Gln Cys Ser Ser Leu Leu Ala
            35                  40                  45
Gln Arg Ile His Ala Pro Pro Glu Ala Val Trp Ala Val Val Arg Arg
        50                  55                  60
Phe Asp Cys Pro Gln Val Tyr Lys His Phe Ile Arg Ser Cys Ala Leu
65                  70                  75                  80
Arg Pro Asp Pro Glu Ala Gly Asp Ala Leu Cys Pro Gly Arg Leu Arg
                85                  90                  95
Glu Val Ser Val Ile Ser Gly Leu Pro Ala Ser Thr Ser Thr Glu Arg
            100                 105                 110
Leu Asp Leu Leu Asp Asp Ala Ala Arg Val Phe Gly Phe Ser Ile Thr
            115                 120                 125
Gly Gly Glu His Arg Leu Arg Asn Tyr Arg Ser Val Thr Thr Val Ser
            130                 135                 140
Glu Leu Ala Asp Pro Ala Ile Cys Thr Val Val Leu Glu Ser Tyr Val
145                 150                 155                 160
Val Asp Val Pro Asp Gly Asn Thr Glu Asp Asp Thr Arg Leu Phe Ala
                165                 170                 175
Asp Thr Val Ile Arg Leu Asn Leu Gln Lys Leu Lys Ser Val Thr Glu
                180                 185                 190
Ala Asn Ala Ala Glu Ala Ala Ala Thr Thr Asn Ser Val Leu Leu Pro
            195                 200                 205
Arg Pro Ala Glu
            210
```

<210> SEQ ID NO 23
<211> LENGTH: 233
<212> TYPE: PRT
<213> ORGANISM: Vitis vinifera
<220> FEATURE:
<223> OTHER INFORMATION: wine grape cultivar PN40024 unnamed protein
    product, locus tag GSVIVT00032173001, GenBank Accession No.
    CAO43790.1

<400> SEQUENCE: 23

Met Asp Pro His His His His Gly Leu Thr Glu Glu Phe Arg Ala
1               5                   10                  15

Leu Glu Pro Ile Ile Gln Asn Tyr His Thr Phe Glu Pro Ser Pro Asn
            20                  25                  30

Thr Cys Thr Ser Leu Ile Thr Gln Lys Ile Asp Ala Pro Ala Gln Val
        35                  40                  45

Val Trp Pro Phe Val Arg Ser Phe Glu Asn Pro Gln Lys Tyr Lys His
    50                  55                  60

Phe Ile Lys Asp Cys Thr Met Arg Gly Asp Gly Val Gly Ser Ile
65                  70                  75                  80

Arg Glu Val Thr Val Val Ser Gly Leu Pro Ala Ser Thr Ser Thr Glu
                85                  90                  95

Arg Leu Glu Ile Leu Asp Asp Glu Lys His Ile Leu Ser Phe Arg Val
            100                 105                 110

Val Gly Gly Glu His Arg Leu Asn Asn Tyr Arg Ser Val Thr Ser Val
        115                 120                 125

Asn Asp Phe Ser Lys Glu Gly Lys Asp Tyr Thr Ile Val Leu Glu Ser
    130                 135                 140

Tyr Ile Val Asp Ile Pro Glu Gly Asn Thr Gly Glu Asp Thr Lys Met
145                 150                 155                 160

Phe Val Asp Thr Val Val Lys Leu Asn Leu Gln Lys Leu Ala Val Val
                165                 170                 175

Ala Ile Thr Ser Leu His Glu Asn Glu Glu Ile Ala Asp Asn Glu Gly
            180                 185                 190

Pro Ser Arg Glu Ile Ser Leu Gln Ser Glu Thr Glu Ser Ala Glu Arg
        195                 200                 205

Gly Asp Glu Arg Arg Asp Gly Asp Gly Pro Ser Lys Ala Cys Asn Arg
    210                 215                 220

Asn Glu Trp His Cys Thr Thr Lys Glu
225                 230

<210> SEQ ID NO 24
<211> LENGTH: 207
<212> TYPE: PRT
<213> ORGANISM: Oryza sativa
<220> FEATURE:
<223> OTHER INFORMATION: rice Japonica Group, cultivar Nipponbare,
    Bet v I allergen-like protein, clone P0495C02.29, GenBank
    Accession No. BAD25659.1

<400> SEQUENCE: 24

Met Glu Pro His Met Glu Arg Ala Leu Arg Glu Ala Val Ala Ser Glu
1               5                   10                  15

Ala Glu Arg Arg Glu Leu Glu Gly Val Val Arg Ala His His Thr Phe
            20                  25                  30

Pro Ala Ala Glu Arg Ala Ala Gly Pro Gly Arg Arg Pro Thr Cys Thr
        35                  40                  45

-continued

```
Ser Leu Val Ala Gln Arg Val Asp Ala Pro Leu Ala Ala Val Trp Pro
 50                  55                  60

Ile Val Arg Gly Phe Ala Asn Pro Gln Arg Tyr Lys His Phe Ile Lys
 65                  70                  75                  80

Ser Cys Glu Leu Ala Ala Gly Asp Gly Ala Thr Val Gly Ser Val Arg
                 85                  90                  95

Glu Val Ala Val Val Ser Gly Leu Pro Ala Ser Thr Ser Thr Glu Arg
            100                 105                 110

Leu Glu Ile Leu Asp Asp Asp Arg His Val Leu Ser Phe Arg Val Val
        115                 120                 125

Gly Gly Asp His Arg Leu Arg Asn Tyr Arg Ser Val Thr Ser Val Thr
    130                 135                 140

Glu Phe Ser Ser Pro Ser Ser Pro Pro Arg Pro Tyr Cys Val Val Val
145                 150                 155                 160

Glu Ser Tyr Val Val Asp Val Pro Glu Gly Asn Thr Glu Asp Thr
                165                 170                 175

Arg Met Phe Thr Asp Thr Val Val Lys Leu Asn Leu Gln Lys Leu Ala
            180                 185                 190

Ala Val Ala Thr Ser Ser Ser Pro Pro Ala Ala Gly Asn His His
        195                 200                 205
```

<210> SEQ ID NO 25
<211> LENGTH: 210
<212> TYPE: PRT
<213> ORGANISM: Oryza sativa
<220> FEATURE:
<223> OTHER INFORMATION: rice Indica Group, cultivar 93-11, hypothetical
      protein OsI_06433, GenBank Accession No. EAY85077.1

<400> SEQUENCE: 25

```
Met Glu Pro His Met Glu Arg Ala Leu Arg Glu Ala Val Ala Ser Glu
  1               5                  10                  15

Ala Glu Arg Arg Glu Leu Glu Gly Val Val Arg Ala His His Thr Phe
             20                  25                  30

Pro Ala Ala Glu Arg Ala Ala Gly Pro Gly Arg Arg Pro Thr Cys Thr
         35                  40                  45

Ser Leu Val Ala Gln Arg Val Asp Ala Pro Leu Ala Ala Val Trp Pro
 50                  55                  60

Ile Val Arg Gly Phe Ala Asn Pro Gln Arg Tyr Lys His Phe Ile Lys
 65                  70                  75                  80

Ser Cys Glu Leu Ala Ala Gly Asp Gly Ala Thr Val Gly Ser Val Arg
                 85                  90                  95

Glu Val Ala Val Val Ser Gly Leu Pro Ala Ser Thr Ser Thr Glu Arg
            100                 105                 110

Leu Glu Ile Leu Asp Asp Asp Arg His Val Leu Ser Phe Arg Val Val
        115                 120                 125

Gly Gly Asp His Arg Leu Arg Asn Tyr Arg Ser Val Thr Ser Val Thr
    130                 135                 140

Glu Phe Ser Ser Pro Ser Ser Pro Ser Pro Pro Arg Pro Tyr Cys
145                 150                 155                 160

Val Val Val Glu Ser Tyr Val Val Asp Val Pro Glu Gly Asn Thr Glu
                165                 170                 175

Glu Asp Thr Arg Met Phe Thr Asp Thr Val Val Lys Leu Asn Leu Gln
            180                 185                 190

Lys Leu Ala Ala Val Ala Thr Ser Ser Ser Pro Pro Ala Ala Gly Asn
        195                 200                 205
```

His His
    210

<210> SEQ ID NO 26
<211> LENGTH: 200
<212> TYPE: PRT
<213> ORGANISM: Zea mays
<220> FEATURE:
<223> OTHER INFORMATION: maize strain B73 unknown protein, clone
      ZM_BFb0151H07, GenBank Accession No. ACF82013.1

<400> SEQUENCE: 26

Met Pro Tyr Thr Ala Pro Arg Pro Ser Pro Gln Gln His Ser Arg Val
1               5                   10                  15

Leu Ser Gly Gly Gly Ala Lys Ala Ala Ser His Gly Ala Ser Cys Ala
            20                  25                  30

Ala Val Pro Ala Glu Val Ala Arg His His Glu His Ala Ala Arg Ala
        35                  40                  45

Gly Gln Cys Cys Ser Ala Val Val Gln Ala Ile Ala Ala Pro Val Gly
    50                  55                  60

Ala Val Trp Ser Val Val Arg Arg Phe Asp Arg Pro Gln Ala Tyr Lys
65                  70                  75                  80

His Phe Ile Arg Ser Cys Arg Leu Val Gly Gly Asp Val Ala Val
                85                  90                  95

Gly Ser Val Arg Glu Val Arg Val Ser Gly Leu Pro Ala Thr Ser
            100                 105                 110

Ser Arg Glu Arg Leu Glu Ile Leu Asp Asp Glu Arg Arg Val Leu Ser
        115                 120                 125

Phe Arg Val Val Gly Gly Glu His Arg Leu Ala Asn Tyr Arg Ser Val
    130                 135                 140

Thr Thr Val His Glu Ala Gly Ala Gly Ala Gly Thr Gly Thr Val Val
145                 150                 155                 160

Val Glu Ser Tyr Val Val Asp Val Pro His Gly Asn Thr Ala Asp Glu
                165                 170                 175

Thr Arg Val Phe Val Asp Thr Ile Val Arg Cys Asn Leu Gln Ser Leu
            180                 185                 190

Ala Arg Thr Ala Glu Arg Leu Ala
        195                 200

<210> SEQ ID NO 27
<211> LENGTH: 215
<212> TYPE: PRT
<213> ORGANISM: Vitis vinifera
<220> FEATURE:
<223> OTHER INFORMATION: wine grape cultivar PN40024 unnamed protein
      product, locus tag GSVIVT00037390001, GenBank Accession No.
      CAO48777.1

<400> SEQUENCE: 27

Met Pro Ser Asn Pro Pro Lys Ser Ser Leu Val Val His Arg Ile Asn
1               5                   10                  15

Ser Pro Asn Ser Ile Thr Thr Ala Thr Thr Ala Ser Ala Ala Ala Asn
            20                  25                  30

Asn His Asn Thr Ser Thr Met Pro Pro His Lys Gln Val Pro Asp Ala
        35                  40                  45

Val Ser Arg His His Thr His Val Val Gly Pro Asn Gln Cys Cys Ser
    50                  55                  60

Ala Val Val Gln Gln Ile Ala Ala Pro Val Ser Thr Val Trp Ser Val

```
                65                  70                  75                  80
Val Arg Arg Phe Asp Asn Pro Gln Ala Tyr Lys His Phe Val Lys Ser
                    85                  90                  95

Cys His Val Val Val Gly Asp Gly Asp Val Gly Thr Leu Arg Glu Val
                100                 105                 110

His Val Ile Ser Gly Leu Pro Ala Ala Asn Ser Thr Glu Arg Leu Glu
                115                 120                 125

Ile Leu Asp Asp Glu Arg His Val Leu Ser Phe Ser Val Ile Gly Gly
        130                 135                 140

Asp His Arg Leu Ser Asn Tyr Arg Ser Val Thr Thr Leu His Pro Ser
145                 150                 155                 160

Pro Ser Ser Thr Gly Thr Val Val Leu Glu Ser Tyr Val Val Asp Ile
                165                 170                 175

Pro Pro Gly Asn Thr Lys Glu Asp Thr Cys Val Phe Val Asp Thr Ile
                180                 185                 190

Val Arg Cys Asn Leu Gln Ser Leu Ala Gln Ile Ala Glu Asn Ala Ala
                195                 200                 205

Gly Cys Lys Arg Ser Ser Ser
        210                 215

<210> SEQ ID NO 28
<211> LENGTH: 213
<212> TYPE: PRT
<213> ORGANISM: Nicotiana tabacum
<220> FEATURE:
<223> OTHER INFORMATION: tobacco hypothetical protein, gene c17, GenBank
      Accession No. CAI84653.1

<400> SEQUENCE: 28

Met Pro Pro Ser Ser Pro Asp Ser Ser Val Leu Leu Gln Arg Ile Ser
1               5                   10                  15

Ser Asn Thr Thr Pro Asp Phe Ala Cys Lys Gln Ser Gln Gln Leu Gln
                20                  25                  30

Arg Arg Thr Met Pro Ile Pro Cys Thr Thr Gln Val Pro Asp Ser Val
            35                  40                  45

Val Arg Phe His Thr His Pro Val Gly Pro Asn Gln Cys Cys Ser Ala
        50                  55                  60

Val Ile Gln Arg Ile Ser Ala Pro Val Ser Thr Val Trp Ser Val Val
65                  70                  75                  80

Arg Arg Phe Asp Asn Pro Gln Ala Tyr Lys His Phe Val Lys Ser Cys
                    85                  90                  95

His Val Ile Val Gly Asp Gly Asp Val Gly Thr Leu Arg Glu Val Arg
                100                 105                 110

Val Ile Ser Gly Leu Pro Ala Ala Ser Ser Thr Glu Arg Leu Glu Ile
                115                 120                 125

Leu Asp Asp Glu Arg His Val Ile Ser Phe Ser Val Val Gly Gly Asp
        130                 135                 140

His Arg Leu Ala Asn Tyr Arg Ser Val Thr Thr Leu His Pro Glu Pro
145                 150                 155                 160

Ser Gly Asp Gly Thr Thr Ile Val Val Glu Ser Tyr Val Val Asp Val
                165                 170                 175

Pro Pro Gly Asn Thr Arg Asp Glu Thr Cys Val Phe Val Asp Thr Ile
                180                 185                 190

Val Lys Cys Asn Leu Thr Ser Leu Ser Gln Ile Ala Val Asn Val Asn
                195                 200                 205
```

Arg Arg Lys Asp Ser
        210

<210> SEQ ID NO 29
<211> LENGTH: 208
<212> TYPE: PRT
<213> ORGANISM: Oryza sativa
<220> FEATURE:
<223> OTHER INFORMATION: rice Indica Group, cultivar 93-11, hypothetical
      protein OsI_04285, GenBank Accession No. EAY76350.1

<400> SEQUENCE: 29

Met Pro Tyr Ala Ala Val Arg Pro Ser Pro Pro Gln Leu Ser Arg
1               5                   10                  15

Pro Ile Gly Ser Gly Ala Gly Gly Lys Ala Cys Pro Ala Val Pro
                20                  25                  30

Cys Glu Val Ala Arg Tyr His Glu His Ala Val Gly Ala Gly Gln Cys
                35                  40                  45

Cys Ser Thr Val Val Gln Ala Ile Ala Ala Pro Ala Asp Ala Val Trp
        50                  55                  60

Ser Val Val Arg Arg Phe Asp Arg Pro Gln Ala Tyr Lys Lys Phe Ile
65                  70                  75                  80

Lys Ser Cys Arg Leu Val Asp Gly Asp Gly Gly Glu Val Gly Ser Val
                85                  90                  95

Arg Glu Val Arg Val Val Ser Gly Leu Pro Ala Thr Ser Ser Arg Glu
                100                 105                 110

Arg Leu Glu Val Leu Asp Asp Arg Arg Val Leu Ser Phe Arg Ile
                115                 120                 125

Val Gly Gly Glu His Arg Leu Ala Asn Tyr Arg Ser Val Thr Thr Val
        130                 135                 140

His Glu Ala Ala Ala Pro Ala Met Ala Val Val Val Glu Ser Tyr Val
145                 150                 155                 160

Val Asp Val Pro Pro Gly Asn Thr Trp Glu Glu Thr Arg Val Phe Val
                165                 170                 175

Asp Thr Ile Val Arg Cys Asn Leu Gln Ser Leu Ala Arg Thr Val Glu
                180                 185                 190

Arg Leu Ala Pro Glu Ala Pro Arg Ala Asn Gly Ser Ile Asp His Ala
                195                 200                 205

<210> SEQ ID NO 30
<211> LENGTH: 208
<212> TYPE: PRT
<213> ORGANISM: Oryza sativa
<220> FEATURE:
<223> OTHER INFORMATION: rice Japonica Group, cultivar Nipponbare,
      Bet v I allergen-like protein, gene B1088C09.11, clone B1088C09,
      GenBank Accession No. BAB68102.1

<400> SEQUENCE: 30

Met Pro Tyr Ala Ala Val Arg Pro Ser Pro Pro Gln Leu Ser Arg
1               5                   10                  15

Pro Ile Gly Ser Gly Ala Gly Gly Lys Ala Cys Pro Ala Val Pro
                20                  25                  30

Cys Glu Val Ala Arg Tyr His Glu His Ala Val Gly Ala Gly Gln Cys
                35                  40                  45

Phe Ser Thr Val Val Gln Ala Ile Ala Ala Pro Ala Asp Ala Val Trp
        50                  55                  60

Ser Val Val Arg Arg Phe Asp Arg Pro Gln Ala Tyr Lys Lys Phe Ile
65                  70                  75                  80

```
Lys Ser Cys Arg Leu Val Asp Gly Asp Gly Glu Val Gly Ser Val
                85                  90                  95

Arg Glu Val Arg Val Val Ser Gly Leu Pro Ala Thr Ser Ser Arg Glu
            100                 105                 110

Arg Leu Glu Val Leu Asp Asp Arg Arg Val Leu Ser Phe Arg Ile
            115                 120                 125

Val Gly Gly Glu His Arg Leu Ala Asn Tyr Arg Ser Val Thr Thr Val
            130                 135                 140

His Glu Ala Ala Ala Pro Ala Met Ala Val Val Glu Ser Tyr Val
145                 150                 155                 160

Val Asp Val Pro Pro Gly Asn Thr Trp Glu Glu Thr Arg Val Phe Val
                165                 170                 175

Asp Thr Ile Val Arg Cys Asn Leu Gln Ser Leu Ala Arg Thr Val Glu
            180                 185                 190

Arg Leu Ala Pro Glu Ala Pro Arg Ala Asn Gly Ser Ile Asp His Ala
            195                 200                 205

<210> SEQ ID NO 31
<211> LENGTH: 213
<212> TYPE: PRT
<213> ORGANISM: Picea sitchensis
<220> FEATURE:
<223> OTHER INFORMATION: Sitka spruce cultivar FB3-425, unknown protein,
      clone WS0276_P02, GenBank Accession No. ABK22940.1

<400> SEQUENCE: 31

Met Asp Ile Ile Ala Gly Phe Asp Gln Leu Ser Phe Arg Leu Ser Gly
1               5                   10                  15

Ala Ser Lys Gln Ile Thr Lys Thr Gly Ala Val Gln Tyr Leu Lys Gly
            20                  25                  30

Glu Glu Gly Tyr Gly Glu Trp Leu Lys Glu Val Met Gly Arg Tyr His
        35                  40                  45

Tyr His Ser His Asp Gly Ala Arg Glu Cys Arg Cys Ser Ser Val Val
50                  55                  60

Val Gln Gln Val Glu Ala Pro Val Ser Val Val Trp Ser Leu Val Arg
65                  70                  75                  80

Arg Phe Asp Gln Pro Gln Val Tyr Lys His Phe Val Ser Asn Cys Phe
                85                  90                  95

Met Arg Gly Asp Leu Lys Val Gly Cys Leu Arg Glu Val Arg Val Val
            100                 105                 110

Ser Gly Leu Pro Ala Ala Thr Ser Thr Glu Arg Leu Asp Ile Leu Asp
            115                 120                 125

Glu Glu Arg His Ile Leu Ser Phe Ser Ile Val Gly Gly Asp His Arg
        130                 135                 140

Leu Asn Asn Tyr Arg Ser Ile Thr Thr Leu His Glu Thr Leu Ile Asn
145                 150                 155                 160

Gly Lys Pro Gly Thr Ile Val Ile Glu Ser Tyr Val Leu Asp Val Pro
                165                 170                 175

His Gly Asn Thr Lys Glu Glu Thr Cys Leu Phe Val Asp Thr Ile Val
            180                 185                 190

Lys Cys Asn Leu Gln Ser Leu Ala His Val Ser Asn His Leu Asn Ser
            195                 200                 205

Thr His Arg Cys Leu
            210
```

```
<210> SEQ ID NO 32
<211> LENGTH: 207
<212> TYPE: PRT
<213> ORGANISM: Oryza sativa
<220> FEATURE:
<223> OTHER INFORMATION: rice Japonica Group, cultivar Nipponbare,
      hypothetical protein Os06g0562200, Bet v I allergen family
      protein, GenBank Accession No. NP_001057874.1

<400> SEQUENCE: 32
```

Met Glu Ala His Val Glu Arg Ala Leu Arg Glu Gly Leu Thr Glu Glu
1               5                   10                  15

Glu Arg Ala Ala Leu Glu Pro Ala Val Met Ala His His Thr Phe Pro
                20                  25                  30

Pro Ser Thr Thr Thr Ala Thr Thr Ala Ala Thr Cys Thr Ser Leu
            35                  40                  45

Val Thr Gln Arg Val Ala Ala Pro Val Arg Ala Val Trp Pro Ile Val
    50                  55                  60

Arg Ser Phe Gly Asn Pro Gln Arg Tyr Lys His Phe Val Arg Thr Cys
65                  70                  75                  80

Ala Leu Ala Ala Gly Asp Gly Ala Ser Val Gly Ser Val Arg Glu Val
                85                  90                  95

Thr Val Val Ser Gly Leu Pro Ala Ser Thr Ser Thr Glu Arg Leu Glu
            100                 105                 110

Met Leu Asp Asp Asp Arg His Ile Ile Ser Phe Arg Val Val Gly Gly
            115                 120                 125

Gln His Arg Leu Arg Asn Tyr Arg Ser Val Thr Ser Val Thr Glu Phe
        130                 135                 140

Gln Pro Pro Ala Ala Gly Pro Gly Pro Ala Pro Pro Tyr Cys Val Val
145                 150                 155                 160

Val Glu Ser Tyr Val Val Asp Val Pro Asp Gly Asn Thr Ala Glu Asp
                165                 170                 175

Thr Arg Met Phe Thr Asp Thr Val Val Lys Leu Asn Leu Gln Met Leu
            180                 185                 190

Ala Ala Val Ala Glu Asp Ser Ser Ser Ala Ser Arg Arg Arg Asp
        195                 200                 205

```
<210> SEQ ID NO 33
<211> LENGTH: 216
<212> TYPE: PRT
<213> ORGANISM: Oryza sativa
<220> FEATURE:
<223> OTHER INFORMATION: rice Japonica Group, cultivar Nipponbare,
      hypothetical protein Os05g0473000, Streptomyces cyclase/dehydrase
      family protein, GenBank Accession No. NP_001055819.1

<400> SEQUENCE: 33
```

Met Pro Tyr Thr Ala Pro Arg Pro Ser Pro Gln His Ser Arg Ile
1               5                   10                  15

Gly Gly Cys Gly Gly Gly Gly Val Leu Lys Ala Ala Gly Ala Ala Gly
                20                  25                  30

His Ala Ala Ser Cys Val Ala Val Pro Ala Glu Val Ala Arg His His
            35                  40                  45

Glu His Ala Ala Gly Val Gly Gln Cys Cys Ser Ala Val Val Gln Ala
        50                  55                  60

Ile Ala Ala Pro Val Asp Ala Val Trp Ser Val Val Arg Arg Phe Asp
65                  70                  75                  80

Arg Pro Gln Ala Tyr Lys His Phe Ile Arg Ser Cys Arg Leu Leu Asp
                85                  90                  95

Gly Asp Gly Asp Gly Ala Val Ala Val Gly Ser Val Arg Glu Val
            100                 105                 110

Arg Val Val Ser Gly Leu Pro Ala Thr Ser Ser Arg Glu Arg Leu Glu
        115                 120                 125

Ile Leu Asp Asp Glu Arg Arg Val Leu Ser Phe Arg Val Val Gly Gly
    130                 135                 140

Glu His Arg Leu Ser Asn Tyr Arg Ser Val Thr Thr Val His Glu Thr
145                 150                 155                 160

Ala Ala Gly Ala Ala Ala Val Val Glu Ser Tyr Val Asp
                165                 170                 175

Val Pro His Gly Asn Thr Ala Asp Glu Thr Arg Met Phe Val Asp Thr
            180                 185                 190

Ile Val Arg Cys Asn Leu Gln Ser Leu Ala Arg Thr Ala Glu Gln Leu
        195                 200                 205

Ala Leu Ala Ala Pro Arg Ala Ala
    210                 215

<210> SEQ ID NO 34
<211> LENGTH: 212
<212> TYPE: PRT
<213> ORGANISM: Vitis vinifera
<220> FEATURE:
<223> OTHER INFORMATION: wine grape cultivar PN40024 unnamed protein
      product, locus tag GSVIVT00029365001, GenBank Accession No.
      CAO41436.1

<400> SEQUENCE: 34

Met Pro Ser Ser Leu Gln Leu His Arg Ile Asn Asn Ile Asp Pro Thr
1               5                   10                  15

Thr Val Ala Val Ala Ala Thr Ala Ala Val Asn Cys His Lys Gln Ser
            20                  25                  30

Arg Thr Pro Leu Arg Cys Ala Thr Pro Val Pro Asp Ala Val Ala Ser
        35                  40                  45

Tyr His Ala His Ala Val Gly Pro His Gln Cys Cys Ser Met Val Val
    50                  55                  60

Gln Thr Thr Ala Ala Ala Leu Pro Thr Val Trp Ser Val Val Arg Arg
65                  70                  75                  80

Phe Asp Asn Pro Gln Ala Tyr Lys His Phe Leu Lys Ser Cys His Val
                85                  90                  95

Ile Phe Gly Asp Gly Asp Ile Gly Thr Leu Arg Glu Val His Val Val
            100                 105                 110

Ser Gly Leu Pro Ala Glu Ser Ser Thr Glu Arg Leu Glu Ile Leu Asp
        115                 120                 125

Asp Glu Arg His Val Leu Ser Phe Ser Val Val Gly Gly Asp His Arg
    130                 135                 140

Leu Cys Asn Tyr Arg Ser Val Thr Thr Leu His Pro Ser Pro Thr Gly
145                 150                 155                 160

Thr Gly Thr Val Val Val Glu Ser Tyr Val Val Asp Ile Pro Pro Gly
                165                 170                 175

Asn Thr Lys Glu Asp Thr Cys Val Phe Val Asp Thr Ile Val Lys Cys
            180                 185                 190

Asn Leu Gln Ser Leu Ala Gln Met Ser Glu Lys Leu Thr Asn Asn Asn
        195                 200                 205

Arg Asn Ser Ser
    210

-continued

```
<210> SEQ ID NO 35
<211> LENGTH: 218
<212> TYPE: PRT
<213> ORGANISM: Zea mays
<220> FEATURE:
<223> OTHER INFORMATION: maize cyclase/dehydrase family protein, clone
      1678999, GenBank Accession No. ACG30334.1

<400> SEQUENCE: 35

Met Pro Cys Leu Gln Ala Ser Ser Pro Gly Ser Met Pro Tyr Gln His
1               5                   10                  15

His Gly Arg Gly Val Gly Cys Ala Ala Glu Ala Gly Ala Ala Val Gly
            20                  25                  30

Ala Ser Ala Gly Thr Gly Thr Arg Cys Gly Ala His Asp Gly Glu Val
        35                  40                  45

Pro Ala Glu Ala Ala Arg His His Glu His Ala Ala Pro Gly Pro Gly
    50                  55                  60

Arg Cys Cys Ser Ala Val Val Gln Arg Val Ala Ala Pro Ala Glu Ala
65                  70                  75                  80

Val Trp Ser Val Val Arg Arg Phe Asp Gln Pro Gln Ala Tyr Lys Arg
                85                  90                  95

Phe Val Arg Ser Cys Ala Leu Leu Ala Gly Asp Gly Val Gly Val Gly Thr
            100                 105                 110

Leu Arg Glu Val Arg Val Val Ser Gly Leu Pro Ala Ala Ser Ser Arg
        115                 120                 125

Glu Arg Leu Glu Val Leu Asp Asp Glu Ser His Val Leu Ser Phe Arg
    130                 135                 140

Val Val Gly Gly Glu His Arg Leu Gln Asn Tyr Leu Ser Val Thr Thr
145                 150                 155                 160

Val His Pro Ser Pro Ala Ala Pro Asp Ala Ala Thr Val Val Val Glu
                165                 170                 175

Ser Tyr Val Val Asp Val Pro Pro Gly Asn Thr Pro Glu Asp Thr Arg
            180                 185                 190

Val Phe Val Asp Thr Ile Val Lys Cys Asn Leu Gln Ser Leu Ala Thr
        195                 200                 205

Thr Ala Glu Lys Leu Ala Leu Ala Ala Val
    210                 215

<210> SEQ ID NO 36
<211> LENGTH: 179
<212> TYPE: PRT
<213> ORGANISM: Physcomitrella patens
<220> FEATURE:
<223> OTHER INFORMATION: Physcomitrella patens subsp. patens moss,
      ecotype Gransden 2004, hypothetical protein, predicted protein,
      locus tag PHYPADRAFT_222359, GenBank Accession No. XP_001778048.1

<400> SEQUENCE: 36

Met Gln Thr Lys Gly Arg Gln Ala Asp Phe Gln Thr Leu Leu Glu Gly
1               5                   10                  15

Gln Gln Asp Leu Ile Cys Arg Phe His Arg His Glu Leu Gln Pro His
            20                  25                  30

Gln Cys Gly Ser Ile Leu Leu Gln Leu Ile Lys Ala Pro Val Glu Thr
        35                  40                  45

Val Trp Ser Val Ala Arg Ser Phe Asp Lys Pro Gln Val Tyr Lys Arg
    50                  55                  60

Phe Ile Gln Thr Cys Glu Ile Ile Glu Gly Asp Gly Gly Val Gly Ser
65                  70                  75                  80
```

```
Ile Arg Glu Val Arg Leu Val Ser Ser Ile Pro Ala Thr Ser Ser Ile
                85                  90                  95

Glu Arg Leu Glu Ile Leu Asp Asp Glu His Ile Ile Ser Phe Arg
            100                 105                 110

Val Leu Gly Gly Gly His Arg Leu Gln Asn Tyr Trp Ser Val Thr Ser
            115                 120                 125

Leu His Ser His Glu Ile Asp Gly Gln Met Gly Thr Leu Val Leu Glu
            130                 135                 140

Ser Tyr Val Val Asp Ile Pro Glu Gly Asn Thr Arg Glu Glu Thr His
145                 150                 155                 160

Met Phe Val Asp Thr Val Val Arg Cys Asn Leu Lys Ala Leu Ala Gln
                165                 170                 175

Val Ser Glu

<210> SEQ ID NO 37
<211> LENGTH: 229
<212> TYPE: PRT
<213> ORGANISM: Oryza sativa
<220> FEATURE:
<223> OTHER INFORMATION: rice Indica Group, cultivar 93-11, hypothetical
      protein OsI_11160, GenBank Accession No. EAY89631.1

<400> SEQUENCE: 37

Met Pro Cys Ile Pro Ala Ser Ser Pro Gly Ile Pro His Gln His Gln
1               5                   10                  15

His Gln His His Arg Ala Leu Ala Gly Val Gly Met Ala Val Gly Cys
            20                  25                  30

Ala Ala Glu Ala Ala Val Ala Ala Ala Gly Val Ala Gly Thr Arg Cys
            35                  40                  45

Gly Ala His Asp Gly Glu Val Pro Met Glu Val Ala Arg His His Glu
        50                  55                  60

His Ala Glu Pro Gly Ser Gly Arg Cys Cys Ser Ala Val Val Gln His
65                  70                  75                  80

Val Ala Ala Pro Ala Pro Ala Val Trp Ser Val Val Arg Arg Phe Asp
                85                  90                  95

Gln Pro Gln Ala Tyr Lys Arg Phe Val Arg Ser Cys Ala Leu Leu Ala
            100                 105                 110

Gly Asp Gly Gly Val Gly Thr Leu Arg Glu Val Arg Val Val Ser Gly
            115                 120                 125

Leu Pro Ala Ala Ser Ser Arg Glu Arg Leu Glu Ile Leu Asp Asp Glu
            130                 135                 140

Ser His Val Leu Ser Phe Arg Val Val Gly Gly Glu His Arg Leu Lys
145                 150                 155                 160

Asn Tyr Leu Ser Val Thr Thr Val His Pro Ser Pro Ser Ala Pro Thr
                165                 170                 175

Ala Ala Thr Val Val Val Glu Ser Tyr Val Val Asp Val Pro Pro Gly
            180                 185                 190

Asn Thr Pro Glu Asp Thr Arg Val Phe Val Asp Thr Ile Val Lys Cys
            195                 200                 205

Asn Leu Gln Ser Leu Ala Lys Thr Ala Glu Lys Leu Ala Ala Gly Ala
            210                 215                 220

Arg Ala Ala Gly Ser
225

<210> SEQ ID NO 38
```

<211> LENGTH: 229
<212> TYPE: PRT
<213> ORGANISM: Oryza sativa
<220> FEATURE:
<223> OTHER INFORMATION: rice Japonica Group, cultivar Nipponbare, hypothetical protein Os03g0297600, Streptomyces cyclase/dehydrase family protein, GenBank Accession No. NP_001049838.1

<400> SEQUENCE: 38

```
Met Pro Cys Ile Pro Ala Ser Ser Pro Gly Ile Pro His Gln His Gln
1               5                   10                  15

His Gln His His Arg Ala Leu Ala Gly Val Gly Met Ala Val Gly Cys
            20                  25                  30

Ala Ala Glu Ala Ala Val Ala Ala Gly Val Ala Gly Thr Arg Cys
        35                  40                  45

Gly Ala His Asp Gly Glu Val Pro Met Glu Val Ala Arg His His Glu
    50                  55                  60

His Ala Glu Pro Gly Ser Gly Arg Cys Cys Ser Ala Val Val Gln His
65                  70                  75                  80

Val Ala Ala Pro Ala Ala Ala Val Trp Ser Val Val Arg Arg Phe Asp
                85                  90                  95

Gln Pro Gln Ala Tyr Lys Arg Phe Val Arg Ser Cys Ala Leu Leu Ala
            100                 105                 110

Gly Asp Gly Gly Val Gly Thr Leu Arg Glu Val Arg Val Val Ser Gly
        115                 120                 125

Leu Pro Ala Ala Ser Ser Arg Glu Arg Leu Glu Ile Leu Asp Asp Glu
    130                 135                 140

Ser His Val Leu Ser Phe Arg Val Val Gly Glu His Arg Leu Lys
145                 150                 155                 160

Asn Tyr Leu Ser Val Thr Thr Val His Pro Ser Pro Ser Ala Pro Thr
                165                 170                 175

Ala Ala Thr Val Val Val Glu Ser Tyr Val Val Asp Val Pro Pro Gly
            180                 185                 190

Asn Thr Pro Glu Asp Thr Arg Val Phe Val Asp Thr Ile Val Lys Cys
        195                 200                 205

Asn Leu Gln Ser Leu Ala Lys Thr Ala Glu Lys Leu Ala Ala Gly Ala
    210                 215                 220

Arg Ala Ala Gly Ser
225
```

<210> SEQ ID NO 39
<211> LENGTH: 205
<212> TYPE: PRT
<213> ORGANISM: Medicago truncatula
<220> FEATURE:
<223> OTHER INFORMATION: barrel medic unknown protein, clone MTYFP_FQ_FR_FS1G-H-19, GenBank Accession No. ACJ85898.1

<400> SEQUENCE: 39

```
Met Pro Ser Pro Val Gln Phe Gln Arg Phe Asp Ser Asn Thr Ala Ile
1               5                   10                  15

Thr Asn Gly Val Asn Cys Pro Lys Gln Ile Gln Ala Cys Arg Tyr Ala
            20                  25                  30

Leu Ser Ser Leu Lys Pro Thr Val Ser Val Pro Glu Thr Val Val Asp
        35                  40                  45

His His Met His Val Val Gly Gln Asn Gln Cys Tyr Ser Val Val Ile
    50                  55                  60

Gln Thr Ile Asn Ala Ser Val Ser Thr Val Trp Ser Val Val Arg Arg
```

```
          65                  70                  75                  80
Phe Asp Tyr Pro Gln Gly Tyr Lys His Phe Val Lys Ser Cys Asn Val
                    85                  90                  95

Val Ala Ser Gly Asp Gly Ile Arg Val Gly Ala Leu Arg Glu Val Arg
                100                 105                 110

Leu Val Ser Gly Leu Pro Ala Val Ser Ser Thr Glu Arg Leu Asp Ile
                115                 120                 125

Leu Asp Glu Glu Arg His Val Ile Ser Phe Ser Val Val Gly Gly Val
            130                 135                 140

His Arg Cys Arg Asn Tyr Arg Ser Val Thr Thr Leu His Gly Asp Gly
145                 150                 155                 160

Asn Gly Gly Thr Val Val Ile Glu Ser Tyr Val Val Asp Val Pro Gln
                165                 170                 175

Gly Asn Thr Lys Glu Glu Thr Cys Ser Phe Ala Asp Thr Ile Val Arg
                180                 185                 190

Cys Asn Leu Gln Ser Leu Val Gln Ile Ala Glu Lys Leu
                195                 200                 205
```

<210> SEQ ID NO 40
<211> LENGTH: 212
<212> TYPE: PRT
<213> ORGANISM: Zea mays
<220> FEATURE:
<223> OTHER INFORMATION: maize AT-rich element binding factor 3, clone
      1458362, GenBank Accession No. ACG26321.1

<400> SEQUENCE: 40

```
Met Pro Phe Ala Ala Ser Arg Thr Ser Gln Gln Gln His Ser Arg Val
1               5                   10                  15

Ala Thr Asn Gly Arg Ala Val Ala Val Cys Ala Gly His Ala Gly Val
                20                  25                  30

Pro Asp Glu Val Ala Arg His His Glu His Ala Val Ala Ala Gly Gln
                35                  40                  45

Cys Cys Ala Ala Met Val Gln Ser Ile Ala Ala Pro Val Asp Ala Val
            50                  55                  60

Trp Ser Leu Val Arg Arg Phe Asp Gln Pro Gln Arg Tyr Lys Arg Phe
65                  70                  75                  80

Ile Arg Ser Cys His Leu Val Asp Gly Asp Gly Ala Glu Val Gly Ser
                85                  90                  95

Val Arg Glu Leu Leu Leu Val Ser Gly Leu Pro Ala Glu Ser Ser Arg
                100                 105                 110

Glu Arg Leu Glu Ile Arg Asp Asp Glu Arg Arg Val Ile Ser Phe Arg
            115                 120                 125

Val Leu Gly Gly Asp His Arg Leu Ala Asn Tyr Arg Ser Val Thr Thr
        130                 135                 140

Val His Glu Ala Ala Pro Ser Gln Asp Gly Arg Pro Leu Thr Met Val
145                 150                 155                 160

Val Glu Ser Tyr Val Val Asp Val Pro Pro Gly Asn Thr Val Glu Glu
                165                 170                 175

Thr Arg Ile Phe Val Asp Thr Ile Val Arg Cys Asn Leu Gln Ser Leu
                180                 185                 190

Glu Gly Thr Val Ile Arg Gln Leu Glu Ile Ala Ala Met Pro His Asp
            195                 200                 205

Asp Asn Gln Asn
        210
```

```
<210> SEQ ID NO 41
<211> LENGTH: 233
<212> TYPE: PRT
<213> ORGANISM: Zea mays
<220> FEATURE:
<223> OTHER INFORMATION: maize strain B73 unknown protein, clone
      ZM_BFb0105O18, GenBank Accession No. ACF87013.1

<400> SEQUENCE: 41

Met Arg Glu Arg Asn Ser Ser Ile Asp Gln Glu His Gln Arg Gly Ser
1               5                   10                  15

Ser Ser Arg Ser Thr Met Pro Phe Ala Ala Ser Arg Thr Ser Gln Gln
            20                  25                  30

Gln His Ser Arg Val Ala Thr Asn Gly Arg Ala Val Ala Val Cys Ala
        35                  40                  45

Gly His Ala Gly Val Pro Asp Glu Val Ala Arg His His Glu His Ala
    50                  55                  60

Val Ala Ala Gly Gln Cys Cys Ala Ala Met Val Gln Ser Ile Ala Ala
65                  70                  75                  80

Pro Val Asp Ala Val Trp Ser Leu Val Arg Arg Phe Asp Gln Pro Gln
                85                  90                  95

Arg Tyr Lys Arg Phe Ile Arg Ser Cys His Leu Val Asp Gly Asp Gly
            100                 105                 110

Ala Glu Val Gly Ser Val Arg Glu Leu Leu Leu Val Ser Gly Leu Pro
        115                 120                 125

Ala Glu Ser Ser Arg Glu Arg Leu Glu Ile Arg Asp Asp Glu Arg Arg
    130                 135                 140

Val Ile Ser Phe Arg Val Leu Gly Gly Asp His Arg Leu Ala Asn Tyr
145                 150                 155                 160

Arg Ser Val Thr Thr Val His Glu Ala Ala Pro Ser Gln Asp Gly Arg
                165                 170                 175

Pro Leu Thr Met Val Val Glu Ser Tyr Val Val Asp Val Pro Pro Gly
            180                 185                 190

Asn Thr Val Glu Glu Thr Arg Ile Phe Val Asp Thr Ile Val Arg Cys
        195                 200                 205

Asn Leu Gln Ser Leu Glu Gly Thr Val Ile Arg Gln Leu Glu Ile Ala
    210                 215                 220

Ala Met Pro His Asp Asp Asn Gln Asn
225                 230

<210> SEQ ID NO 42
<211> LENGTH: 194
<212> TYPE: PRT
<213> ORGANISM: Physcomitrella patens
<220> FEATURE:
<223> OTHER INFORMATION: Physcomitrella patens subsp. patens moss,
      ecotype Gransden 2004, hypothetical protein, predicted protein,
      locus tag PHYPADRAFT_209242, GenBank Accession No. XP_001762113.1

<400> SEQUENCE: 42

Met Met Gln Glu Lys Gln Gly Arg Pro Asp Phe Gln Phe Leu Leu Glu
1               5                   10                  15

Gly Gln Gln Asp Leu Ile Cys Arg Phe His Lys His Glu Leu Leu Pro
            20                  25                  30

His Gln Cys Gly Ser Ile Leu Leu Gln Gln Ile Lys Ala Pro Val Gln
        35                  40                  45

Thr Val Trp Leu Ile Val Arg Arg Phe Asp Glu Pro Gln Val Tyr Lys
    50                  55                  60
```

```
Arg Phe Ile Gln Arg Cys Asp Ile Val Glu Gly Asp Gly Val Val Gly
 65                  70                  75                  80

Ser Ile Arg Glu Val Gln Leu Val Ser Ser Ile Pro Ala Thr Ser Ser
                 85                  90                  95

Ile Glu Arg Leu Glu Ile Leu Asp Asp Glu His Ile Ile Ser Phe
            100                 105                 110

Arg Val Leu Gly Gly Gly His Arg Leu Gln Asn Tyr Trp Ser Val Thr
        115                 120                 125

Ser Leu His Arg His Glu Ile Gln Gly Gln Met Gly Thr Leu Val Leu
    130                 135                 140

Glu Ser Tyr Val Val Asp Ile Pro Asp Gly Asn Thr Arg Glu Glu Thr
145                 150                 155                 160

His Thr Phe Val Asp Thr Val Val Arg Cys Asn Leu Lys Ala Leu Ala
                165                 170                 175

Gln Val Ser Glu Gln Lys His Leu Leu Asn Ser Asn Glu Lys Pro Ala
            180                 185                 190

Ala Pro

<210> SEQ ID NO 43
<211> LENGTH: 191
<212> TYPE: PRT
<213> ORGANISM: Vitis vinifera
<220> FEATURE:
<223> OTHER INFORMATION: wine grape cultivar PN40024 unnamed protein
      product, locus tag GSVIVT00035869001, GenBank Accession No.
      CAO48052.1

<400> SEQUENCE: 43

Met Lys Val Tyr Ser Pro Ser Gln Ile Leu Ala Glu Arg Gly Pro Arg
1               5                  10                  15

Ala Gln Ala Met Gly Asn Leu Tyr His Thr His Leu Leu Pro Asn
            20                  25                  30

Gln Cys Ser Ser Leu Val Val Gln Thr Thr Asp Ala Pro Leu Pro Gln
        35                  40                  45

Val Trp Ser Met Val Arg Arg Phe Asp Arg Pro Gln Ser Tyr Lys Arg
 50                  55                  60

Phe Val Arg Gly Cys Thr Leu Arg Arg Gly Lys Gly Val Gly Ser
 65                  70                  75                  80

Val Arg Glu Val Asn Ile Val Ser Gly Leu Pro Ala Glu Ile Ser Leu
                 85                  90                  95

Glu Arg Leu Asp Lys Leu Asp Asp Leu His Val Met Arg Phe Thr
            100                 105                 110

Val Ile Gly Gly Asp His Arg Leu Ala Asn Tyr His Ser Thr Leu Thr
        115                 120                 125

Leu His Glu Asp Glu Asp Gly Val Arg Lys Thr Val Met Glu
    130                 135                 140

Ser Tyr Val Val Asp Val Pro Gly Gly Asn Ser Ala Gly Glu Thr Cys
145                 150                 155                 160

Tyr Phe Ala Asn Thr Ile Ile Gly Phe Asn Leu Lys Ala Leu Ala Ala
                165                 170                 175

Val Thr Glu Thr Met Ala Leu Lys Ala Asn Ile Pro Ser Gly Phe
            180                 185                 190

<210> SEQ ID NO 44
<211> LENGTH: 217
<212> TYPE: PRT
```

<213> ORGANISM: Physcomitrella patens
<220> FEATURE:
<223> OTHER INFORMATION: Physcomitrella patens subsp. patens moss,
    ecotype Gransden 2004, hypothetical protein, predicted protein,
    locus tag PHYPADRAFT_132509, GenBank Accession No. XP_001767821.1

<400> SEQUENCE: 44

```
Met Gln Gln Val Lys Gly Arg Gln Asp Phe Gln Arg Leu Leu Glu Ala
1               5                   10                  15

Gln Gln Asp Leu Ile Cys Arg Tyr His Thr His Glu Leu Lys Ala His
            20                  25                  30

Gln Cys Gly Ser Ile Leu Leu Gln Gln Ile Lys Val Pro Leu Pro Ile
        35                  40                  45

Val Trp Ala Ile Val Arg Ser Phe Asp Lys Pro Gln Val Tyr Lys Arg
    50                  55                  60

Phe Ile Gln Thr Cys Lys Ile Thr Glu Gly Asp Gly Gly Val Gly Ser
65                  70                  75                  80

Ile Arg Glu Val His Leu Val Ser Ser Val Pro Ala Thr Cys Ser Ile
                85                  90                  95

Glu Arg Leu Glu Ile Leu Asp Asp Gly Lys His Ile Ile Ser Phe Arg
            100                 105                 110

Val Leu Gly Gly Gly His Arg Leu Gln Asn Tyr Ser Ser Val Ser Ser
        115                 120                 125

Leu His Glu Leu Glu Val Glu Gly His Pro Cys Thr Leu Val Leu Glu
    130                 135                 140

Ser Tyr Met Val Asp Ile Pro Asp Gly Asn Thr Arg Glu Glu Thr His
145                 150                 155                 160

Met Phe Val Asp Thr Val Val Arg Cys Asn Leu Lys Ser Leu Ala Gln
                165                 170                 175

Ile Ser Glu Gln Gln Tyr Asn Lys Asp Cys Leu Gln Gln Lys Gln His
            180                 185                 190

Asp Gln Gln Gln Met Tyr Gln Gln Arg His Pro Pro Leu Pro Pro Ile
        195                 200                 205

Pro Ile Thr Asp Lys Asn Met Glu Arg
    210                 215
```

<210> SEQ ID NO 45
<211> LENGTH: 195
<212> TYPE: PRT
<213> ORGANISM: Physcomitrella patens
<220> FEATURE:
<223> OTHER INFORMATION: Physcomitrella patens subsp. patens moss,
    ecotype Gransden 2004, hypothetical protein, predicted protein,
    locus tag PHYPADRAFT_213389, GenBank Accession No. XP_001767012.1

<400> SEQUENCE: 45

```
Met Arg Phe Asp Ile Gly His Asn Asp Val Arg Gly Phe Phe Thr Cys
1               5                   10                  15

Glu Glu Glu His Ala Tyr Ala Leu His Ser Gln Thr Val Glu Leu Asn
            20                  25                  30

Gln Cys Gly Ser Ile Leu Met Gln Gln Ile His Ala Pro Ile Glu Val
        35                  40                  45

Val Trp Ser Ile Val Arg Ser Phe Gly Ser Pro Gln Ile Tyr Lys Lys
    50                  55                  60

Phe Ile Gln Ala Cys Ile Leu Thr Val Gly Asp Gly Gly Val Gly Ser
65                  70                  75                  80

Ile Arg Glu Val Phe Leu Val Ser Gly Val Pro Ala Thr Ser Ser Ile
                85                  90                  95
```

```
Glu Arg Leu Glu Ile Leu Asp Asp Glu Lys His Val Phe Ser Phe Arg
            100                 105                 110

Val Leu Lys Gly Gly His Arg Leu Gln Asn Tyr Arg Ser Val Thr Thr
            115                 120                 125

Leu His Glu Gln Glu Val Asn Gly Arg Gln Thr Thr Thr Val Leu Glu
        130                 135                 140

Ser Tyr Val Val Asp Val Pro Asp Gly Asn Thr Arg Glu Glu Thr His
145                 150                 155                 160

Met Phe Ala Asp Thr Val Val Met Cys Asn Leu Lys Ser Leu Ala Gln
                165                 170                 175

Val Ala Glu Trp Arg Ala Met Gln Gly Ile Thr Gln Gln Leu Ser Thr
            180                 185                 190

Ser Ser Leu
        195

<210> SEQ ID NO 46
<211> LENGTH: 172
<212> TYPE: PRT
<213> ORGANISM: Vitis vinifera
<220> FEATURE:
<223> OTHER INFORMATION: wine grape cultivar Pinot Noir hypothetical
      protein, clone ENTAV 115, locus tag VITISV_004947, GenBank
      Accession No. CAN72620.1

<400> SEQUENCE: 46

Met Gly Asn Leu Tyr His Thr His His Leu Leu Pro Asn Gln Cys Ser
1               5                   10                  15

Ser Leu Val Val Gln Thr Thr Asp Ala Pro Leu Pro Gln Val Trp Ser
            20                  25                  30

Met Val Arg Arg Phe Asp Arg Pro Gln Ser Tyr Lys Arg Phe Val Arg
        35                  40                  45

Gly Cys Thr Leu Arg Arg Gly Lys Gly Gly Val Gly Ser Val Arg Glu
    50                  55                  60

Val Asn Ile Val Ser Gly Leu Pro Ala Glu Ile Ser Leu Glu Arg Leu
65                  70                  75                  80

Asp Lys Leu Asp Asp Leu His Val Met Arg Phe Thr Val Ile Gly
                85                  90                  95

Gly Asp His Arg Leu Ala Asn Tyr His Ser Thr Leu Thr Leu His Glu
            100                 105                 110

Asp Glu Glu Asp Gly Val Arg Lys Thr Val Val Met Glu Ser Tyr Val
        115                 120                 125

Val Asp Val Pro Gly Gly Asn Ser Ala Gly Glu Thr Cys Tyr Phe Ala
    130                 135                 140

Asn Thr Ile Ile Gly Phe Asn Leu Lys Ala Leu Ala Ala Val Thr Glu
145                 150                 155                 160

Thr Met Ala Leu Lys Ala Asn Ile Pro Ser Gly Phe
                165                 170

<210> SEQ ID NO 47
<211> LENGTH: 196
<212> TYPE: PRT
<213> ORGANISM: Picea sitchensis
<220> FEATURE:
<223> OTHER INFORMATION: Sitka spruce cultivar FB3-425, unknown protein,
      clone WS0281_I24, GenBank Accession No. ABK23752.1

<400> SEQUENCE: 47

Met Glu Asp Leu Ser Ser Trp Arg Glu Gly Arg Ala Met Trp Leu Gly
```

```
              1               5                  10                 15
Asn Pro Pro Ser Glu Ser Glu Leu Val Cys Arg His His Arg His Glu
                20                  25                 30
Leu Gln Gly Asn Gln Cys Ser Ser Phe Leu Val Lys His Ile Arg Ala
                35                  40                 45
Pro Val His Leu Val Trp Ser Ile Val Arg Thr Phe Asp Gln Pro Gln
 50                 55                  60
Lys Tyr Lys Pro Phe Val His Ser Cys Ser Val Arg Gly Gly Ile Thr
 65                 70                  75                 80
Val Gly Ser Ile Arg Asn Val Asn Val Lys Ser Gly Leu Pro Ala Thr
                85                  90                 95
Ala Ser Glu Glu Arg Leu Glu Ile Leu Asp Asp Asn Glu His Val Phe
                100                 105                110
Ser Ile Lys Ile Leu Gly Gly Asp His Arg Leu Gln Asn Tyr Ser Ser
                115                 120                125
Ile Ile Thr Val His Pro Glu Ile Ile Asp Gly Arg Pro Gly Thr Leu
                130                 135                140
Val Ile Glu Ser Tyr Val Val Asp Val Pro Glu Gly Asn Thr Arg Glu
145                 150                 155                160
Glu Thr Arg Phe Phe Val Glu Ala Leu Val Lys Cys Asn Leu Lys Ser
                165                 170                175
Leu Ala Asp Val Ser Glu Arg Leu Ala Ser Gln His His Thr Glu Leu
                180                 185                190
Leu Glu Arg Thr
            195

<210> SEQ ID NO 48
<211> LENGTH: 185
<212> TYPE: PRT
<213> ORGANISM: Solanum tuberosum
<220> FEATURE:
<223> OTHER INFORMATION: potato cultivar Kuras, CAPIP1-like protein,
      clone 153D02, similar to Casicum annuum CAPIP1, GenBank Accession
      No. ABB29920.1

<400> SEQUENCE: 48

Met Asn Ala Asn Gly Phe Cys Gly Val Glu Lys Glu Tyr Ile Arg Lys
1               5                   10                 15
His His Leu His Glu Pro Lys Glu Asn Gln Cys Ser Ser Phe Leu Val
                20                  25                 30
Lys His Ile Arg Ala Pro Val His Leu Val Trp Ser Leu Val Arg Arg
                35                  40                 45
Phe Asp Gln Pro Gln Lys Tyr Lys Pro Phe Ile Ser Arg Cys Ile Val
 50                 55                  60
Gln Gly Asp Leu Glu Ile Gly Ser Leu Arg Glu Val Asp Val Lys Ser
 65                 70                  75                 80
Gly Leu Pro Ala Thr Thr Ser Thr Glu Arg Leu Glu Leu Leu Asp Asp
                85                  90                 95
Glu Glu His Ile Leu Ser Val Arg Ile Val Gly Gly Asp His Arg Leu
                100                 105                110
Arg Asn Tyr Ser Ser Val Ile Ser Val His Pro Glu Val Ile Asp Gly
                115                 120                125
Arg Pro Gly Thr Val Val Leu Glu Ser Phe Val Val Asp Val Pro Glu
                130                 135                140
Gly Asn Thr Lys Asp Glu Thr Cys Tyr Phe Val Glu Ala Leu Ile Asn
145                 150                 155                160
```

```
Cys Asn Leu Lys Ser Leu Ala Asp Ile Ser Glu Arg Val Ala Val Gln
                165                 170                 175

Asp Arg Thr Glu Pro Ile Asp Gln Val
            180                 185

<210> SEQ ID NO 49
<211> LENGTH: 190
<212> TYPE: PRT
<213> ORGANISM: Medicago truncatula
<220> FEATURE:
<223> OTHER INFORMATION: barrel medic unknown protein, clone
      MTYFP_FQ_FR_FS1G-E-17, GenBank Accession No. ACJ85952.1

<400> SEQUENCE: 49

Met Asn Asn Gly Cys Glu Gln Gln Gln Tyr Ser Val Ile Glu Thr Gln
1               5                   10                  15

Tyr Ile Arg Arg His His Lys His Asp Leu Arg Asp Asn Gln Cys Ser
                20                  25                  30

Ser Ala Leu Val Lys His Ile Lys Ala Pro Val His Leu Val Trp Ser
            35                  40                  45

Leu Val Arg Arg Phe Asp Gln Pro Gln Lys Tyr Lys Pro Phe Ile Ser
50                  55                  60

Arg Cys Ile Met Gln Gly Asp Leu Ser Ile Gly Ser Val Arg Glu Val
65                  70                  75                  80

Asn Val Lys Ser Gly Leu Pro Ala Thr Thr Ser Thr Glu Arg Leu Glu
                85                  90                  95

Gln Leu Asp Asp Glu Glu His Ile Leu Gly Ile Arg Ile Val Gly Gly
            100                 105                 110

Asp His Arg Leu Arg Asn Tyr Ser Ser Ile Ile Thr Val His Pro Gly
        115                 120                 125

Val Ile Asp Gly Arg Pro Gly Thr Met Val Ile Glu Ser Phe Val Val
130                 135                 140

Asp Val Pro Glu Gly Asn Thr Lys Asp Glu Thr Cys Tyr Phe Val Glu
145                 150                 155                 160

Ala Leu Ile Arg Tyr Asn Leu Ser Ser Leu Ala Asp Val Ser Glu Arg
                165                 170                 175

Met Ala Val Gln Gly Arg Thr Asp Pro Ile Asn Ile Asn Pro
            180                 185                 190

<210> SEQ ID NO 50
<211> LENGTH: 185
<212> TYPE: PRT
<213> ORGANISM: Vitis vinifera
<220> FEATURE:
<223> OTHER INFORMATION: wine grape cultivar PN40024 unnamed protein
      product, locus tag GSVIVT00002440001, GenBank Accession No.
      CAO65816.1

<400> SEQUENCE: 50

Met Ser Gly Tyr Gly Cys Ile Lys Met Glu Asp Glu Tyr Ile Arg Arg
1               5                   10                  15

His His Arg His Glu Ile Arg Asp Asn Gln Cys Ser Ser Ser Leu Val
                20                  25                  30

Lys His Ile Lys Ala Pro Val His Leu Val Trp Ser Leu Val Arg Ser
            35                  40                  45

Phe Asp Gln Pro Gln Lys Tyr Lys Pro Phe Val Ser Arg Cys Ile Val
50                  55                  60

Gln Gly Asp Leu Glu Ile Gly Ser Val Arg Glu Val Asn Val Lys Ser
```

```
                65                  70                  75                  80

Gly Leu Pro Ala Thr Thr Ser Thr Glu Arg Leu Glu Leu Leu Asp Asp
                    85                  90                  95

Glu Glu His Ile Phe Gly Met Arg Ile Val Gly Gly Asp His Arg Leu
                100                 105                 110

Lys Asn Tyr Ser Ser Ile Val Thr Val His Pro Glu Ile Ile Asp Gly
                115                 120                 125

Arg Pro Gly Thr Leu Val Ile Glu Ser Phe Val Val Asp Val Pro Asp
            130                 135                 140

Gly Asn Thr Lys Asp Glu Thr Cys Tyr Phe Val Glu Ala Leu Ile Lys
145                 150                 155                 160

Cys Asn Leu Lys Ser Leu Ala Asp Val Ser Glu Arg Leu Ala Ile Gln
                165                 170                 175

Asp Arg Thr Glu Pro Ile Asp Arg Met
            180                 185

<210> SEQ ID NO 51
<211> LENGTH: 185
<212> TYPE: PRT
<213> ORGANISM: Vitis vinifera
<220> FEATURE:
<223> OTHER INFORMATION: wine grape cultivar PN40024 unnamed protein
      product, locus tag GSVIVT00006507001, GenBank Accession No.
      CAO69376.1

<400> SEQUENCE: 51

Met Asn Gly Asn Gly Leu Ser Ser Met Glu Ser Glu Tyr Ile Arg Arg
1               5                   10                  15

His His Arg His Glu Pro Ala Glu Asn Gln Cys Ser Ser Ala Leu Val
                20                  25                  30

Lys His Ile Lys Ala Pro Val Pro Leu Val Trp Ser Leu Val Arg Arg
            35                  40                  45

Phe Asp Gln Pro Gln Lys Tyr Lys Pro Phe Ile Ser Arg Cys Val Val
 50                 55                  60

Gln Gly Asn Leu Glu Ile Gly Ser Leu Arg Glu Val Asp Val Lys Ser
65                  70                  75                  80

Gly Leu Pro Ala Thr Thr Ser Thr Glu Arg Leu Glu Leu Leu Asp Asp
                    85                  90                  95

Asp Glu His Ile Leu Ser Met Arg Ile Ile Gly Gly Asp His Arg Leu
                100                 105                 110

Arg Asn Tyr Ser Ser Ile Ile Ser Leu His Pro Glu Ile Ile Asp Gly
                115                 120                 125

Arg Pro Gly Thr Met Val Ile Glu Ser Tyr Val Val Asp Val Pro Glu
            130                 135                 140

Gly Asn Thr Lys Asp Glu Thr Cys Tyr Phe Val Glu Ala Leu Ile Lys
145                 150                 155                 160

Cys Asn Leu Lys Ser Leu Ala Asp Val Ser Glu Arg Leu Ala Val Gln
                165                 170                 175

Asp Arg Thr Glu Pro Ile Asp Arg Met
            180                 185

<210> SEQ ID NO 52
<211> LENGTH: 208
<212> TYPE: PRT
<213> ORGANISM: Oryza sativa
<220> FEATURE:
<223> OTHER INFORMATION: rice Japonica Group, cultivar Nipponbare,
      hypothetical protein OsJ_21703, GenBank Accession No. EAZ37364.1
```

<400> SEQUENCE: 52

```
Met Glu Ala His Val Glu Arg Ala Leu Arg Glu Gly Leu Thr Glu Glu
1               5                   10                  15

Glu Arg Ala Ala Leu Glu Pro Ala Val Met Ala His His Thr Phe Pro
            20                  25                  30

Pro Ser Thr Thr Thr Ala Thr Thr Ala Ala Ala Thr Cys Thr Ser Leu
        35                  40                  45

Val Thr Gln Arg Val Ala Ala Pro Val Arg Ala Val Trp Pro Ile Val
    50                  55                  60

Arg Ser Phe Gly Asn Pro Gln Arg Tyr Lys His Phe Val Arg Thr Cys
65                  70                  75                  80

Ala Leu Ala Ala Gly Asn Gly Pro Ser Phe Gly Ser Val Arg Glu Val
                85                  90                  95

Thr Val Val Ser Gly Pro Ser Arg Leu Pro Pro Gly Thr Glu Arg Leu
            100                 105                 110

Glu Met Leu Asp Asp Asp Arg His Ile Ile Ser Phe Arg Val Val Gly
        115                 120                 125

Gly Gln His Arg Leu Arg Asn Tyr Arg Ser Val Thr Ser Val Thr Glu
    130                 135                 140

Phe Gln Pro Pro Ala Ala Gly Pro Gly Pro Ala Pro Pro Tyr Cys Val
145                 150                 155                 160

Val Val Glu Ser Tyr Val Val Asp Val Pro Asp Gly Asn Thr Ala Glu
                165                 170                 175

Asp Thr Arg Met Phe Thr Asp Thr Val Val Lys Leu Asn Leu Gln Met
            180                 185                 190

Leu Ala Ala Val Ala Glu Asp Ser Ser Ser Ala Ser Arg Arg Arg Asp
        195                 200                 205
```

<210> SEQ ID NO 53
<211> LENGTH: 186
<212> TYPE: PRT
<213> ORGANISM: Capsicum annuum
<220> FEATURE:
<223> OTHER INFORMATION: pepper cultivar hanbyul, CAPIP1 protein, GenBank Accession No. AAT35532.1

<400> SEQUENCE: 53

```
Met Met Asn Ala Asn Gly Phe Ser Gly Val Glu Lys Glu Tyr Ile Arg
1               5                   10                  15

Lys His His Leu His Gln Pro Lys Glu Asn Gln Cys Ser Ser Phe Leu
            20                  25                  30

Val Lys His Ile Arg Ala Pro Val His Leu Val Trp Ser Leu Val Arg
        35                  40                  45

Arg Phe Asp Gln Pro Gln Lys Tyr Lys Pro Phe Val Ser Arg Cys Ile
    50                  55                  60

Ala Gln Gly Asp Leu Glu Ile Gly Ser Leu Arg Glu Val Asp Val Lys
65                  70                  75                  80

Ser Gly Leu Pro Ala Thr Thr Ser Thr Glu Arg Leu Glu Leu Leu Asp
                85                  90                  95

Asp Glu Glu His Ile Leu Ser Phe Arg Ile Ile Gly Gly Asp His Arg
            100                 105                 110

Leu Arg Asn Tyr Ser Ser Ile Ile Ser Leu His Pro Glu Val Ile Asp
        115                 120                 125

Gly Arg Pro Gly Thr Leu Val Ile Glu Ser Phe Val Val Asp Val Pro
    130                 135                 140
```

Gln Gly Asn Thr Lys Asp Glu Thr Cys Tyr Phe Val Glu Ala Leu Ile
145                 150                 155                 160

Asn Cys Asn Leu Lys Ser Leu Ala Asp Val Ser Glu Arg Leu Ala Val
                165                 170                 175

Gln Asp Arg Thr Glu Pro Ile Asp Gln Val
            180                 185

<210> SEQ ID NO 54
<211> LENGTH: 186
<212> TYPE: PRT
<213> ORGANISM: Populus trichocarpa
<220> FEATURE:
<223> OTHER INFORMATION: California poplar (Western balsam poplar, black
      cottonwood) cultivar 383-2499 (Nisqually-1), unknown protein,
      clone PX0011_1113, GenBank Accession No. ABK92491.1

<400> SEQUENCE: 54

Met Asn Gly Ser Asp Ala Tyr Ser Ala Thr Glu Ala Gln Tyr Val Arg
1               5                   10                  15

Arg His His Lys His Glu Pro Arg Glu Asn Gln Cys Thr Ser Ala Leu
                20                  25                  30

Val Lys His Ile Lys Ala Pro Ala His Leu Val Trp Ser Leu Val Arg
            35                  40                  45

Arg Phe Asp Gln Pro Gln Arg Tyr Lys Pro Phe Val Ser Arg Cys Val
        50                  55                  60

Met Asn Gly Glu Leu Gly Ile Gly Ser Val Arg Glu Val Asn Val Lys
65                  70                  75                  80

Ser Gly Leu Pro Ala Thr Thr Ser Thr Glu Arg Leu Glu Leu Leu Asp
                85                  90                  95

Asp Glu Glu His Ile Leu Gly Val Gln Ile Val Gly Gly Asp His Arg
            100                 105                 110

Leu Lys Asn Tyr Ser Ser Ile Met Thr Val His Pro Glu Phe Ile Asp
        115                 120                 125

Gly Arg Pro Gly Thr Leu Val Ile Glu Ser Phe Ile Val Asp Val Pro
    130                 135                 140

Asp Gly Asn Thr Lys Asp Glu Thr Cys Tyr Phe Val Glu Ala Leu Ile
145                 150                 155                 160

Arg Cys Asn Leu Lys Ser Leu Ala Asp Val Ser Glu Arg Met Ala Val
                165                 170                 175

Gln Asp Arg Val Glu Pro Val Asn Gln Phe
            180                 185

<210> SEQ ID NO 55
<211> LENGTH: 185
<212> TYPE: PRT
<213> ORGANISM: Capsicum annuum
<220> FEATURE:
<223> OTHER INFORMATION: pepper cultivar hanbyul, PIP1 protein, GenBank
      Accession No. ABF72432.1

<400> SEQUENCE: 55

Met Asn Ala Asn Gly Phe Ser Gly Val Glu Lys Glu Tyr Ile Arg Lys
1               5                   10                  15

His His Leu His Gln Pro Lys Glu Asn Gln Cys Ser Ser Phe Leu Val
                20                  25                  30

Lys His Ile Arg Ala Pro Val His Leu Val Trp Ser Leu Val Arg Arg
            35                  40                  45

Phe Asp Gln Pro Gln Lys Tyr Lys Pro Phe Val Ser Arg Cys Ile Ala

```
                50                  55                  60
Gln Gly Asp Leu Glu Ile Gly Ser Leu Arg Glu Val Asp Val Lys Ser
 65                  70                  75                  80

Gly Leu Pro Ala Thr Thr Ser Thr Glu Arg Leu Glu Leu Leu Asp Asp
                 85                  90                  95

Glu Glu His Ile Leu Ser Phe Arg Ile Gly Gly Asp His Arg Leu
                100                 105                 110

Arg Asn Tyr Ser Ser Ile Ile Ser Leu His Pro Glu Val Ile Asp Gly
                115                 120                 125

Arg Pro Gly Thr Leu Val Ile Glu Ser Phe Val Val Asp Val Pro Gln
            130                 135                 140

Gly Asn Thr Lys Asp Glu Thr Cys Tyr Phe Val Glu Ala Leu Ile Asn
145                 150                 155                 160

Cys Asn Leu Lys Ser Leu Ala Asp Val Ser Glu Arg Leu Ala Val Gln
                165                 170                 175

Asp Arg Thr Glu Pro Ile Asp Gln Val
            180                 185

<210> SEQ ID NO 56
<211> LENGTH: 186
<212> TYPE: PRT
<213> ORGANISM: Populus trichocarpa x Populus deltoides
<220> FEATURE:
<223> OTHER INFORMATION: California poplar (Western balsam poplar, black
      cottonwood) x Eastern cottonwood, cultivar H11-11, unknown
      protein, clone WS0133_I04, GenBank Accession No. ABK96505.1

<400> SEQUENCE: 56

Met Asn Gly Ser Asp Ala Tyr Ser Ala Thr Glu Ala Gln Tyr Val Arg
 1               5                  10                  15

Arg His His Lys His Glu Pro Arg Glu Asn Gln Cys Thr Ser Ala Leu
                20                  25                  30

Val Lys His Ile Lys Ala Pro Ala His Leu Val Trp Ser Leu Val Arg
             35                  40                  45

Arg Phe Asp Gln Pro Gln Arg Tyr Lys Pro Phe Val Ser Arg Cys Val
         50                  55                  60

Met Asn Gly Glu Leu Gly Ile Gly Ser Val Arg Glu Val Asn Val Lys
 65                  70                  75                  80

Ser Gly Leu Pro Ala Thr Thr Ser Thr Glu Arg Leu Glu Leu Leu Asp
                 85                  90                  95

Asp Glu Glu His Ile Leu Gly Val Gln Ile Val Gly Gly Asp His Arg
                100                 105                 110

Leu Lys Asn Tyr Ser Ser Ile Met Thr Val His Pro Glu Phe Ile Asp
            115                 120                 125

Gly Arg Pro Gly Thr Leu Val Ile Glu Ser Phe Ile Val Asp Val Pro
        130                 135                 140

Asp Gly Asn Thr Lys Asp Glu Thr Cys Tyr Phe Val Lys Ala Leu Ile
145                 150                 155                 160

Arg Cys Asn Leu Lys Ser Leu Ala Asp Val Ser Glu Arg Met Ala Val
                165                 170                 175

Gln Asp Arg Val Glu Pro Val Asn Gln Phe
            180                 185

<210> SEQ ID NO 57
<211> LENGTH: 188
<212> TYPE: PRT
<213> ORGANISM: Pisum sativum
```

<220> FEATURE:
<223> OTHER INFORMATION: pea AT-rich element binding factor 3 (PsATF, ATF3), potential transcription factor, GenBank Accession No. AAV85853.1

<400> SEQUENCE: 57

```
Met Asn Asn Gly Gly Glu Gln Tyr Ser Ala Ile Glu Thr Gln Tyr Ile
1               5                   10                  15

Arg Arg Arg His Lys His Asp Leu Arg Asp Asn Gln Cys Ser Ser Ala
            20                  25                  30

Leu Val Lys His Ile Lys Ala Pro Val His Leu Val Trp Ser Leu Val
        35                  40                  45

Arg Arg Phe Asp Gln Pro Gln Lys Tyr Lys Pro Phe Val Ser Arg Cys
    50                  55                  60

Ile Met Gln Gly Asp Leu Gly Ile Gly Ser Val Arg Glu Val Asn Val
65                  70                  75                  80

Lys Ser Gly Leu Pro Ala Thr Thr Ser Thr Glu Arg Leu Glu Gln Leu
                85                  90                  95

Asp Asp Glu Glu His Ile Leu Gly Ile Arg Ile Val Gly Gly Asp His
            100                 105                 110

Arg Leu Arg Asn Tyr Ser Ser Val Ile Thr Val His Pro Glu Val Ile
        115                 120                 125

Asp Gly Arg Pro Gly Thr Met Val Ile Glu Ser Phe Val Val Asp Val
    130                 135                 140

Pro Glu Gly Asn Thr Arg Asp Glu Thr Cys Tyr Phe Val Glu Ala Leu
145                 150                 155                 160

Ile Arg Gly Asn Leu Ser Ser Leu Ala Asp Val Ser Glu Arg Met Ala
                165                 170                 175

Val Gln Gly Arg Thr Asp Pro Ile Asn Val Asn Pro
            180                 185
```

<210> SEQ ID NO 58
<211> LENGTH: 177
<212> TYPE: PRT
<213> ORGANISM: Vitis vinifera
<220> FEATURE:
<223> OTHER INFORMATION: wine grape cultivar PN40024 unnamed protein product, locus tag GSVIVT00027009001, GenBank Accession No. CAO39744.1

<400> SEQUENCE: 58

```
Met Glu Ala Gln Val Ile Cys Arg His His Ala His Glu Pro Arg Glu
1               5                   10                  15

Asn Gln Cys Ser Ser Val Leu Val Arg His Val Lys Ala Pro Ala Asn
            20                  25                  30

Leu Val Trp Ser Leu Val Arg Arg Phe Asp Gln Pro Gln Lys Tyr Lys
        35                  40                  45

Pro Phe Val Ser Arg Cys Val Val Gln Gly Asp Leu Arg Ile Gly Ser
    50                  55                  60

Val Arg Glu Val Asn Val Lys Thr Gly Leu Pro Ala Thr Thr Ser Thr
65                  70                  75                  80

Glu Arg Leu Glu Leu Phe Asp Asp Asp Glu His Val Leu Gly Ile Lys
                85                  90                  95

Ile Leu Asp Gly Asp His Arg Leu Arg Asn Tyr Ser Ser Val Ile Thr
            100                 105                 110

Val His Pro Glu Ile Ile Asp Gly Arg Pro Gly Thr Leu Val Ile Glu
        115                 120                 125
```

```
Ser Phe Val Val Asp Val Pro Glu Gly Asn Thr Lys Asp Asp Thr Cys
    130                 135                 140

Tyr Phe Val Arg Ala Leu Ile Asn Cys Asn Leu Lys Cys Leu Ala Glu
145                 150                 155                 160

Val Ser Glu Arg Met Ala Met Leu Gly Arg Val Glu Pro Ala Asn Ala
                165                 170                 175

Val

<210> SEQ ID NO 59
<211> LENGTH: 178
<212> TYPE: PRT
<213> ORGANISM: Vitis vinifera
<220> FEATURE:
<223> OTHER INFORMATION: wine grape cultivar Pinot Noir hypothetical
      protein, clone ENTAV 115, locus tag VITISV_004915, GenBank
      Accession No. CAN82501.1

<400> SEQUENCE: 59

Met Met Glu Ala Gln Val Ile Cys Arg His His Ala His Glu Pro Arg
1               5                   10                  15

Glu Asn Gln Cys Ser Ser Val Leu Val Arg His Val Lys Ala Pro Ala
                20                  25                  30

Asn Leu Val Trp Ser Leu Val Arg Arg Phe Asp Gln Pro Gln Lys Tyr
            35                  40                  45

Lys Pro Phe Val Ser Arg Cys Val Val Gln Gly Asp Leu Arg Ile Gly
    50                  55                  60

Ser Val Arg Glu Val Asn Val Lys Thr Gly Leu Pro Ala Thr Thr Ser
65                  70                  75                  80

Thr Glu Arg Leu Glu Leu Phe Asp Asp Asp Glu His Val Leu Gly Ile
                85                  90                  95

Lys Ile Leu Asp Gly Asp His Arg Leu Arg Asn Tyr Ser Ser Val Ile
                100                 105                 110

Thr Val His Pro Glu Ile Ile Asp Gly Arg Pro Gly Thr Leu Val Ile
            115                 120                 125

Glu Ser Phe Val Val Asp Val Pro Glu Gly Asn Thr Lys Asp Asp Thr
    130                 135                 140

Cys Tyr Phe Val Arg Ala Leu Ile Asn Cys Asn Leu Lys Cys Leu Ala
145                 150                 155                 160

Glu Val Ser Glu Arg Met Ala Met Leu Gly Arg Val Glu Pro Ala Asn
                165                 170                 175

Ala Val

<210> SEQ ID NO 60
<211> LENGTH: 193
<212> TYPE: PRT
<213> ORGANISM: Arachis hypogaea
<220> FEATURE:
<223> OTHER INFORMATION: peanut pathogenesis-induced protein (PIP),
      GenBank Accession No. ACG76109.1
<220> FEATURE:
<221> NAME/KEY: VARIANT
<222> LOCATION: (162)...(162)
<223> OTHER INFORMATION: Xaa = any amino acid

<400> SEQUENCE: 60

Met Met Asn Gly Ser Cys Gly Gly Gly Gly Gly Glu Ala Tyr Gly
1               5                   10                  15

Ala Ile Glu Ala Gln Tyr Ile Arg Arg His His Arg His Glu Pro Arg
                20                  25                  30
```

```
Asp Asn Gln Cys Thr Ser Ala Leu Val Lys His Ile Arg Ala Pro Val
            35                  40                  45

His Leu Val Trp Ser Leu Val Arg Arg Phe Asp Gln Pro Gln Lys Tyr
 50                  55                  60

Lys Pro Phe Val Ser Arg Cys Ile Met Gln Gly Asp Leu Gly Ile Gly
 65                  70                  75                  80

Ser Val Arg Glu Val Asn Val Lys Ser Gly Leu Pro Ala Thr Thr Ser
                 85                  90                  95

Thr Glu Arg Leu Glu Gln Leu Asp Asp Glu His Ile Leu Gly Ile
                100                 105                 110

Arg Ile Val Gly Gly Asp His Arg Leu Arg Asn Tyr Ser Ser Ile Ile
                115                 120                 125

Thr Val His Pro Glu Val Ile Glu Gly Arg Pro Gly Thr Met Val Ile
            130                 135                 140

Glu Ser Phe Val Val Asp Val Pro Asp Gly Asn Thr Lys Asp Glu Thr
145                 150                 155                 160

Cys Xaa Phe Val Glu Ala Leu Ile Arg Cys Asn Leu Ser Ser Leu Ala
                165                 170                 175

Asp Val Ser Glu Arg Met Ala Val Gln Gly Arg Thr Asp Pro Ile Asn
                180                 185                 190

Gln

<210> SEQ ID NO 61
<211> LENGTH: 217
<212> TYPE: PRT
<213> ORGANISM: Zea mays
<220> FEATURE:
<223> OTHER INFORMATION: maize AT-rich element binding factor 3, clone
      300908, GenBank Accession No. ACG39386.1

<400> SEQUENCE: 61

Met Val Val Glu Met Asp Gly Val Gly Val Ala Ala Gly Gly Gly Gly
 1               5                  10                  15

Gly Gly Ala Gln Thr Pro Ala Pro Ala Pro Pro Arg Arg Trp Arg Leu
                 20                  25                  30

Ala Asp Glu Arg Cys Asp Leu Arg Ala Met Glu Thr Asp Tyr Val Arg
             35                  40                  45

Arg Phe His Arg His Glu Pro Arg Asp His Gln Cys Ser Ser Ala Val
 50                  55                  60

Ala Lys His Ile Lys Ala Pro Val His Leu Val Trp Ser Leu Val Arg
 65                  70                  75                  80

Arg Phe Asp Gln Pro Gln Leu Phe Lys Pro Phe Val Ser Arg Cys Glu
                 85                  90                  95

Met Lys Gly Asn Ile Glu Ile Gly Ser Val Arg Glu Val Asn Val Lys
                100                 105                 110

Ser Gly Leu Pro Ala Thr Arg Ser Thr Glu Arg Leu Glu Leu Leu Asp
            115                 120                 125

Asp Asp Glu Arg Ile Leu Ser Val Arg Phe Val Gly Gly Asp His Arg
130                 135                 140

Leu Gln Asn Tyr Ser Ser Ile Leu Thr Val His Pro Glu Val Ile Asp
145                 150                 155                 160

Gly Arg Pro Gly Thr Leu Val Ile Glu Ser Phe Val Val Asp Val Pro
                165                 170                 175

Asp Gly Asn Thr Lys Asp Glu Thr Cys Tyr Phe Val Glu Ala Leu Leu
                180                 185                 190
```

Lys Cys Asn Leu Arg Ser Leu Ala Glu Val Ser Glu Gly Gln Val Ile
            195                 200                 205

Met Asp Gln Thr Glu Pro Leu Asp Arg
    210                 215

<210> SEQ ID NO 62
<211> LENGTH: 217
<212> TYPE: PRT
<213> ORGANISM: Zea mays
<220> FEATURE:
<223> OTHER INFORMATION: maize strain B73, unknown protein, clone
      ZM_BFb0036A01, GenBank Accession No. ACF80077.1

<400> SEQUENCE: 62

Met Val Val Glu Met Asp Gly Gly Val Gly Val Ala Ala Ala Gly Gly
1               5                   10                  15

Gly Gly Ala Gln Thr Pro Ala Pro Pro Pro Arg Arg Trp Arg Leu
            20                  25                  30

Ala Asp Glu Arg Cys Asp Leu Arg Ala Met Glu Thr Asp Tyr Val Arg
        35                  40                  45

Arg Phe His Arg His Glu Pro Arg Asp His Gln Cys Ser Ser Ala Val
    50                  55                  60

Ala Lys His Ile Lys Ala Pro Val His Leu Val Trp Ser Leu Val Arg
65                  70                  75                  80

Arg Phe Asp Gln Pro Gln Leu Phe Lys Pro Phe Val Ser Arg Cys Glu
                85                  90                  95

Met Lys Gly Asn Ile Glu Ile Gly Ser Val Arg Glu Val Asn Val Lys
            100                 105                 110

Ser Gly Leu Pro Ala Thr Arg Ser Thr Glu Arg Leu Glu Leu Leu Asp
        115                 120                 125

Asp Asp Glu Arg Ile Leu Ser Val Arg Phe Val Gly Asp His Arg
    130                 135                 140

Leu Gln Asn Tyr Ser Ser Ile Leu Thr Val His Pro Glu Val Ile Asp
145                 150                 155                 160

Gly Arg Pro Gly Thr Leu Val Ile Glu Ser Phe Val Val Asp Val Pro
                165                 170                 175

Asp Gly Asn Thr Lys Asp Glu Thr Cys Tyr Phe Val Glu Ala Leu Leu
            180                 185                 190

Lys Cys Asn Leu Arg Ser Leu Ala Glu Val Ser Glu Gly Gln Val Ile
        195                 200                 205

Met Asp Gln Thr Glu Pro Leu Asp Arg
    210                 215

<210> SEQ ID NO 63
<211> LENGTH: 206
<212> TYPE: PRT
<213> ORGANISM: Oryza sativa
<220> FEATURE:
<223> OTHER INFORMATION: rice Japonica Group, cultivar Nipponbare,
      hypothetical protein Os06g0528300, GenBank Accession No.
      NP_001057772.1

<400> SEQUENCE: 63

Met Asn Gly Val Gly Gly Ala Gly Gly Ala Ala Gly Lys Leu Pro
1               5                   10                  15

Met Val Ser His Arg Arg Val Gln Trp Arg Leu Ala Asp Glu Arg Cys
            20                  25                  30

Glu Leu Arg Glu Glu Glu Met Glu Tyr Ile Arg Arg Phe His Arg His
        35                  40                  45

Glu Pro Ser Ser Asn Gln Cys Thr Ser Phe Ala Ala Lys His Ile Lys
                50                  55                  60

Ala Pro Leu His Thr Val Trp Ser Leu Val Arg Arg Phe Asp Gln Pro
 65                  70                  75                  80

Gln Leu Phe Lys Pro Phe Val Arg Asn Cys Val Met Arg Glu Asn Ile
                 85                  90                  95

Ile Ala Thr Gly Cys Ile Arg Glu Val Asn Val Gln Ser Gly Leu Pro
                100                 105                 110

Ala Thr Arg Ser Thr Glu Arg Leu Glu Leu Leu Asp Asp Asn Glu His
                115                 120                 125

Ile Leu Lys Val Asn Phe Ile Gly Gly Asp His Met Leu Lys Asn Tyr
                130                 135                 140

Ser Ser Ile Leu Thr Val His Ser Glu Val Ile Asp Gly Gln Leu Gly
145                 150                 155                 160

Thr Leu Val Val Glu Ser Phe Ile Val Asp Val Pro Glu Gly Asn Thr
                165                 170                 175

Lys Asp Asp Ile Ser Tyr Phe Ile Glu Asn Val Leu Arg Cys Asn Leu
                180                 185                 190

Arg Thr Leu Ala Asp Val Ser Glu Glu Arg Leu Ala Asn Pro
                195                 200                 205

<210> SEQ ID NO 64
<211> LENGTH: 206
<212> TYPE: PRT
<213> ORGANISM: Oryza sativa
<220> FEATURE:
<223> OTHER INFORMATION: rice Indica Group, cultivar 93-11, hypothetical
      protein OsI_23215, GenBank Accession No. EAZ01188.1

<400> SEQUENCE: 64

Met Asn Gly Ala Gly Gly Ala Gly Gly Ala Ala Ala Gly Lys Leu Pro
 1               5                  10                  15

Met Val Ser His Arg Gln Val Gln Trp Arg Leu Ala Asp Glu Arg Cys
                 20                  25                  30

Glu Leu Arg Glu Glu Glu Met Glu Tyr Ile Arg Gln Phe His Arg His
                 35                  40                  45

Glu Pro Ser Ser Asn Gln Cys Thr Ser Phe Val Ala Lys His Ile Lys
                 50                  55                  60

Ala Pro Leu Gln Thr Val Trp Ser Leu Val Arg Arg Phe Asp Gln Pro
 65                  70                  75                  80

Gln Leu Phe Lys Pro Phe Val Arg Lys Cys Val Met Arg Glu Asn Ile
                 85                  90                  95

Ile Ala Thr Gly Cys Val Arg Glu Val Asn Val Gln Ser Gly Leu Pro
                100                 105                 110

Ala Thr Arg Ser Thr Glu Arg Leu Glu Leu Leu Asp Asp Asn Glu His
                115                 120                 125

Ile Leu Lys Val Lys Phe Ile Gly Gly Asp His Met Leu Lys Asn Tyr
                130                 135                 140

Ser Ser Ile Leu Thr Ile His Ser Glu Val Ile Asp Gly Gln Leu Gly
145                 150                 155                 160

Thr Leu Val Val Glu Ser Phe Val Val Asp Ile Pro Glu Gly Asn Thr
                165                 170                 175

Lys Asp Asp Ile Cys Tyr Phe Ile Glu Asn Ile Leu Arg Cys Asn Leu
                180                 185                 190

Met Thr Leu Ala Asp Val Ser Glu Glu Arg Leu Ala Asn Pro

```
              195                 200                 205
```

<210> SEQ ID NO 65
<211> LENGTH: 205
<212> TYPE: PRT
<213> ORGANISM: Oryza sativa
<220> FEATURE:
<223> OTHER INFORMATION: rice Japonica Group, cultivar Nipponbare,
      hypothetical protein OsJ_06125, GenBank Accession No. EAZ22456.1

<400> SEQUENCE: 65

```
Met Val Glu Val Gly Gly Gly Ala Ala Glu Ala Ala Ala Gly Arg Arg
1               5                   10                  15

Trp Arg Leu Ala Asp Glu Arg Cys Asp Leu Arg Ala Ala Glu Thr Glu
            20                  25                  30

Tyr Val Arg Arg Phe His Arg His Glu Pro Arg Asp His Gln Cys Ser
        35                  40                  45

Ser Ala Val Ala Lys His Ile Lys Ala Pro Val His Leu Val Trp Ser
    50                  55                  60

Leu Val Arg Arg Phe Asp Gln Pro Gln Leu Phe Lys Pro Phe Val Ser
65                  70                  75                  80

Arg Cys Glu Met Lys Gly Asn Ile Glu Ile Gly Ser Val Arg Glu Val
                85                  90                  95

Asn Val Lys Ser Gly Leu Pro Ala Thr Arg Ser Thr Glu Arg Leu Glu
            100                 105                 110

Leu Leu Asp Asp Asn Glu His Ile Leu Ser Val Arg Phe Val Gly Gly
        115                 120                 125

Asp His Arg Leu Lys Asn Tyr Ser Ser Ile Leu Thr Val His Pro Glu
    130                 135                 140

Val Ile Asp Gly Arg Pro Gly Thr Leu Val Ile Glu Ser Phe Val Val
145                 150                 155                 160

Asp Val Pro Glu Gly Asn Thr Lys Asp Glu Thr Cys Tyr Phe Val Glu
                165                 170                 175

Ala Leu Leu Lys Cys Asn Leu Lys Ser Leu Ala Glu Val Ser Glu Arg
            180                 185                 190

Leu Val Cys Gln Gly Pro Asn Arg Ala Pro Ser Thr Arg
        195                 200                 205
```

<210> SEQ ID NO 66
<211> LENGTH: 204
<212> TYPE: PRT
<213> ORGANISM: Oryza sativa
<220> FEATURE:
<223> OTHER INFORMATION: rice Japonica Group, cultivar Nipponbare,
      hypothetical protein Os02g0255500, similar to extensin (fragment),
      GenBank Accession No. NP_001046464.1

<400> SEQUENCE: 66

```
Met Val Glu Val Gly Gly Gly Ala Ala Glu Ala Ala Ala Gly Arg Arg
1               5                   10                  15

Trp Arg Leu Ala Asp Glu Arg Cys Asp Leu Arg Ala Ala Glu Thr Glu
            20                  25                  30

Tyr Val Arg Arg Phe His Arg His Glu Pro Arg Asp His Gln Cys Ser
        35                  40                  45

Ser Ala Val Ala Lys His Ile Lys Ala Pro Val His Leu Val Trp Ser
    50                  55                  60

Leu Val Arg Arg Phe Asp Gln Pro Gln Leu Phe Lys Pro Phe Val Ser
65                  70                  75                  80
```

```
Arg Cys Glu Met Lys Gly Asn Ile Glu Ile Gly Ser Val Arg Glu Val
                85                  90                  95

Asn Val Lys Ser Gly Leu Pro Ala Thr Arg Ser Thr Glu Arg Leu Glu
            100                 105                 110

Leu Leu Asp Asp Asn Glu His Ile Leu Ser Val Arg Phe Val Gly Gly
            115                 120                 125

Asp His Arg Leu Lys Asn Tyr Ser Ser Ile Leu Thr Val His Pro Glu
            130                 135                 140

Val Ile Asp Gly Arg Pro Gly Thr Leu Val Ile Glu Ser Phe Val Val
145                 150                 155                 160

Asp Val Pro Glu Gly Asn Thr Lys Asp Glu Thr Cys Tyr Phe Val Glu
                165                 170                 175

Ala Leu Leu Lys Cys Asn Leu Lys Ser Leu Ala Glu Val Ser Glu Arg
            180                 185                 190

Leu Val Val Lys Asp Gln Thr Glu Pro Leu Asp Arg
            195                 200

<210> SEQ ID NO 67
<211> LENGTH: 199
<212> TYPE: PRT
<213> ORGANISM: Medicago truncatula
<220> FEATURE:
<223> OTHER INFORMATION: barrel medic unknown protein, clone
      MTYFP_FQ_FR_FS1G-G-11, GenBank Accession No. ACJ86004.1

<400> SEQUENCE: 67

Met Glu Lys Met Asn Gly Thr Glu Asn Gly Val Phe Asn Ser Thr
1               5                   10                  15

Glu Met Glu Tyr Ile Arg Arg His His Asn Gln Gln Pro Gly Glu Asn
                20                  25                  30

Gln Cys Ser Ser Ala Leu Val Lys His Ile Arg Ala Pro Val Pro Leu
            35                  40                  45

Val Trp Ser Leu Val Arg Arg Phe Asp Gln Pro Gln Lys Tyr Lys Pro
50                  55                  60

Phe Val Ser Arg Cys Val Val Arg Gly Asn Leu Glu Ile Gly Ser Leu
65                  70                  75                  80

Arg Glu Val Asp Val Lys Ser Gly Leu Pro Ala Thr Thr Ser Thr Glu
                85                  90                  95

Arg Leu Glu Val Leu Asp Asp Asn Glu His Ile Leu Ser Ile Arg Ile
            100                 105                 110

Ile Gly Gly Asp His Arg Leu Arg Asn Tyr Ser Ser Ile Met Ser Leu
            115                 120                 125

His Pro Glu Ile Ile Asp Gly Arg Pro Gly Thr Leu Val Ile Glu Ser
            130                 135                 140

Phe Val Val Asp Val Pro Glu Gly Asn Thr Lys Asp Glu Thr Cys Tyr
145                 150                 155                 160

Phe Val Glu Ala Leu Ile Lys Cys Asn Leu Lys Ser Leu Ser Asp Val
                165                 170                 175

Ser Glu Gly His Ala Val Gln Asp Leu Thr Glu Pro Leu Asp Arg Val
            180                 185                 190

His Glu Leu Leu Ile Ser Gly
            195

<210> SEQ ID NO 68
<211> LENGTH: 199
<212> TYPE: PRT
<213> ORGANISM: Medicago truncatula
```

-continued

<220> FEATURE:
<223> OTHER INFORMATION: barrel medic unknown protein, clone
      MTYF1_F2_F3_FY1G-K-4, GenBank Accession No. ACJ83958.1

<400> SEQUENCE: 68

Met Glu Lys Met Asn Gly Thr Glu Asn Gly Val Phe Asn Ser Thr
1               5                   10                  15

Glu Met Glu Tyr Ile Arg Arg His His Asn Gln Gln Pro Gly Glu Asn
            20                  25                  30

Gln Cys Ser Ser Ala Leu Val Lys His Ile Arg Ala Pro Val Pro Leu
        35                  40                  45

Val Trp Ser Leu Val Arg Arg Phe Asp Gln Pro Gln Lys Tyr Lys Pro
50                  55                  60

Phe Val Ser Arg Cys Val Val Arg Gly Asn Leu Glu Ile Gly Ser Leu
65                  70                  75                  80

Arg Glu Val Asp Val Lys Ser Gly Leu Pro Ala Thr Thr Ser Thr Glu
                85                  90                  95

Arg Leu Glu Val Leu Asp Asp Asn Glu His Ile Leu Ser Ile Arg Ile
            100                 105                 110

Ile Gly Gly Asp His Arg Leu Arg Asn Tyr Ser Ser Ile Met Ser Leu
        115                 120                 125

His Pro Glu Ile Ile Asp Gly Arg Pro Gly Thr Leu Val Ile Glu Ser
130                 135                 140

Phe Val Asp Val Pro Glu Gly Asn Thr Lys Asp Glu Thr Cys Tyr
145                 150                 155                 160

Phe Val Glu Ala Leu Ile Lys Cys Asn Leu Lys Ser Leu Ser Asp Val
                165                 170                 175

Ser Glu Gly His Ala Ala Gln Asp Leu Thr Glu Pro Leu Asp Arg Met
            180                 185                 190

His Glu Leu Leu Ile Ser Gly
        195

<210> SEQ ID NO 69
<211> LENGTH: 197
<212> TYPE: PRT
<213> ORGANISM: Zea mays
<220> FEATURE:
<223> OTHER INFORMATION: maize CAPIP1 protein, clone 244179, GenBank
      Accession No. ACG34726.1

<400> SEQUENCE: 69

Met Val Gly Leu Val Gly Gly Ser Thr Ala Arg Ala Glu His Val Val
1               5                   10                  15

Ala Asn Ala Gly Gly Glu Ala Glu Tyr Val Arg Arg Met His Arg His
            20                  25                  30

Ala Pro Thr Glu His Gln Cys Thr Ser Thr Leu Val Lys His Ile Lys
        35                  40                  45

Ala Pro Val His Leu Val Trp Gln Leu Val Arg Arg Phe Asp Gln Pro
50                  55                  60

Gln Arg Tyr Lys Pro Phe Val Arg Asn Cys Val Val Arg Gly Asp Gln
65                  70                  75                  80

Leu Glu Val Gly Ser Leu Arg Asp Val Asn Val Lys Thr Gly Leu Pro
                85                  90                  95

Ala Thr Thr Ser Thr Glu Arg Leu Glu Gln Leu Asp Asp Asp Leu His
            100                 105                 110

Ile Leu Gly Val Lys Phe Val Gly Gly Asp His Arg Leu Gln Asn Tyr
        115                 120                 125

```
Ser Ser Ile Ile Thr Val His Pro Glu Ser Ile Asp Gly Arg Pro Gly
        130                 135                 140

Thr Leu Val Ile Glu Ser Phe Val Val Asp Val Pro Asp Gly Asn Thr
145                 150                 155                 160

Lys Asp Glu Thr Cys Tyr Phe Val Glu Ala Val Ile Lys Cys Asn Leu
                165                 170                 175

Asn Ser Leu Ala Glu Val Ser Glu Gln Leu Ala Val Glu Ser Pro Thr
            180                 185                 190

Ser Leu Ile Asp Gln
        195

<210> SEQ ID NO 70
<211> LENGTH: 197
<212> TYPE: PRT
<213> ORGANISM: Zea mays
<220> FEATURE:
<223> OTHER INFORMATION: maize CAPIP1 protein, clone 1448906, GenBank
      Accession No. ACG26022.1

<400> SEQUENCE: 70

Met Val Gly Leu Val Gly Gly Ser Thr Ala Arg Ala Glu His Val Val
1               5                   10                  15

Ala Asn Ala Gly Gly Glu Ala Glu Tyr Val Arg Arg Met His Arg His
            20                  25                  30

Ala Pro Thr Glu His Gln Cys Thr Ser Thr Leu Val Lys His Ile Lys
        35                  40                  45

Ala Pro Val His Leu Val Trp Glu Leu Val Arg Arg Phe Asp Gln Pro
    50                  55                  60

Gln Arg Tyr Lys Pro Phe Val Arg Asn Cys Val Val Arg Gly Asp Gln
65                  70                  75                  80

Leu Glu Val Gly Ser Leu Arg Asp Val Asn Val Lys Thr Gly Leu Pro
                85                  90                  95

Ala Thr Thr Ser Thr Glu Arg Leu Glu Gln Leu Asp Asp Asp Leu His
            100                 105                 110

Ile Leu Gly Val Lys Phe Val Gly Gly Asp His Arg Leu Gln Asn Tyr
        115                 120                 125

Ser Ser Ile Ile Thr Val His Pro Glu Ser Ile Asp Gly Arg Pro Gly
    130                 135                 140

Thr Leu Val Ile Glu Ser Phe Val Val Asp Val Pro Asp Gly Asn Thr
145                 150                 155                 160

Lys Asp Glu Thr Cys Tyr Phe Val Glu Ala Val Ile Lys Cys Asn Leu
                165                 170                 175

Asn Ser Leu Ala Glu Val Ser Glu Gln Leu Ala Val Glu Ser Pro Thr
            180                 185                 190

Ser Leu Ile Asp Gln
        195

<210> SEQ ID NO 71
<211> LENGTH: 212
<212> TYPE: PRT
<213> ORGANISM: Zea mays
<220> FEATURE:
<223> OTHER INFORMATION: maize strain B73 unknown protein, clone
      ZM_BFc0183D21, GenBank Accession No. ACF86162.1

<400> SEQUENCE: 71

Met Val Met Val Glu Met Asp Gly Gly Val Gly Gly Gly Gly Gly Gly
1               5                   10                  15
```

Gly Gln Thr Pro Ala Pro Arg Arg Trp Arg Leu Ala Asp Glu Arg Cys
            20                  25                  30

Asp Leu Arg Ala Met Glu Thr Asp Tyr Val Arg Arg Phe His Arg His
        35                  40                  45

Glu Pro Arg Glu His Gln Cys Ser Ser Ala Val Ala Lys His Ile Lys
    50                  55                  60

Ala Pro Val His Leu Val Trp Ser Leu Val Arg Arg Phe Asp Gln Pro
65                  70                  75                  80

Gln Leu Phe Lys Pro Phe Val Ser Arg Cys Glu Met Lys Gly Asn Ile
                85                  90                  95

Glu Ile Gly Ser Val Arg Glu Val Asn Val Lys Ser Gly Leu Pro Ala
            100                 105                 110

Thr Arg Ser Thr Glu Arg Leu Glu Leu Leu Asp Asp Asn Glu His Ile
        115                 120                 125

Leu Ser Val Arg Phe Val Gly Gly Asp His Arg Leu Gln Asn Tyr Ser
    130                 135                 140

Ser Ile Leu Thr Val His Pro Glu Val Ile Asp Gly Arg Pro Gly Thr
145                 150                 155                 160

Leu Val Ile Glu Ser Phe Val Val Asp Val Pro Asp Gly Asn Thr Lys
                165                 170                 175

Asp Glu Thr Cys Tyr Phe Val Glu Ala Leu Leu Lys Cys Asn Leu Lys
            180                 185                 190

Ser Leu Ala Glu Val Ser Glu Arg Gln Val Val Lys Asp Gln Thr Glu
        195                 200                 205

Pro Leu Asp Arg
    210

<210> SEQ ID NO 72
<211> LENGTH: 205
<212> TYPE: PRT
<213> ORGANISM: Oryza sativa
<220> FEATURE:
<223> OTHER INFORMATION: rice Japonica Group, cultivar Nipponbare,
      conserved hypothetical protein Os06g0527800, GenBank Accession No.
      NP_001057771.1

<400> SEQUENCE: 72

Met Asn Gly Ala Gly Gly Ala Gly Gly Ala Ala Gly Lys Leu Pro
1               5                   10                  15

Met Val Ser His Arg Arg Val Gln Cys Arg Leu Ala Asp Lys Arg Cys
            20                  25                  30

Glu Leu Arg Glu Glu Glu Met Glu Tyr Ile Arg Gln Phe His Arg His
        35                  40                  45

Glu Pro Ser Ser Asn Gln Cys Thr Ser Phe Val Ala Lys His Ile Lys
    50                  55                  60

Ala Pro Leu Gln Thr Val Trp Ser Leu Val Arg Arg Phe Asp Gln Pro
65                  70                  75                  80

Gln Leu Phe Lys Pro Phe Val Arg Lys Cys Val Met Arg Glu Asn Ile
                85                  90                  95

Ile Val Thr Gly Cys Val Arg Glu Val Asn Val Gln Ser Gly Leu Pro
            100                 105                 110

Ala Thr Arg Ser Thr Glu Arg Leu Glu Leu Leu Asp Asp Asn Glu His
        115                 120                 125

Ile Leu Lys Val Lys Phe Ile Gly Gly Asp His Met Leu Lys Asn Tyr
    130                 135                 140

```
Ser Ser Ile Leu Thr Ile His Ser Glu Val Ile Asp Gly Gln Leu Gly
145                 150                 155                 160

Thr Leu Val Val Glu Ser Phe Val Val Asp Ile Pro Asp Gly Asn Thr
                165                 170                 175

Lys Asp Asp Ile Cys Tyr Phe Ile Glu Asn Val Leu Arg Cys Asn Leu
            180                 185                 190

Met Thr Leu Ala Asp Val Ser Glu Glu Arg Leu Ala Asn
        195                 200                 205
```

<210> SEQ ID NO 73
<211> LENGTH: 197
<212> TYPE: PRT
<213> ORGANISM: Zea mays
<220> FEATURE:
<223> OTHER INFORMATION: maize strain B73 unknown protein, clone ZM_BFc0063E17, GenBank Accession No. ACF85073.1

<400> SEQUENCE: 73

```
Met Val Gly Leu Val Gly Gly Ser Thr Ala Arg Ala Glu His Val Val
1               5                   10                  15

Ala Asn Ala Gly Gly Glu Thr Glu Tyr Val Arg Arg Leu His Arg His
            20                  25                  30

Ala Pro Ala Glu His Gln Cys Thr Ser Thr Leu Val Lys His Ile Lys
        35                  40                  45

Ala Pro Val His Leu Val Trp Glu Leu Val Arg Ser Phe Asp Gln Pro
    50                  55                  60

Gln Arg Tyr Lys Pro Phe Val Arg Asn Cys Val Val Arg Gly Asp Gln
65                  70                  75                  80

Leu Glu Val Gly Ser Leu Arg Asp Val Asn Val Lys Thr Gly Leu Pro
                85                  90                  95

Ala Thr Thr Ser Thr Glu Arg Leu Glu Gln Leu Asp Asp Asp Leu His
            100                 105                 110

Ile Leu Gly Val Lys Phe Val Gly Gly Asp His Arg Leu Gln Asn Tyr
        115                 120                 125

Ser Ser Ile Ile Thr Val His Pro Glu Ser Ile Asp Gly Arg Pro Gly
    130                 135                 140

Thr Leu Val Ile Glu Ser Phe Val Val Asp Val Pro Asp Gly Asn Thr
145                 150                 155                 160

Lys Asp Glu Thr Cys Tyr Phe Val Glu Ala Val Ile Lys Cys Asn Leu
                165                 170                 175

Lys Ser Leu Ala Glu Val Ser Glu Gln Leu Ala Val Glu Ser Pro Thr
            180                 185                 190

Ser Pro Ile Asp Gln
        195
```

<210> SEQ ID NO 74
<211> LENGTH: 206
<212> TYPE: PRT
<213> ORGANISM: Oryza sativa
<220> FEATURE:
<223> OTHER INFORMATION: rice Indica Group, cultivar 93-11, hypothetical protein OsI_23218, GenBank Accession No. EAZ01191.1

<400> SEQUENCE: 74

```
Met Asn Gly Val Gly Gly Ala Gly Gly Ala Ala Ala Gly Lys Leu Pro
1               5                   10                  15

Met Val Ser His Arg Arg Val Gln Trp Arg Leu Ala Asp Glu Arg Cys
            20                  25                  30
```

-continued

```
Glu Leu Arg Glu Glu Met Glu Tyr Ile Arg Arg Phe His Arg His
         35                  40                  45

Glu Pro Ser Ser Asn Gln Cys Thr Ser Phe Ala Ala Lys His Ile Lys
 50                  55                  60

Ala Pro Leu His Thr Val Trp Ser Leu Val Arg Arg Phe Asp Gln Pro
 65                  70                  75                  80

Gln Leu Phe Lys Pro Phe Val Arg Asn Cys Val Met Arg Glu Asn Ile
                 85                  90                  95

Ile Ala Thr Gly Cys Ile Arg Glu Val Asn Val Gln Ser Gly Leu Pro
            100                 105                 110

Ala Thr Arg Ser Thr Glu Arg Leu Glu Leu Leu Asp Asp Asn Glu His
            115                 120                 125

Ile Leu Lys Val Lys Phe Ile Gly Gly Asp His Met Leu Lys Asn Tyr
130                 135                 140

Ser Ser Ile Leu Thr Val His Ser Glu Val Ile Asp Gly Gln Leu Gly
145                 150                 155                 160

Thr Leu Val Val Glu Ser Phe Ile Val Asp Val Leu Glu Gly Asn Thr
                165                 170                 175

Lys Asp Asp Ile Ser Tyr Phe Ile Glu Asn Val Leu Arg Cys Asn Leu
            180                 185                 190

Arg Thr Leu Ala Asp Val Ser Glu Glu Arg Leu Ala Asn Pro
            195                 200                 205

<210> SEQ ID NO 75
<211> LENGTH: 209
<212> TYPE: PRT
<213> ORGANISM: Oryza sativa
<220> FEATURE:
<223> OTHER INFORMATION: rice Japonica Group, cultivar Nipponbare,
      conserved hypothetical protein Os05g0213500, GenBank Accession No.
      NP_001054923.1

<400> SEQUENCE: 75

Met Val Gly Leu Val Gly Gly Gly Gly Trp Arg Val Gly Asp Asp Ala
 1               5                  10                  15

Ala Gly Gly Gly Gly Gly Ala Val Ala Gly Ala Ala Ala Ala
            20                  25                  30

Ala Glu Ala Glu His Met Arg Arg Leu His Ser His Ala Pro Gly Glu
         35                  40                  45

His Gln Cys Ser Ser Ala Leu Val Lys His Ile Lys Ala Pro Val His
 50                  55                  60

Leu Val Trp Ser Leu Val Arg Ser Phe Asp Gln Pro Gln Arg Tyr Lys
 65                  70                  75                  80

Pro Phe Val Ser Arg Cys Val Val Arg Gly Gly Asp Leu Glu Ile Gly
                 85                  90                  95

Ser Val Arg Glu Val Asn Val Lys Thr Gly Leu Pro Ala Thr Thr Ser
            100                 105                 110

Thr Glu Arg Leu Glu Leu Leu Asp Asp Glu His Ile Leu Ser Val
            115                 120                 125

Lys Phe Val Gly Gly Asp His Arg Leu Arg Asn Tyr Ser Ser Ile Val
130                 135                 140

Thr Val His Pro Glu Ser Ile Asp Gly Arg Pro Gly Thr Leu Val Ile
145                 150                 155                 160

Glu Ser Phe Val Val Asp Val Pro Asp Gly Asn Thr Lys Asp Glu Thr
                165                 170                 175

Cys Tyr Phe Val Glu Ala Val Ile Lys Cys Asn Leu Thr Ser Leu Ala
```

```
                    180                 185                 190

Glu Val Ser Glu Arg Leu Ala Val Gln Ser Pro Thr Ser Pro Leu Glu
            195                 200                 205

Gln

<210> SEQ ID NO 76
<211> LENGTH: 180
<212> TYPE: PRT
<213> ORGANISM: Oryza sativa
<220> FEATURE:
<223> OTHER INFORMATION: rice Japonica Group, cultivar Nipponbare,
      Bet v I allergen-like protein, clone OSJNBa0052K15, gene
      OSJNBa0052K15.17, GenBank Accession No. BAD29692.1

<400> SEQUENCE: 76

Met Val Glu Met Asp Ala Gly Gly Arg Pro Glu Pro Ser Pro Pro Ser
1               5                   10                  15

Gly Gln Cys Ser Ser Ala Val Thr Met Arg Ile Asn Ala Pro Val His
            20                  25                  30

Leu Val Trp Ser Ile Val Arg Arg Phe Glu Glu Pro His Ile Phe Gln
        35                  40                  45

Pro Phe Val Arg Gly Cys Thr Met Arg Gly Ser Thr Ser Leu Ala Val
    50                  55                  60

Gly Cys Val Arg Glu Val Asp Phe Lys Ser Gly Phe Pro Ala Lys Ser
65                  70                  75                  80

Ser Val Glu Arg Leu Glu Ile Leu Asp Asp Lys Glu His Val Phe Gly
                85                  90                  95

Val Arg Ile Ile Gly Gly Asp His Arg Leu Lys Asn Tyr Ser Ser Val
            100                 105                 110

Leu Thr Ala Lys Pro Glu Val Ile Asp Gly Glu Pro Ala Thr Leu Val
        115                 120                 125

Ser Glu Ser Phe Val Val Asp Val Pro Glu Gly Asn Thr Ala Asp Glu
    130                 135                 140

Thr Arg His Phe Val Glu Phe Leu Ile Arg Cys Asn Leu Arg Ser Leu
145                 150                 155                 160

Ala Met Val Ser Gln Arg Leu Leu Leu Ala Gln Gly Asp Leu Ala Glu
                165                 170                 175

Pro Pro Ala Gln
            180

<210> SEQ ID NO 77
<211> LENGTH: 176
<212> TYPE: PRT
<213> ORGANISM: Vitis vinifera
<220> FEATURE:
<223> OTHER INFORMATION: wine grape cultivar Pinot Noir hypothetical
      protein, clone ENTAV 115, locus tag VITISV_029498, GenBank
      Accession No. CAN64668.1

<400> SEQUENCE: 77

Met Asn Gly Asn Gly Leu Ser Ser Met Glu Ser Glu Tyr Ile Arg Arg
1               5                   10                  15

His His Arg His Glu Pro Ala Glu Asn Gln Cys Ser Ser Ala Leu Val
            20                  25                  30

Lys His Ile Lys Ala Pro Val Pro Leu Val Trp Ser Leu Val Arg Arg
        35                  40                  45

Phe Asp Gln Pro Gln Lys Tyr Lys Pro Phe Ile Ser Arg Cys Val Val
    50                  55                  60
```

```
Gln Gly Asn Leu Glu Ile Gly Ser Leu Arg Glu Val Asp Val Lys Ser
 65                  70                  75                  80

Gly Leu Pro Ala Thr Thr Ser Thr Glu Arg Leu Glu Leu Leu Asp Asp
                 85                  90                  95

Asp Glu His Ile Leu Ser Met Arg Ile Ile Gly Gly Asp His Arg Leu
            100                 105                 110

Arg Asn Tyr Ser Ser Ile Ile Ser Leu His Pro Glu Ile Ile Asp Gly
        115                 120                 125

Arg Pro Gly Thr Met Val Ile Glu Ser Tyr Val Val Asp Val Pro Glu
    130                 135                 140

Gly Asn Thr Lys Asp Glu Thr Cys Tyr Phe Ser Leu Ala Asp Val Ser
145                 150                 155                 160

Glu Arg Leu Ala Val Ala Gly Thr Val Thr Glu Pro Ile Asp Arg Met
                165                 170                 175

<210> SEQ ID NO 78
<211> LENGTH: 180
<212> TYPE: PRT
<213> ORGANISM: Oryza sativa
<220> FEATURE:
<223> OTHER INFORMATION: rice Indica Group, cultivar 93-11, hypothetical
      protein, locus tag OsI_06615, GenBank Accession No. EEC72859.1

<400> SEQUENCE: 78

Met Val Glu Met Asp Ala Gly Gly Arg Pro Glu Pro Ser Pro Pro Ser
  1               5                  10                  15

Gly Gln Cys Ser Ser Ala Val Thr Met Arg Ile Asn Ala Pro Val His
                 20                  25                  30

Leu Val Trp Ser Ile Val Arg Arg Phe Glu Glu Pro His Ile Phe Gln
             35                  40                  45

Pro Phe Val Arg Gly Cys Thr Met Arg Gly Ser Thr Ser Leu Ala Val
         50                  55                  60

Gly Cys Val Arg Glu Val Asp Phe Lys Ser Gly Phe Ser Ala Lys Ser
 65                  70                  75                  80

Ser Val Glu Arg Leu Glu Ile Leu Asp Asp Lys Glu His Val Phe Gly
                 85                  90                  95

Val Arg Ile Ile Gly Gly Asp His Arg Leu Lys Asn Tyr Ser Ser Val
            100                 105                 110

Leu Thr Ala Lys Pro Glu Val Ile Asp Gly Pro Ala Thr Leu Val
        115                 120                 125

Ser Glu Ser Phe Val Ile Asp Val Pro Glu Gly Asn Thr Ala Asp Glu
    130                 135                 140

Thr Arg His Phe Val Glu Phe Leu Ile Arg Cys Asn Leu Arg Ser Leu
145                 150                 155                 160

Ala Met Val Ser Gln Arg Leu Leu Leu Ala Gln Gly Asp Leu Ala Glu
                165                 170                 175

Pro Pro Ala Gln
            180

<210> SEQ ID NO 79
<211> LENGTH: 215
<212> TYPE: PRT
<213> ORGANISM: Oryza sativa
<220> FEATURE:
<223> OTHER INFORMATION: rice Japonica Group, cultivar Nipponbare,
      hypothetical protein, locus tag OsJ_10498, GenBank Accession No.
      EAZ26598.1

<400> SEQUENCE: 79
```

```
Met Pro Cys Ile Pro Ala Ser Ser Pro Gly Ile Pro His Gln His Gln
1               5                   10                  15

His Gln His His Arg Ala Leu Ala Gly Val Gly Met Ala Val Gly Cys
                20                  25                  30

Ala Ala Glu Ala Ala Val Ala Ala Gly Val Ala Gly Thr Arg Cys
            35                  40                  45

Gly Ala His Asp Gly Glu Val Pro Met Glu Val Ala Arg His His Glu
        50                  55                  60

His Ala Glu Pro Gly Ser Gly Arg Cys Cys Ser Ala Val Val Gln His
65                  70                  75                  80

Val Ala Ala Pro Ala Ala Ala Val Trp Ser Val Val Arg Arg Phe Asp
                85                  90                  95

Gln Pro Gln Ala Tyr Lys Arg Phe Val Arg Ser Cys Ala Leu Leu Ala
                100                 105                 110

Gly Asp Gly Gly Leu Gly Lys Val Arg Glu Arg Leu Glu Ile Leu Asp
            115                 120                 125

Asp Glu Ser His Val Leu Ser Phe Arg Val Val Gly Gly Glu His Arg
            130                 135                 140

Leu Lys Asn Tyr Leu Ser Val Thr Thr Val His Pro Ser Pro Ser Ala
145                 150                 155                 160

Pro Thr Ala Ala Thr Val Val Glu Ser Tyr Val Asp Val Pro
                165                 170                 175

Pro Gly Asn Thr Pro Glu Asp Thr Arg Val Phe Val Asp Thr Ile Val
                180                 185                 190

Lys Cys Asn Leu Gln Ser Leu Ala Lys Thr Ala Glu Lys Leu Ala Ala
                195                 200                 205

Gly Ala Arg Ala Ala Gly Ser
                210                 215

<210> SEQ ID NO 80
<211> LENGTH: 186
<212> TYPE: PRT
<213> ORGANISM: Rheum australe
<220> FEATURE:
<223> OTHER INFORMATION: Himalayan rhubarb pathogen-induced protein-like
      protein, GenBank Accession No. ACH63237.1

<400> SEQUENCE: 80

Met Asn Gly Asp Gly Tyr Gly Gly Ser Glu Glu Phe Val Lys Arg
1               5                   10                  15

Tyr His Glu His Val Leu Ala Asp His Gln Cys Ser Ser Val Leu Val
                20                  25                  30

Glu His Ile Asn Ala Pro Leu His Leu Val Trp Ser Leu Val Arg Ser
            35                  40                  45

Phe Asp Gln Pro Gln Lys Tyr Lys Pro Phe Val Ser Arg Cys Val Val
        50                  55                  60

Gln Gly Gly Asp Leu Glu Ile Gly Ser Val Arg Glu Val Asp Val Lys
65                  70                  75                  80

Ser Gly Leu Pro Ala Thr Thr Ser Met Glu Glu Leu Glu Leu Leu Asp
                85                  90                  95

Asp Lys Glu His Val Leu Arg Val Lys Phe Val Gly Gly Asp His Arg
                100                 105                 110

Leu Lys Asn Tyr Ser Ser Ile Val Ser Leu His Pro Glu Ile Ile Gly
            115                 120                 125

Gly Arg Ser Gly Thr Met Val Ile Glu Ser Phe Ile Val Asp Ile Ala
```

130                 135                 140

Asp Gly Asn Thr Lys Glu Glu Thr Cys Tyr Phe Ile Glu Ser Leu Ile
145                 150                 155                 160

Asn Cys Asn Leu Lys Ser Leu Ser Cys Val Ser Glu Arg Leu Ala Val
                    165                 170                 175

Glu Asp Ile Ala Glu Arg Ile Ala Gln Met
                    180                 185

<210> SEQ ID NO 81
<211> LENGTH: 254
<212> TYPE: PRT
<213> ORGANISM: Oryza sativa
<220> FEATURE:
<223> OTHER INFORMATION: rice Japonica Group, cultivar Nipponbare,
      hypothetical protein, locus tag OsJ_016770, GenBank Accession No.
      EAZ33287.1

<400> SEQUENCE: 81

Met Val Gly Leu Val Gly Gly Gly Trp Arg Val Gly Asp Asp Ala
1               5                   10                  15

Ala Gly Gly Gly Gly Gly Ala Val Ala Ala Gly Ala Ala Ala Ala
                20                  25                  30

Ala Glu Ala Glu His Met Arg Arg Leu His Ser Gln Gly Pro Arg Arg
                35                  40                  45

Ala Pro Val Gln Leu Arg Ala Arg Gln Ala His Gln Gly Ser Cys Ser
50                  55                  60

Pro Pro Arg Ile Glu Cys Ala Asn Phe Ala Val Phe Leu Ala Ala Arg
65                  70                  75                  80

Asp Pro Lys Ile Val Trp Ser Leu Val Arg Ser Phe Asp Gln Pro Gln
                85                  90                  95

Arg Tyr Lys Pro Phe Val Ser Arg Cys Val Val Arg Gly Gly Asp Leu
                100                 105                 110

Glu Ile Gly Ser Val Arg Glu Val Asn Val Lys Thr Gly Leu Pro Ala
                115                 120                 125

Thr Thr Ser Thr Glu Arg Leu Glu Leu Leu Asp Asp Asp Glu His Ile
130                 135                 140

Leu Ser Val Lys Phe Val Gly Gly Asp His Arg Leu Arg Asn Tyr Ser
145                 150                 155                 160

Ser Ile Val Thr Val His Pro Glu Ser Ile Asp Gly Arg Pro Gly Thr
                165                 170                 175

Leu Val Ile Glu Ser Phe Val Val Asp Val Pro Asp Gly Asn Thr Lys
                180                 185                 190

Asp Glu Thr Cys Tyr Phe Val Glu Ala Val Ile Lys Cys Asn Leu Thr
                195                 200                 205

Ser Leu Ala Glu Met Val Arg Met Ile Ser Leu Val Leu Pro Phe Met
210                 215                 220

Leu Val Asp Arg Met Ser Gly Ile Thr Cys Glu Ser His Leu Glu Thr
225                 230                 235                 240

Thr Leu Val Arg Cys Gly Glu Tyr Ala Val Leu Ala His Val
                245                 250

<210> SEQ ID NO 82
<211> LENGTH: 186
<212> TYPE: PRT
<213> ORGANISM: Oryza sativa
<220> FEATURE:
<223> OTHER INFORMATION: rice Japonica Group, cultivar Nipponbare,
      hypothetical protein, locus tag OsJ_005784, GenBank Accession No.

EAZ22301.1

<400> SEQUENCE: 82

| Met | Glu | Pro | His | Met | Glu | Arg | Ala | Leu | Arg | Glu | Ala | Val | Ala | Ser | Glu |
|---|---|---|---|---|---|---|---|---|---|---|---|---|---|---|---|
| 1 | | | | 5 | | | | | 10 | | | | | 15 | |

Ala Glu Arg Arg Glu Leu Glu Gly Val Val Arg Ala His His Thr Gly
            20                  25                  30

Trp Asn Ala Pro Leu Ala Ala Val Trp Pro His Arg Ala Arg Val Arg
                35                  40                  45

Pro Thr Arg Ser Gly Thr Ser Thr Ser Ser Ser Arg Ala Ser Ser Pro
            50                  55                  60

Pro Gly Asp Gly Ala Thr Val Gly Ser Val Arg Glu Val Ala Val Val
65                  70                  75                  80

Ser Gly Leu Pro Ala Ser Thr Ser Thr Glu Arg Leu Glu Ile Leu Asp
                85                  90                  95

Asp Asp Arg His Val Leu Ser Phe Arg Val Val Gly Gly Asp His Arg
            100                 105                 110

Leu Arg Asn Tyr Arg Ser Val Thr Ser Val Thr Glu Phe Ser Ser Pro
            115                 120                 125

Ser Ser Pro Pro Arg Pro Tyr Cys Val Val Glu Ser Tyr Val Val
            130                 135                 140

Asp Val Pro Glu Gly Asn Thr Glu Asp Thr Arg Met Phe Thr Asp
145                 150                 155                 160

Thr Val Val Lys Leu Asn Leu Gln Lys Leu Ala Val Ala Thr Ser
                165                 170                 175

Ser Ser Pro Pro Ala Ala Gly Asn His His
            180                 185

<210> SEQ ID NO 83
<211> LENGTH: 150
<212> TYPE: PRT
<213> ORGANISM: Oryza sativa
<220> FEATURE:
<223> OTHER INFORMATION: rice Japonica Group, cultivar Nipponbare,
      hypothetical protein, locus tag OsJ_005938, GenBank Accession No.
      EAZ22455.1

<400> SEQUENCE: 83

| Met | Glu | Val | Val | Trp | Ser | Ile | Val | Arg | Arg | Phe | Glu | Glu | Pro | His | Ile |
|---|---|---|---|---|---|---|---|---|---|---|---|---|---|---|---|
| 1 | | | | 5 | | | | | 10 | | | | | 15 | |

Phe Gln Pro Phe Val Arg Gly Cys Thr Met Arg Gly Ser Thr Ser Leu
            20                  25                  30

Ala Val Gly Cys Val Arg Glu Val Asp Phe Lys Ser Gly Phe Pro Ala
                35                  40                  45

Lys Ser Ser Val Glu Arg Leu Glu Ile Leu Asp Asp Lys Glu His Val
50                  55                  60

Phe Gly Val Arg Ile Ile Gly Gly Asp His Arg Leu Lys Asn Tyr Ser
65                  70                  75                  80

Ser Val Leu Thr Ala Lys Pro Glu Val Ile Asp Gly Glu Pro Ala Thr
                85                  90                  95

Leu Val Ser Glu Ser Phe Val Val Asp Val Pro Glu Gly Asn Thr Ala
            100                 105                 110

Asp Glu Thr Arg His Phe Val Glu Phe Leu Ile Arg Cys Asn Leu Arg
            115                 120                 125

Ser Leu Ala Met Val Ser Gln Arg Leu Leu Ala Gln Gly Asp Leu
            130                 135                 140

Ala Glu Pro Pro Gly Gln
145                 150

<210> SEQ ID NO 84
<211> LENGTH: 206
<212> TYPE: PRT
<213> ORGANISM: Oryza sativa
<220> FEATURE:
<223> OTHER INFORMATION: rice Japonica Group, cultivar Nipponbare,
      hypothetical protein, locus tag OsJ_018129, GenBank Accession No.
      EAZ34646.1

<400> SEQUENCE: 84

Met Pro Tyr Thr Ala Pro Arg Pro Ser Pro Pro Gln His Ser Arg Ile
1               5                   10                  15

Gly Gly Cys Gly Gly Gly Gly Val Leu Lys Ala Ala Gly Ala Ala Gly
            20                  25                  30

His Ala Ala Ser Cys Val Ala Val Pro Ala Glu Val Ala Arg His His
        35                  40                  45

Glu His Ala Ala Gly Val Gly Gln Cys Cys Ser Ala Val Val Gln Ala
    50                  55                  60

Ile Ala Ala Pro Val Asp Ala Val Trp Arg Thr Ser Thr Ser Ser Gly
65                  70                  75                  80

Ala Ala Ala Ser Trp Thr Ala Thr Ala Thr Ala Gly Pro Leu Pro Val
                85                  90                  95

Gly Ser Val Arg Glu Phe Arg Val Leu Ser Gly Leu Pro Gly Thr Ser
            100                 105                 110

Ser Arg Glu Arg Leu Glu Ile Leu Asp Asp Glu Arg Arg Val Leu Ser
        115                 120                 125

Phe Arg Val Val Gly Gly Glu His Arg Leu Ser Asn Tyr Arg Ser Val
    130                 135                 140

Thr Thr Val His Glu Thr Ala Ala Gly Ala Ala Ala Val Val Val
145                 150                 155                 160

Glu Ser Tyr Val Val Asp Val Pro His Gly Asn Thr Ala Asp Glu Thr
                165                 170                 175

Arg Met Phe Val Asp Thr Ile Val Arg Cys Asn Leu Gln Ser Leu Ala
            180                 185                 190

Arg Thr Ala Glu Gln Leu Ala Leu Ala Ala Pro Arg Ala Ala
        195                 200                 205

<210> SEQ ID NO 85
<211> LENGTH: 396
<212> TYPE: PRT
<213> ORGANISM: Vitis vinifera
<220> FEATURE:
<223> OTHER INFORMATION: wine grape cultivar Pinot Noir hypothetical
      protein, clone ENTAV 115, locus tag VITISV_001710, GenBank
      Accession No. CAN76441.1
<220> FEATURE:
<221> NAME/KEY: VARIANT
<222> LOCATION: (1)...(396)
<223> OTHER INFORMATION: Xaa = any amino acid

<400> SEQUENCE: 85

Met Pro Ile Ser Ser Leu Pro Phe Ser Leu Tyr Thr Val Thr Pro Asn
1               5                   10                  15

Pro Leu Lys Leu Ile Thr Thr His Ala His Ala Phe Thr Pro His Thr
            20                  25                  30

His Ile Phe Thr Leu Lys Phe Met Ser His Thr Tyr Cys Pro His Ile
        35                  40                  45

His His Ile Thr Ser Ile His Tyr Thr His Leu Leu Xaa Pro Ile Pro
 50                      55                      60

His Met Pro Leu Gln Pro Pro Leu Pro Pro His Pro Ile Leu Pro Ser
 65                  70                  75                  80

Met Pro Ala Phe Gln His Leu Tyr Ser Thr Asn Gln His Leu Gln Val
                 85                  90                  95

Ala Leu Phe Ser Ala Arg Gly Pro Asn Ile Arg Asp Phe Asn Phe Gln
            100                 105                 110

Asp Ala Asp Leu Leu Lys Leu Asp Ile Leu Ala Pro Gly Ser Leu Ile
        115                 120                 125

Trp Ala Ala Trp Ser Pro Asn Gly Thr Asp Glu Ala Asn Tyr Val Gly
130                 135                 140

Glu Gly Ser Pro Thr Val Ala Met Ile Ala Lys Arg Gly Pro Arg His
145                 150                 155                 160

Gly Lys Tyr Met Ala Phe Cys Xaa Met Tyr Arg Asp Asn Val Ala Pro
                165                 170                 175

Lys Gly Val Asn Xaa Ala Val Ala Thr Val Lys Thr Lys Arg Thr Ile
            180                 185                 190

Gln Leu Lys Thr Ser Leu Glu Ile Ala Cys His Tyr Ala Gly Ile Asn
        195                 200                 205

Ile Ser Gly Ile Asn Gly Glu Val Met Pro Gly Gln Trp Glu Tyr Gln
210                 215                 220

Val Gly Pro Gly Gln Cys Ser Ser Leu Leu Ala Gln Arg Val His Val
225                 230                 235                 240

Pro Leu Ser Ala Val Gly Ser Val Val His Arg Phe Asp Lys Pro Gln
                245                 250                 255

Arg Tyr Gln His Val Ile Lys Ser Cys Arg Ile Glu Asp Gly Phe Glu
            260                 265                 270

Met Arg Met Gly Xaa Leu Arg Asp Val Asn Ile Ile Ser Gly Leu Pro
        275                 280                 285

Thr Ala Thr Asn Thr Gly Arg Leu Asp Met Gln Asp Asp Glu Arg His
290                 295                 300

Val Thr Arg Cys Pro His Gln Arg Gln Ser Glu Ser Lys Tyr Thr Glu
305                 310                 315                 320

Asn Asn Asn Ser Asp Ala Ser Ser Ile Lys Ser Pro Ile Asn Gly Pro
                325                 330                 335

Ser Glu His Leu Lys Thr Ala Ala Ser Pro Lys Thr Glu Ser Ile Ile
            340                 345                 350

Val Ile Asp Thr Ser Lys Phe Leu Asn Glu Glu Asp Phe Glu Gly Lys
        355                 360                 365

Asp Glu Thr Ser Ser Ser Asn Gln Val Gln Ile Glu Asp Glu Asn Trp
370                 375                 380

Glu Thr Arg Phe Pro Asn Thr Asp Ala Gly Ile Trp
385                 390                 395

<210> SEQ ID NO 86
<211> LENGTH: 443
<212> TYPE: PRT
<213> ORGANISM: Vitis vinifera
<220> FEATURE:
<223> OTHER INFORMATION: wine grape cultivar Pinot Noir hypothetical
      protein, clone ENTAV 115, locus tag VITISV_014403, GenBank
      Accession No. CAN9881.1
<220> FEATURE:
<221> NAME/KEY: VARIANT
<222> LOCATION: (1)...(443)
<223> OTHER INFORMATION: Xaa = any amino acid

<400> SEQUENCE: 86

```
Met Pro Ser Ala Xaa Lys Ser Ser Thr Val Pro Leu Ser Leu Xaa Gln
1               5                   10                  15

Phe Lys Leu Gly Leu Arg His Gly His Arg Val Ile Pro Trp Gly Asp
            20                  25                  30

Leu Asp Ser Leu Ala Met Leu Gln Arg Gln Leu Asp Val Asp Ile Leu
        35                  40                  45

Val Thr Gly His Thr His Arg Phe Thr Ala Tyr Lys His Glu Gly Gly
    50                  55                  60

Val Val Ile Asn Pro Gly Ser Ala Thr Gly Ala Phe Gly Ser Ile Thr
65                  70                  75                  80

Tyr Asp Val Asn Pro Ser Phe Val Leu Met Asp Ile Asp Gly Leu Arg
                85                  90                  95

Val Val Val Cys Val Tyr Glu Leu Ile Asp Glu Thr Ala Asn Ile Ile
            100                 105                 110

Lys Glu Leu His Ala Arg Lys Ile Ser Phe Gly Thr Lys Ser Met Ile
        115                 120                 125

Xaa Cys Leu Leu Leu Lys Arg Arg Ser Thr Pro Lys Phe Arg Arg Lys
130                 135                 140

Lys Leu Phe Leu Phe Gln Cys Arg Val Gln Met Thr Leu Thr Leu Thr
145                 150                 155                 160

Asn Leu Ala Val Ser Gly Ile Ala Gln Thr Leu Gln Val Asp Gln Trp
                165                 170                 175

Thr Val Cys Ala Leu Ile Phe Met Thr Arg Arg Asp Ile His Leu Asp
            180                 185                 190

Lys Ala Arg Phe Leu Asp Phe Lys Asp Met Gly Lys Leu Leu Ala Asp
        195                 200                 205

Ala Ser Gly Leu Arg Lys Ala Leu Ser Gly Gly Xaa Val Thr Ala Gly
    210                 215                 220

Met Ala Ile Phe Asp Thr Met Arg His Ile Arg Pro Asp Val Pro Thr
225                 230                 235                 240

Val Cys Val Gly Leu Ala Ala Val Ala Met Ile Ala Lys Arg Gly Pro
                245                 250                 255

Arg His Gly Lys Tyr Met Ala Phe Cys Pro Met Tyr Arg Asp Asn Val
            260                 265                 270

Ala Pro Lys Gly Val Asn Val Ala Val Val Thr Val Lys Thr Lys Arg
        275                 280                 285

Thr Ile Gln Leu Lys Thr Ser Leu Glu Ile Ala Cys His Tyr Ala Gly
    290                 295                 300

Ile Asn Ile Ser Gly Ile Asn Gly Glu Val Met Pro Gly Gln Trp Glu
305                 310                 315                 320

Tyr Gln Val Gly Pro Gly Gln Cys Ser Ser Leu Leu Ala Gln Arg Val
                325                 330                 335

His Val Pro Leu Ser Ala Val Gly Ser Val Val His Arg Phe Asp Lys
            340                 345                 350

Pro Gln Arg Tyr Gln His Val Ile Lys Ser Cys Arg Ile Glu Asp Gly
        355                 360                 365

Phe Glu Met Arg Met Gly Arg Leu Arg Asp Val Asn Ile Ile Ser Gly
    370                 375                 380

Leu Pro Thr Ala Thr Asn Thr Gly Arg Leu Asp Met Gln Asp Asp Glu
385                 390                 395                 400

Xaa His Val Thr Arg Cys Pro His Gln Arg Gln Ser Glu Ser Lys Tyr
```

```
                        405                 410                 415

Thr Glu Asn Asn Asn Ser Asp Ala Ser Ser Val Lys Ser Pro Ile Asn
                420                 425                 430

Gly Pro Ser Glu His Leu Lys Thr Ala Ala Xaa
            435                 440

<210> SEQ ID NO 87
<211> LENGTH: 95
<212> TYPE: PRT
<213> ORGANISM: Oryza sativa
<220> FEATURE:
<223> OTHER INFORMATION: rice Indica Group, cultivar Pokkali, capip1
      protein, clone OSR-385-428-D5, GenBank Accession No. ABR25904.1

<400> SEQUENCE: 87

Glu Ile Gly Ser Val Arg Glu Val Asn Val Lys Thr Gly Leu Pro Ala
1               5                   10                  15

Thr Thr Ser Thr Glu Arg Leu Glu Leu Leu Asp Asp Asp Glu His Ile
            20                  25                  30

Leu Ser Val Lys Phe Val Gly Gly Asp His Arg Leu Arg Asn Tyr Ser
        35                  40                  45

Ser Ile Val Thr Val His Pro Glu Ser Ile Asp Gly Arg Pro Gly Thr
    50                  55                  60

Leu Val Ile Glu Ser Phe Val Val Asp Val Pro Asp Gly Asn Thr Lys
65                  70                  75                  80

Asp Glu Thr Cys Tyr Phe Val Glu Ala Val Ile Lys Cys Asn Leu
                85                  90                  95

<210> SEQ ID NO 88
<211> LENGTH: 191
<212> TYPE: PRT
<213> ORGANISM: Zea mays
<220> FEATURE:
<223> OTHER INFORMATION: maize strain B73 unknown protein, clone
      ZM_BFc0034007, GenBank Accession No. ACF84624.1

<400> SEQUENCE: 88

Met Val Val Glu Met Asp Gly Val Gly Val Ala Ala Ala Gly Gly
1               5                   10                  15

Gly Gly Ala Gln Thr Pro Ala Pro Pro Pro Arg Arg Trp Arg Leu
            20                  25                  30

Ala Asp Glu Arg Cys Asp Leu Arg Ala Met Glu Thr Asp Tyr Val Arg
            35                  40                  45

Arg Phe His Arg His Glu Pro Arg Asp His Gln Cys Ser Ser Ala Val
    50                  55                  60

Ala Lys His Ile Lys Ala Pro Val His Leu Val Trp Ser Leu Val Arg
65                  70                  75                  80

Arg Phe Asp Gln Pro Gln Leu Phe Lys Pro Phe Val Ser Arg Cys Glu
                85                  90                  95

Met Lys Gly Asn Ile Glu Ile Gly Ser Val Arg Glu Val Asn Val Lys
            100                 105                 110

Ser Gly Leu Pro Ala Thr Arg Ser Thr Glu Arg Leu Glu Leu Leu Asp
        115                 120                 125

Asp Asp Glu Arg Ile Leu Ser Val Arg Phe Val Gly Gly Asp His Arg
    130                 135                 140

Leu Gln Val Cys Ser Val Leu His Leu Ser Ile Phe Cys Ala Ala His
145                 150                 155                 160

Ala Arg Tyr Phe Ala His His Leu Lys Cys Val Leu Glu Phe Leu Cys
```

165                 170                 175

Gln Met His Leu Asp Val Leu Pro Cys Asp Asp Ala Ile Leu Glu
        180                 185                 190

<210> SEQ ID NO 89
<211> LENGTH: 239
<212> TYPE: PRT
<213> ORGANISM: Oryza sativa
<220> FEATURE:
<223> OTHER INFORMATION: rice Japonica Group, cultivar Nipponbare,
      hypothetical protein, locus tag OsJ_020681, GenBank Accession No.
      EAZ37198.1

<400> SEQUENCE: 89

Met Asn Gly Cys Thr Gly Gly Ala Gly Gly Val Ala Ala Gly Arg Leu
1               5                   10                  15

Pro Ala Val Ser Leu Gln Gln Ala Gln Trp Lys Leu Val Asp Glu Arg
            20                  25                  30

Cys Glu Leu Arg Glu Glu Glu Met Glu Tyr Val Arg Arg Phe His Arg
        35                  40                  45

His Glu Ile Gly Ser Asn Gln Cys Asn Ser Phe Ile Ala Lys His Val
    50                  55                  60

Arg Ala Pro Leu Gln Asn Val Trp Ser Leu Val Arg Arg Phe Asp Gln
65                  70                  75                  80

Pro Gln Ile Tyr Lys Pro Phe Val Arg Lys Cys Val Met Arg Gly Asn
                85                  90                  95

Val Glu Thr Gly Ser Val Arg Glu Ile Ile Val Gln Ser Gly Leu Pro
            100                 105                 110

Ala Thr Arg Ser Ile Glu Arg Leu Glu Phe Leu Asp Asp Asn Glu Tyr
        115                 120                 125

Ile Leu Arg Val Lys Phe Ile Gly Gly Asp His Met Leu Lys Lys Arg
    130                 135                 140

Ile Pro Lys Lys Thr Tyr Ala Ile Ser Ser Arg Thr Cys Ser Asp Ser
145                 150                 155                 160

Ala Ile Ile Ala Val Gly Gln Ser Asn Cys Ala Pro Glu Ile Thr Ala
                165                 170                 175

Met Asn Gly Gly Val Ser Ile Gln Pro Trp Leu Ile Leu Leu Ala Phe
            180                 185                 190

Phe Ser Ser Pro Ser Asn Gln Thr Asn Pro Asp Ser Leu Arg Asp Met
        195                 200                 205

His Pro Gly Ser Trp Phe Gln Ile Leu Leu Val Leu Ala Met Phe Thr
    210                 215                 220

Cys Ser Lys Gly Ser Val Leu Pro Pro Ser Glu Lys Val Asn Val
225                 230                 235

<210> SEQ ID NO 90
<211> LENGTH: 188
<212> TYPE: PRT
<213> ORGANISM: Zea mays
<220> FEATURE:
<223> OTHER INFORMATION: maize GRMZM2G154987_P01 protein

<400> SEQUENCE: 90

Met Glu Pro His Met Glu Ser Ala Leu Arg Gln Gly Leu Ser Glu Ala
1               5                   10                  15

Glu Gln Arg Glu Leu Glu Gly Val Val Arg Ala His His Thr Phe Pro
            20                  25                  30

Gly Arg Ala Pro Gly Thr Cys Thr Ser Leu Val Thr Gln Arg Val Asp

```
            35                  40                  45
Ala Pro Leu Ala Ala Val Trp Pro Ile Val Arg Gly Phe Gly Ser Pro
         50                  55                  60

Gln Arg Tyr Lys His Phe Ile Lys Ser Cys Asp Leu Lys Ala Gly Asp
 65                  70                  75                  80

Gly Ala Thr Val Gly Ser Val Arg Glu Val Thr Val Val Ser Gly Leu
                 85                  90                  95

Pro Ala Ser Thr Ser Thr Glu Arg Leu Glu Ile Leu Asp Asp His Arg
            100                 105                 110

His Ile Leu Ser Phe Arg Val Val Gly Gly Asp His Arg Leu Arg Asn
        115                 120                 125

Tyr Arg Ser Val Thr Ser Val Thr Glu Phe Gln Pro Gly Pro Tyr Cys
    130                 135                 140

Val Val Leu Glu Ser Tyr Val Val Asp Val Pro Asp Gly Asn Thr Glu
145                 150                 155                 160

Glu Asp Thr Arg Met Phe Thr Asp Thr Val Val Lys Leu Asn Leu Gln
                165                 170                 175

Lys Leu Ala Ala Ile Ala Thr Ser Ser Ser Ala Asn
            180                 185

<210> SEQ ID NO 91
<211> LENGTH: 205
<212> TYPE: PRT
<213> ORGANISM: Zea mays
<220> FEATURE:
<223> OTHER INFORMATION: maize GRMZM2G134731_P01 protein

<400> SEQUENCE: 91

Met Asp Gln Gln Gly Ala Gly Gly Asp Val Glu Val Pro Ala Gly Leu
 1               5                  10                  15

Gly Leu Thr Ala Ala Glu Tyr Glu Gln Leu Arg Pro Thr Val Asp Ala
                 20                  25                  30

His His Arg Tyr Ala Val Gly Glu Gly Gln Cys Ser Ser Leu Leu Ala
            35                  40                  45

Gln Arg Ile His Ala Pro Pro Ala Ala Val Trp Ala Ile Val Arg Arg
 50                  55                  60

Phe Asp Cys Pro Gln Val Tyr Lys His Phe Ile Arg Ser Cys Ala Val
 65                  70                  75                  80

Arg Pro Asp Pro Asp Ala Gly Asp Ala Leu Arg Pro Gly Arg Leu Arg
                 85                  90                  95

Glu Val Cys Val Ile Ser Gly Leu Pro Ala Ser Thr Ser Thr Glu Arg
            100                 105                 110

Leu Asp His Leu Asp Asp Ala Ala Arg Val Phe Gly Phe Ser Ile Thr
        115                 120                 125

Gly Gly Glu His Arg Leu Arg Asn Tyr Arg Ser Val Thr Thr Val Ser
    130                 135                 140

Glu Leu Ala Gly Pro Gly Ile Cys Thr Val Val Leu Glu Ser Tyr Ala
145                 150                 155                 160

Val Asp Val Pro Asp Gly Asn Thr Glu Asp Thr Arg Leu Phe Ala
                165                 170                 175

Asp Thr Val Ile Arg Leu Asn Leu Gln Lys Leu Lys Ser Val Ala Glu
            180                 185                 190

Ala Ser Thr Ser Ser Ser Ala Pro Pro Pro Ser Glu
        195                 200                 205
```

-continued

```
<210> SEQ ID NO 92
<211> LENGTH: 220
<212> TYPE: PRT
<213> ORGANISM: Zea mays
<220> FEATURE:
<223> OTHER INFORMATION: maize GRMZM2G144224_P01 protein

<400> SEQUENCE: 92

Met Pro Cys Ile Gln Ala Ser Ser Pro Gly Gly Met Pro His Gln His
1               5                   10                  15

Gly Arg Gly Arg Val Leu Gly Gly Val Gly Cys Ala Ala Glu Val
            20                  25                  30

Ala Ala Ala Val Ala Ala Ser Ala Gly Gly Met Arg Cys Gly Ala His
        35                  40                  45

Asp Gly Glu Val Pro Ala Glu Ala Ala Arg His His Glu His Ala Ala
    50                  55                  60

Ala Gly Pro Gly Arg Cys Cys Ser Ala Val Val Gln His Val Ala Ala
65                  70                  75                  80

Pro Ala Ala Ala Val Trp Ser Val Val Arg Arg Phe Asp Gln Pro Gln
                85                  90                  95

Val Tyr Lys Arg Phe Val Arg Ser Cys Ala Leu Leu Ala Gly Asp Gly
            100                 105                 110

Gly Val Gly Thr Leu Arg Glu Val Arg Val Val Ser Gly Leu Pro Ala
        115                 120                 125

Ala Ser Ser Arg Glu Arg Leu Glu Val Leu Asp Asp Glu Ser His Val
    130                 135                 140

Leu Ser Phe Arg Val Val Gly Gly Glu His Arg Leu Arg Asn Tyr Leu
145                 150                 155                 160

Ser Val Thr Thr Val His Pro Ser Pro Ala Ala Pro Asp Ala Ala Thr
                165                 170                 175

Val Val Val Glu Ser Tyr Val Val Asp Val Pro Pro Gly Asn Thr Pro
            180                 185                 190

Glu Asp Thr Arg Val Phe Val Asp Thr Ile Val Lys Cys Asn Leu Gln
        195                 200                 205

Ser Leu Ala Thr Thr Ala Glu Lys Leu Ala Ala Val
    210                 215                 220

<210> SEQ ID NO 93
<211> LENGTH: 221
<212> TYPE: PRT
<213> ORGANISM: Glycine max
<220> FEATURE:
<223> OTHER INFORMATION: soybean Glyma01g02290.1 protein

<400> SEQUENCE: 93

Met Glu Lys Ala Glu Ser Ser Ala Ser Thr Ser Glu Pro Asp Ser Asp
1               5                   10                  15

Glu Asn His His Arg His Pro Thr Asn His His Ile Asn Pro Pro Ser
            20                  25                  30

Gly Leu Thr Pro Leu Glu Phe Ala Ser Leu Ile Pro Ser Val Ala Glu
        35                  40                  45

His His Ser Tyr Leu Val Gly Ser Gly Gln Cys Ser Ser Leu Leu Ala
    50                  55                  60

Gln Arg Val Gln Ala Pro Pro Asp Ala Val Trp Ser Val Val Arg Arg
65                  70                  75                  80

Phe Asp Lys Pro Gln Thr Tyr Lys His Phe Ile Lys Ser Cys Ala Val
                85                  90                  95
```

```
Lys Glu Pro Phe His Met Ala Val Gly Val Thr Arg Asp Val Asn Val
                100                 105                 110

Ile Ser Gly Leu Pro Ala Ala Thr Ser Thr Glu Arg Leu Asp Leu Leu
            115                 120                 125

Asp Asp Ile Arg Cys Val Thr Gly Phe Ser Ile Ile Gly Gly Glu His
        130                 135                 140

Arg Leu Arg Asn Tyr Arg Ser Val Thr Thr Val His Ser Phe Glu Asp
145                 150                 155                 160

Asp Ala Asp Asp Gly Lys Ile Tyr Thr Val Leu Glu Ser Tyr Val
                165                 170                 175

Val Asp Val Pro Asp Gly Asn Thr Glu Glu Asp Thr Arg Leu Phe Ala
            180                 185                 190

Asp Thr Val Val Lys Leu Asn Leu Gln Lys Leu Ala Ser Val Thr Glu
        195                 200                 205

Gly Thr Asn Arg Asp Gly Asp Gly Lys Ser His Ser Arg
    210                 215                 220

<210> SEQ ID NO 94
<211> LENGTH: 214
<212> TYPE: PRT
<213> ORGANISM: Glycine max
<220> FEATURE:
<223> OTHER INFORMATION: soybean Glyma01g12970.1 protein

<400> SEQUENCE: 94

Met Glu Lys Thr His Ser Ser Ala Glu Glu Gln Asp Pro Thr Arg
1               5                   10                  15

Arg His Leu Asp Pro Pro Gly Leu Thr Ala Glu Glu Phe Glu Asp
                20                  25                  30

Leu Lys Pro Ser Val Leu Glu His His Thr Tyr Ser Val Thr Pro Thr
            35                  40                  45

Arg Gln Ser Ser Ser Leu Leu Ala Gln Arg Ile His Ala Pro Pro His
        50                  55                  60

Ala Val Trp Ser Val Val Arg Cys Phe Asp Asn Pro Gln Ala Tyr Lys
65                  70                  75                  80

His Phe Ile Lys Ser Cys His Val Lys Glu Gly Phe Gln Leu Ala Val
                85                  90                  95

Gly Ser Thr Arg Asp Val His Val Ile Ser Gly Leu Pro Ala Ala Thr
                100                 105                 110

Ser Thr Glu Arg Leu Asp Leu Leu Asp Asp Arg His Val Ile Gly
            115                 120                 125

Phe Thr Ile Val Gly Gly Asp His Arg Leu Arg Asn Tyr Arg Ser Val
        130                 135                 140

Thr Ser Val His Gly Phe Glu Cys Asp Gly Lys Ile Trp Thr Val Val
145                 150                 155                 160

Leu Glu Ser Tyr Val Val Asp Val Pro Glu Gly Asn Thr Glu Asp
                165                 170                 175

Thr Arg Leu Phe Ala Asp Thr Val Val Lys Leu Asn Leu Gln Lys Leu
            180                 185                 190

Ala Ser Val Ser Glu Gly Met Cys Gly Asp Gly Asp Gly Asp Gly Asp
        195                 200                 205

Gly Lys Gly Asn Lys Ser
    210

<210> SEQ ID NO 95
<211> LENGTH: 216
```

```
<212> TYPE: PRT
<213> ORGANISM: Glycine max
<220> FEATURE:
<223> OTHER INFORMATION: soybean Glyma01g31320.1 protein

<400> SEQUENCE: 95

Met Leu Gln Asn Ser Ser Met Ser Ser Leu Leu Leu His Arg Ile Asn
1               5                   10                  15

Gly Gly Gly Gly Ala Thr Thr Ala Thr Asn Cys His Asp Thr Val Phe
            20                  25                  30

Met Thr Val Pro Asp Gly Val Ala Arg Tyr His Thr His Ala Val Ala
        35                  40                  45

Pro Asn Gln Cys Cys Ser Ser Val Ala Gln Glu Ile Gly Ala Ser Val
    50                  55                  60

Ala Thr Val Trp Ser Val Leu Arg Arg Phe Asp Asn Pro Gln Ala Tyr
65                  70                  75                  80

Lys His Phe Val Lys Ser Cys His Val Ile Gly Gly Asp Gly Asp Val
                85                  90                  95

Gly Thr Leu Arg Glu Val His Val Ile Ser Gly Leu Pro Ala Ala Arg
            100                 105                 110

Ser Thr Glu Arg Leu Glu Ile Leu Asp Asp Arg His Val Ile Ser
        115                 120                 125

Phe Ser Val Val Gly Gly Asp His Arg Leu Ala Asn Tyr Arg Ser Val
130                 135                 140

Thr Thr Leu His Pro Thr Ala Ser Ser Ala Ser Gly Gly Cys Ser Gly
145                 150                 155                 160

Thr Val Val Val Glu Ser Tyr Val Val Asp Val Pro Pro Gly Asn Thr
                165                 170                 175

Arg Glu Asp Thr Arg Val Phe Val Asp Thr Ile Val Lys Cys Asn Leu
            180                 185                 190

Gln Ser Leu Ala Gln Thr Ala Glu Asn Leu Thr Leu Arg Lys Asn Asn
        195                 200                 205

Asn Asn Asp Tyr Lys Cys Cys Ser
    210                 215

<210> SEQ ID NO 96
<211> LENGTH: 208
<212> TYPE: PRT
<213> ORGANISM: Glycine max
<220> FEATURE:
<223> OTHER INFORMATION: soybean Glyma02g42990.1 protein

<400> SEQUENCE: 96

Met Thr Ser Leu Gln Phe His Arg Phe Asn Pro Ala Thr Asp Thr Ser
1               5                   10                  15

Thr Ala Ile Ala Asn Gly Val Asn Cys Pro Lys Pro Pro Ser Thr Leu
            20                  25                  30

Arg Leu Leu Ala Lys Val Ser Leu Ser Val Pro Glu Thr Val Ala Arg
        35                  40                  45

His His Ala His Pro Val Gly Pro Asn Gln Cys Cys Ser Val Val Ile
    50                  55                  60

Gln Ala Ile Asp Ala Pro Val Ser Ala Val Trp Pro Val Arg Arg
65                  70                  75                  80

Phe Asp Asn Pro Gln Ala Tyr Lys His Phe Val Lys Ser Cys His Val
                85                  90                  95

Val Ala Ala Ala Gly Gly Glu Asp Gly Ile Arg Val Gly Ala Leu
            100                 105                 110
```

```
Arg Glu Val Arg Val Val Ser Gly Leu Pro Ala Val Ser Ser Thr Glu
            115                 120                 125

Arg Leu Glu Ile Leu Asp Asp Glu Arg His Val Met Ser Phe Ser Val
        130                 135                 140

Val Gly Gly Asp His Arg Leu Arg Asn Tyr Arg Ser Val Thr Thr Leu
145                 150                 155                 160

His Gly Asp Gly Asn Gly Gly Thr Val Ile Glu Ser Tyr Val Val
                165                 170                 175

Asp Val Pro Pro Gly Asn Thr Lys Glu Glu Thr Cys Val Phe Val Asp
                180                 185                 190

Thr Ile Val Arg Cys Asn Leu Gln Ser Leu Ala Gln Ile Ala Glu Thr
            195                 200                 205
```

<210> SEQ ID NO 97
<211> LENGTH: 176
<212> TYPE: PRT
<213> ORGANISM: Glycine max
<220> FEATURE:
<223> OTHER INFORMATION: soybean Glyma04g05380.1 protein

<400> SEQUENCE: 97

```
Ala Tyr Pro Val Leu Gly Leu Thr Pro Glu Glu Phe Ser Glu Leu Glu
1               5                   10                  15

Ser Ile Ile Asn Thr His His Lys Phe Glu Pro Ser Pro Glu Ile Cys
            20                  25                  30

Ser Ser Ile Ile Ala Gln Arg Ile Asp Ala Pro Ala His Thr Val Trp
        35                  40                  45

Pro Leu Val Arg Ser Phe Glu Asn Pro Gln Lys Tyr Lys His Phe Val
    50                  55                  60

Lys Ser Cys Asn Met Arg Ser Gly Asp Gly Val Gly Ser Ile Arg
65                  70                  75                  80

Glu Val Thr Val Val Ser Gly Leu Pro Ala Ser Thr Ser Thr Glu Arg
                85                  90                  95

Leu Glu Ile Leu Asp Asp Lys His Leu Leu Ser Phe Arg Val Val
            100                 105                 110

Gly Gly Glu His Arg Leu His Asn Tyr Arg Ser Val Thr Ser Val Asn
        115                 120                 125

Glu Phe Lys Asn Pro Asp Asn Gly Lys Val Tyr Thr Ile Val Leu Glu
    130                 135                 140

Ser Tyr Val Val Asp Ile Pro Glu Gly Asn Thr Gly Val Asp Thr Lys
145                 150                 155                 160

Met Phe Val Asp Thr Val Val Lys Leu Asn Leu Gln Lys Leu Gly Glu
                165                 170                 175
```

<210> SEQ ID NO 98
<211> LENGTH: 172
<212> TYPE: PRT
<213> ORGANISM: Glycine max
<220> FEATURE:
<223> OTHER INFORMATION: soybean Glyma06g05440.1 protein

<400> SEQUENCE: 98

```
Glu Phe Thr Glu Leu Glu Ser Thr Ile Asn Thr His His Lys Phe Glu
1               5                   10                  15

Ala Ser Pro Glu Ile Cys Ser Ser Ile Ile Ala Gln Arg Ile Asp Ala
            20                  25                  30

Pro Ala His Thr Val Trp Pro Leu Val Arg Ser Phe Glu Asn Pro Gln
```

```
                  35                  40                  45
Lys Tyr Lys His Phe Val Lys Ser Cys Asn Met Arg Ser Gly Asp Gly
 50                  55                  60

Gly Val Gly Ser Ile Arg Glu Val Thr Val Val Ser Gly Leu Pro Ala
 65                  70                  75                  80

Ser Thr Ser Thr Glu Arg Leu Glu Ile Leu Asp Asp Asp Asn His Leu
                 85                  90                  95

Leu Ser Phe Arg Val Val Gly Gly Glu His Arg Leu His Asn Tyr Arg
                100                 105                 110

Ser Val Thr Ser Val Asn Glu Phe Lys Arg Pro Asp Asn Gly Lys Val
                115                 120                 125

Tyr Thr Ile Val Leu Glu Ser Tyr Val Val Asp Ile Pro Glu Gly Asn
                130                 135                 140

Thr Gly Val Asp Thr Lys Met Phe Val Asp Thr Val Val Lys Leu Asn
145                 150                 155                 160

Leu Gln Lys Leu Gly Glu Val Ala Met Ala Thr Asn
                165                 170

<210> SEQ ID NO 99
<211> LENGTH: 191
<212> TYPE: PRT
<213> ORGANISM: Glycine max
<220> FEATURE:
<223> OTHER INFORMATION: soybean Glyma06g13150.1 protein

<400> SEQUENCE: 99

Met Thr Glu Leu Ser Ser Arg Glu Val Glu Tyr Ile Arg Arg His His
  1               5                  10                  15

Ser Lys Ala Ala Glu Asp Asn Gln Cys Ala Ser Ala Leu Val Lys His
                 20                  25                  30

Ile Arg Ala Pro Leu Pro Leu Val Trp Ser Leu Val Arg Arg Phe Asp
                 35                  40                  45

Glu Pro Gln Lys Tyr Lys Pro Phe Val Ser Arg Cys Val Val Arg Gly
 50                  55                  60

Asn Leu Glu Ile Gly Ser Leu Arg Glu Val Asp Val Lys Ser Gly Leu
 65                  70                  75                  80

Pro Ala Thr Thr Ser Thr Glu Arg Leu Glu Ile Leu Asp Asp Asn His
                 85                  90                  95

His Ile Leu Ser Val Arg Ile Ile Gly Gly Asp His Arg Leu Arg Asn
                100                 105                 110

Tyr Ser Ser Ile Met Ser Leu His Pro Glu Ile Val Asp Gly Arg Pro
                115                 120                 125

Gly Thr Leu Val Ile Glu Ser Phe Val Val Asp Ile Pro Glu Gly Asn
                130                 135                 140

Thr Lys Asp Glu Thr Cys Tyr Phe Val Glu Ala Leu Ile Lys Cys Asn
145                 150                 155                 160

Leu Lys Ser Leu Ala Asp Val Ser Glu Gly Leu Thr Leu Gln Asp His
                165                 170                 175

Thr Glu Pro Ile Asp Arg Lys Tyr Glu Leu Leu Ile Thr Arg Gly
                180                 185                 190

<210> SEQ ID NO 100
<211> LENGTH: 185
<212> TYPE: PRT
<213> ORGANISM: Glycine max
<220> FEATURE:
<223> OTHER INFORMATION: soybean Glyma07g06270.1 protein
```

<400> SEQUENCE: 100

```
Met Asn Gly Gly Glu Ser Tyr Gly Ala Ile Glu Thr Gln Tyr Ile Arg
1               5                   10                  15

Arg His His Lys His Glu Pro Arg Glu Asn Gln Cys Thr Ser Ala Leu
            20                  25                  30

Val Lys His Ile Arg Ala Pro Val His Leu Val Trp Ser Leu Val Arg
        35                  40                  45

Arg Phe Asp Gln Pro Gln Lys Tyr Lys Pro Phe Val Ser Arg Cys Ile
    50                  55                  60

Met Gln Gly Asp Leu Gly Ile Gly Ser Val Arg Glu Val Asn Val Lys
65                  70                  75                  80

Ser Gly Leu Pro Ala Thr Thr Ser Thr Glu Arg Leu Glu Gln Leu Asp
                85                  90                  95

Asp Glu Glu His Ile Leu Gly Ile Arg Ile Val Gly Gly Asp His Arg
            100                 105                 110

Leu Arg Asn Tyr Ser Ser Ile Ile Thr Val His Pro Glu Val Ile Asp
        115                 120                 125

Gly Arg Pro Gly Thr Met Val Ile Glu Ser Phe Val Val Asp Val Pro
    130                 135                 140

Asp Gly Asn Thr Arg Asp Glu Thr Cys Tyr Phe Val Glu Ala Leu Ile
145                 150                 155                 160

Arg Cys Asn Leu Ser Ser Leu Ala Asp Val Ser Glu Arg Met Ala Val
                165                 170                 175

Gln Gly Arg Thr Asn Pro Ile Asn His
            180                 185
```

<210> SEQ ID NO 101
<211> LENGTH: 178
<212> TYPE: PRT
<213> ORGANISM: Glycine max
<220> FEATURE:
<223> OTHER INFORMATION: soybean Glyma07g19120.1 protein

<400> SEQUENCE: 101

```
Met Ser Pro Asn Asn Pro Ser Thr Ile Val Ser Asp Ala Val Ala Arg
1               5                   10                  15

His His Thr His Val Val Ser Pro His Gln Cys Cys Ser Ala Val Val
            20                  25                  30

Gln Glu Ile Ala Ala Pro Val Ser Thr Val Trp Ser Val Val Arg Arg
        35                  40                  45

Phe Asp Asn Pro Gln Ala Tyr Lys His Phe Val Lys Ser Cys His Val
    50                  55                  60

Ile Leu Gly Asp Gly Asp Val Gly Thr Leu Arg Glu Val Arg Val Ile
65                  70                  75                  80

Ser Gly Leu Pro Ala Ala Val Ser Thr Glu Arg Leu Asp Val Leu Asp
                85                  90                  95

Asp Glu Arg His Val Ile Gly Phe Ser Met Val Gly Gly Asp His Arg
            100                 105                 110

Leu Ser Asn Tyr Arg Ser Val Thr Ile Leu His Pro Arg Ser Ala Thr
        115                 120                 125

Asp Thr Val Val Val Glu Ser Tyr Val Val Asp Val Pro Ala Gly Asn
    130                 135                 140

Thr Thr Glu Asp Thr Arg Val Phe Val Asp Thr Ile Leu Arg Cys Asn
145                 150                 155                 160
```

```
Leu Gln Ser Leu Ala Lys Phe Ala Glu Asn Leu Thr Asn Lys Leu His
                165                 170                 175
Gln Arg

<210> SEQ ID NO 102
<211> LENGTH: 246
<212> TYPE: PRT
<213> ORGANISM: Glycine max
<220> FEATURE:
<223> OTHER INFORMATION: soybean Glyma08g36770.1 protein

<400> SEQUENCE: 102

Met Ser Arg Ser His Asn Lys Arg Lys Pro Phe Ser Phe Ile Phe Lys
1               5                   10                  15

Ile Thr Leu Leu Glu Leu Leu Ser Ser Leu Leu Ser Ser Ser Leu Arg
            20                  25                  30

Phe Ala Met Asp Lys Thr His Ser Gly Glu Glu Gln Asp Pro Asn Pro
        35                  40                  45

Thr His Pro Thr Arg Asn His Leu Asp Pro Pro Gly Leu Thr Pro
    50                  55                  60

Glu Glu Phe Glu Asp Leu Lys Pro Ser Val Leu Glu His His Thr Tyr
65                  70                  75                  80

Ser Val Thr Pro Thr Arg Gln Cys Ser Ser Leu Leu Ala Gln Arg Ile
                85                  90                  95

His Ala Pro Pro His Thr Val Trp Thr Val Val Arg Cys Phe Asp Asn
            100                 105                 110

Pro Gln Ala Tyr Lys His Phe Ile Lys Ser Cys His Val Lys Glu Gly
        115                 120                 125

Phe Gln Leu Ala Val Gly Ser Thr Arg Asp Val His Val Ile Ser Gly
    130                 135                 140

Leu Pro Ala Ala Thr Ser Thr Glu Arg Leu Asp Leu Leu Asp Asp Asp
145                 150                 155                 160

Arg His Val Ile Gly Phe Thr Ile Val Gly Gly Asp His Arg Leu Arg
                165                 170                 175

Asn Tyr Arg Ser Val Thr Ser Val His Gly Phe Glu Arg Asp Gly Lys
            180                 185                 190

Ile Trp Thr Val Val Leu Glu Ser Tyr Val Val Asp Val Pro Glu Gly
        195                 200                 205

Asn Thr Glu Glu Asp Thr Arg Leu Phe Ala Asp Thr Val Val Lys Leu
    210                 215                 220

Asn Leu Gln Lys Leu Ala Ser Val Thr Glu Gly Met Cys Gly Asp Ser
225                 230                 235                 240

Asp Gly Lys Gly Asn Asn
                245

<210> SEQ ID NO 103
<211> LENGTH: 223
<212> TYPE: PRT
<213> ORGANISM: Glycine max
<220> FEATURE:
<223> OTHER INFORMATION: soybean Glyma09g33700.1 protein

<400> SEQUENCE: 103

Met Glu Lys Ala Glu Ser Ser Ala Ser Thr Ser Glu Pro Asp Ser Asp
1               5                   10                  15

Asp Asn His His Arg His Pro Thr Asn His His Leu Asn Pro Pro Ser
            20                  25                  30
```

Gly Leu Thr Pro Leu Glu Phe Ala Ser Leu Val Pro Ser Val Ala Glu
            35                  40                  45

His His Ser Tyr Leu Val Gly Pro Gly Gln Cys Ser Ser Leu Leu Ala
 50                  55                  60

Gln Arg Val His Ala Pro Pro Asp Ala Val Trp Ser Phe Val Arg Arg
 65                  70                  75                  80

Phe Asp Lys Pro Gln Thr Tyr Lys His Phe Ile Lys Ser Cys Ala Val
                 85                  90                  95

Lys Glu Pro Phe His Met Ala Val Gly Val Thr Arg Asp Val Asn Val
            100                 105                 110

Ile Ser Gly Leu Pro Ala Ala Thr Ser Thr Glu Arg Leu Asp Phe Leu
            115                 120                 125

Asp Asp Val Arg Arg Val Thr Gly Phe Ser Ile Ile Gly Gly Glu His
130                 135                 140

Arg Leu Arg Asn Tyr Arg Ser Val Thr Thr Val His Ser Phe Asp Asp
145                 150                 155                 160

Asp Asn Ala Ser Ala Asp Gly Lys Ile Tyr Thr Val Val Leu Glu Ser
                165                 170                 175

Tyr Val Val Asp Val Pro Asp Gly Asn Thr Glu Glu Asp Thr Arg Leu
            180                 185                 190

Phe Ala Asp Thr Val Val Lys Leu Asn Leu Gln Lys Leu Ala Ser Val
            195                 200                 205

Thr Glu Gly Thr Asn Gly Asp Gly Asp Gly Lys Pro His Ser Arg
210                 215                 220

<210> SEQ ID NO 104
<211> LENGTH: 229
<212> TYPE: PRT
<213> ORGANISM: Glycine max
<220> FEATURE:
<223> OTHER INFORMATION: soybean Glyma11g35670.1 protein

<400> SEQUENCE: 104

Met Pro Ser Ser Leu His Phe Asp Arg Phe Asn Pro Ile Thr His Ala
 1               5                  10                  15

Ala Thr Thr Val Ala Ile Ala Asn Gly Val Asn Cys Pro Lys Gln Pro
                20                  25                  30

Gln Ala Pro Pro Ser Ser Thr Ala Ala Arg Arg Leu Val Val Pro Ser
            35                  40                  45

Leu Ser Ser Gly Arg Gly Ile Ala Ala Pro Asp Thr Val Ala Leu His
 50                  55                  60

His Ala His Val Val Asp Pro Asn Gln Cys Cys Ser Ile Val Thr Gln
 65                  70                  75                  80

His Ile Asn Ala Pro Val Ser Ala Val Trp Ala Val Val Arg Arg Phe
                 85                  90                  95

Asp Asn Pro Gln Gly Tyr Lys Asn Phe Val Arg Ser Cys His Val Ile
            100                 105                 110

Thr Gly Asp Gly Ile Arg Val Gly Ala Val Arg Glu Val Arg Val Val
            115                 120                 125

Ser Gly Leu Pro Ala Glu Thr Ser Thr Glu Arg Leu Glu Ile Leu Asp
130                 135                 140

Asp Glu Arg His Val Ile Ser Phe Ser Met Val Gly Gly Asp His Arg
145                 150                 155                 160

Leu Arg Asn Tyr Gln Ser Val Thr Thr Leu His Ala Asn Gly Asn Gly
                165                 170                 175

```
Thr Leu Val Ile Glu Ser Tyr Val Val Asp Val Pro Gln Gly Asn Thr
            180                 185                 190

Lys Glu Glu Thr Cys Val Phe Val Asp Thr Ile Val Arg Cys Asn Leu
        195                 200                 205

Gln Ser Leu Ala Gln Ile Ala Glu Asn Arg Thr Asn Asn Cys Glu His
        210                 215                 220

Thr Ala Gln His Cys
225

<210> SEQ ID NO 105
<211> LENGTH: 191
<212> TYPE: PRT
<213> ORGANISM: Glycine max
<220> FEATURE:
<223> OTHER INFORMATION: soybean Glyma13g08120.1 protein

<400> SEQUENCE: 105

Met Asn Gly Ile Gly Asn Asp Gly Gly Gly Gly Leu Ser Asn Val Glu
1               5                   10                  15

Met Glu Tyr Ile Arg Arg His His Arg His Glu Pro Gly Glu Asn Gln
            20                  25                  30

Cys Gly Ser Ala Leu Val Lys His Ile Arg Ala Pro Val Pro Gln Val
        35                  40                  45

Trp Ser Leu Val Arg Arg Phe Asp Gln Pro Gln Lys Tyr Lys Pro Phe
    50                  55                  60

Val Ser Arg Cys Val Val Arg Gly Asn Leu Glu Ile Gly Ser Leu Arg
65                  70                  75                  80

Glu Val Asp Val Lys Ser Gly Leu Pro Ala Thr Thr Ser Thr Glu Arg
                85                  90                  95

Leu Glu Leu Leu Asp Asp Asn Glu His Leu Leu Ser Ile Arg Ile Ile
            100                 105                 110

Gly Gly Asp His Arg Leu Arg Asn Tyr Ser Ser Ile Met Ser Leu His
        115                 120                 125

Pro Glu Ile Ile Asp Gly Arg Pro Gly Thr Leu Val Ile Glu Ser Phe
    130                 135                 140

Val Val Asp Val Pro Glu Gly Asn Thr Lys Asp Glu Thr Cys Tyr Phe
145                 150                 155                 160

Val Glu Ala Leu Ile Lys Cys Asn Leu Lys Ser Leu Ala Asp Val Ser
                165                 170                 175

Glu Gly Ile Ala Val Gln Asp Arg Thr Glu Pro Ile Asp Arg Ile
            180                 185                 190

<210> SEQ ID NO 106
<211> LENGTH: 169
<212> TYPE: PRT
<213> ORGANISM: Glycine max
<220> FEATURE:
<223> OTHER INFORMATION: soybean Glyma14g06100.1 protein

<400> SEQUENCE: 106

Met Val Ala Arg His His Ala His Ala Val Gly Pro Asn Gln Cys Cys
1               5                   10                  15

Ser Phe Val Ile Gln Ala Ile Asp Ala Pro Val Ser Ala Val Trp Pro
            20                  25                  30

Val Val Arg Arg Phe Asp Asn Pro Gln Ala Tyr Lys His Phe Val Lys
        35                  40                  45

Ser Cys His Val Val Ala Ala Gly Gly Ala Gly Gly Asp Gly Gly Ile
    50                  55                  60
```

His Val Gly Ala Leu Arg Glu Val Arg Val Val Ser Gly Leu Pro Ala
65                  70                  75                  80

Val Ser Ser Thr Glu Arg Leu Glu Ile Leu Asp Asp Glu Arg His Val
                85                  90                  95

Met Ser Phe Ser Val Val Gly Gly Asp His Arg Leu Arg Asn Tyr Arg
            100                 105                 110

Ser Val Thr Thr Leu His Gly Asp Gly Ser Asn Gly Gly Thr Val Val
        115                 120                 125

Ile Glu Ser Tyr Val Val Asp Ile Pro Ala Gly Asn Thr Lys Glu Glu
130                 135                 140

Thr Cys Val Phe Val Asp Thr Ile Val Arg Cys Asn Leu Gln Ser Leu
145                 150                 155                 160

Ala Gln Met Ala Glu Asn Met Gly Ser
                165

<210> SEQ ID NO 107
<211> LENGTH: 210
<212> TYPE: PRT
<213> ORGANISM: Glycine max
<220> FEATURE:
<223> OTHER INFORMATION: soybean Glyma14g10730.1 protein

<400> SEQUENCE: 107

Met Thr Ile Leu Pro His Ser Asn Asn Lys Ser Ser Asn His Lys Phe
1               5                   10                  15

Ile Ala His Gln Asn Tyr Met Ala Ser Glu Thr His His Val Gln
            20                  25                  30

Gly Leu Thr Pro Glu Glu Leu Thr Lys Leu Glu Pro Ile Ile Lys Lys
        35                  40                  45

Tyr His Leu Phe Glu Gln Ser Pro Asn Thr Cys Phe Ser Ile Ile Thr
    50                  55                  60

Tyr Arg Ile Glu Ala Pro Ala Lys Ala Val Trp Pro Phe Val Arg Ser
65                  70                  75                  80

Phe Asp Asn Pro Gln Lys Tyr Lys His Phe Ile Lys Gly Cys Asn Met
                85                  90                  95

Arg Gly Asp Gly Gly Val Gly Ser Ile Arg Glu Val Thr Val Val Ser
            100                 105                 110

Gly Leu Pro Ala Ser Thr Ser Thr Glu Arg Leu Glu Ile Leu Asp Asp
        115                 120                 125

Asp Lys His Val Leu Ser Phe Arg Val Val Gly Gly Glu His Arg Leu
130                 135                 140

Lys Asn Tyr Arg Ser Val Thr Ser Val Asn Glu Phe Asn Lys Glu Gly
145                 150                 155                 160

Lys Val Tyr Thr Ile Val Leu Glu Ser Tyr Ile Val Asp Ile Pro Glu
                165                 170                 175

Gly Asn Thr Glu Glu Asp Thr Lys Met Phe Val Asp Thr Val Val Lys
            180                 185                 190

Leu Asn Leu Gln Lys Leu Gly Val Val Ala Met Ala Ser Ser Met His
        195                 200                 205

Gly Gln
    210

<210> SEQ ID NO 108
<211> LENGTH: 193
<212> TYPE: PRT
<213> ORGANISM: Glycine max

```
<220> FEATURE:
<223> OTHER INFORMATION: soybean Glyma14g30260.1 protein

<400> SEQUENCE: 108

Met Asn Arg Ile Gly Asn Gly Gly Gly Gly Gly Gly Leu Ser Asn
1               5                   10                  15

Val Glu Met Glu Tyr Ile Arg Arg His Arg His Glu Pro Gly Glu
            20                  25                  30

Asn Gln Cys Gly Ser Ala Leu Val Lys His Ile Arg Ala Pro Val Pro
        35                  40                  45

Gln Val Trp Ser Leu Val Arg Arg Phe Asp Gln Pro Gln Lys Tyr Lys
    50                  55                  60

Pro Phe Ile Ser Arg Cys Val Val Arg Gly Asn Leu Glu Ile Gly Ser
65                  70                  75                  80

Leu Arg Glu Val Asp Val Lys Ser Gly Leu Pro Ala Thr Thr Ser Thr
                85                  90                  95

Glu Arg Leu Glu Leu Leu Asp Asp Asn Glu His Ile Leu Ser Ile Arg
            100                 105                 110

Ile Ile Gly Gly Asp His Arg Leu Arg Asn Tyr Ser Ser Ile Met Ser
        115                 120                 125

Leu His Pro Glu Ile Ile Asp Gly Arg Pro Gly Thr Leu Val Ile Glu
    130                 135                 140

Ser Phe Val Val Asp Val Pro Glu Gly Asn Thr Lys Asp Glu Thr Cys
145                 150                 155                 160

Tyr Phe Val Glu Ala Leu Ile Lys Cys Asn Leu Lys Ser Leu Ala Asp
                165                 170                 175

Val Ser Glu Gly Leu Ala Val Gln Asp Cys Thr Glu Pro Ile Asp Arg
            180                 185                 190

Ile

<210> SEQ ID NO 109
<211> LENGTH: 188
<212> TYPE: PRT
<213> ORGANISM: Glycine max
<220> FEATURE:
<223> OTHER INFORMATION: soybean Glyma17g34800.1 protein

<400> SEQUENCE: 109

Met Ala Ser Glu Thr His His His Val Gln Gly Leu Thr Pro Glu Glu
1               5                   10                  15

Leu Thr Gln Leu Glu Pro Ile Ile Lys Lys Tyr His Leu Phe Glu Ala
            20                  25                  30

Ser Ser Asn Lys Cys Phe Ser Ile Ile Thr His Arg Ile Glu Ala Pro
        35                  40                  45

Ala Ser Ser Val Trp Pro Leu Val Arg Asn Phe Asp Asn Pro Gln Lys
    50                  55                  60

Tyr Lys His Phe Ile Lys Gly Cys Asn Met Lys Gly Asp Gly Ser Val
65                  70                  75                  80

Gly Ser Ile Arg Glu Val Thr Val Val Ser Gly Leu Pro Ala Ser Thr
                85                  90                  95

Ser Thr Glu Arg Leu Glu Ile Leu Asp Asp Lys His Val Leu Ser
            100                 105                 110

Phe Arg Val Val Gly Gly Glu His Arg Leu Gln Asn Tyr Arg Ser Val
        115                 120                 125

Thr Ser Val Asn Glu Phe His Lys Glu Gly Lys Val Tyr Thr Ile Val
    130                 135                 140
```

```
Leu Glu Ser Tyr Ile Val Asp Ile Pro Glu Gly Asn Thr Glu Glu Asp
145                 150                 155                 160

Thr Lys Met Phe Val Asp Thr Val Val Lys Leu Asn Leu Gln Lys Leu
                165                 170                 175

Gly Val Val Ala Met Ala Ser Ser Met Asn Gly Arg
            180                 185

<210> SEQ ID NO 110
<211> LENGTH: 177
<212> TYPE: PRT
<213> ORGANISM: Glycine max
<220> FEATURE:
<223> OTHER INFORMATION: soybean Glyma18g43680.1 protein

<400> SEQUENCE: 110

Met Leu Pro Asn Asn Pro Ser Thr Ile Val Pro Asp Ala Val Ala Arg
1               5                   10                  15

His His Thr His Val Val Ser Pro Gln Gln Cys Cys Ser Ala Val Val
                20                  25                  30

Gln Glu Ile Ala Ala Pro Val Ser Thr Val Trp Ser Val Val Arg Arg
            35                  40                  45

Phe Asp Asn Pro Gln Ala Tyr Lys His Phe Val Lys Ser Cys His Val
50                  55                  60

Ile Leu Gly Asp Gly Asp Val Gly Thr Leu Arg Glu Val His Val Ile
65                  70                  75                  80

Ser Gly Leu Pro Ala Ala Val Ser Thr Glu Arg Leu Asp Val Leu Asp
                85                  90                  95

Asp Glu Arg His Val Ile Gly Phe Ser Met Val Gly Gly Asp His Arg
            100                 105                 110

Leu Phe Asn Tyr Arg Ser Val Thr Thr Leu His Pro Arg Ser Ala Ala
            115                 120                 125

Gly Thr Val Val Val Glu Ser Tyr Val Val Asp Val Pro Pro Gly Asn
        130                 135                 140

Thr Thr Glu Asp Thr Arg Val Phe Val Asp Thr Ile Leu Arg Cys Asn
145                 150                 155                 160

Leu Gln Ser Leu Ala Lys Phe Ala Glu Asn Leu Thr Lys Leu His Gln
                165                 170                 175

Arg

<210> SEQ ID NO 111
<211> LENGTH: 185
<212> TYPE: PRT
<213> ORGANISM: Glycine max
<220> FEATURE:
<223> OTHER INFORMATION: soybean Glyma07g06270.2 protein

<400> SEQUENCE: 111

Met Asn Gly Gly Glu Ser Tyr Gly Ala Ile Glu Thr Gln Tyr Ile Arg
1               5                   10                  15

Arg His His Lys His Glu Pro Arg Glu Asn Gln Cys Thr Ser Ala Leu
                20                  25                  30

Val Lys His Ile Arg Ala Pro Val His Leu Val Trp Ser Leu Val Arg
            35                  40                  45

Arg Phe Asp Gln Pro Gln Lys Tyr Lys Pro Phe Val Ser Arg Cys Ile
50                  55                  60

Met Gln Gly Asp Leu Gly Ile Gly Ser Val Arg Glu Val Asn Val Lys
65                  70                  75                  80
```

```
Ser Gly Leu Pro Ala Thr Thr Ser Thr Glu Arg Leu Glu Gln Leu Asp
             85                  90                  95

Asp Glu Glu His Ile Leu Gly Ile Arg Ile Val Gly Gly Asp His Arg
        100                 105                 110

Leu Arg Asn Tyr Ser Ser Ile Ile Thr Val His Pro Glu Val Ile Asp
    115                 120                 125

Gly Arg Pro Gly Thr Met Val Ile Glu Ser Phe Val Val Asp Val Pro
130                 135                 140

Asp Gly Asn Thr Arg Asp Glu Thr Cys Tyr Phe Val Glu Ala Leu Ile
145                 150                 155                 160

Arg Cys Asn Leu Ser Ser Leu Ala Asp Val Ser Glu Arg Met Ala Val
                165                 170                 175

Gln Gly Arg Thr Asn Pro Ile Asn His
            180                 185
```

<210> SEQ ID NO 112
<211> LENGTH: 191
<212> TYPE: PRT
<213> ORGANISM: Glycine max
<220> FEATURE:
<223> OTHER INFORMATION: soybean Glyma16g02910.1 protein

<400> SEQUENCE: 112

```
Met Gly Ile Thr Ile Gly Ile Gln Cys Leu Glu Ile Glu Glu Ile Ser
1               5                   10                  15

Ile Cys Asp Gly Met Phe Cys Tyr Leu Val Asp Phe Asp Val Lys
            20                  25                  30

Glu Lys Met Asn Tyr Cys Leu Met Trp Phe Gly Tyr Phe Pro Ser Gln
        35                  40                  45

Val Trp Ser Leu Val Arg Arg Phe Asp Gln Pro Gln Lys Tyr Lys Pro
    50                  55                  60

Phe Val Ser Arg Cys Ile Met Gln Gly Asp Leu Gly Ile Gly Ser Val
65                  70                  75                  80

Arg Glu Val Asn Val Lys Ser Gly Leu Pro Ala Thr Thr Ser Thr Glu
                85                  90                  95

Arg Leu Glu Gln Leu Asp Asp Glu Glu His Ile Leu Gly Ile Arg Ile
            100                 105                 110

Val Gly Gly Asp His Arg Leu Arg Asn Tyr Ser Ser Ile Ile Thr Val
        115                 120                 125

His Pro Glu Val Ile Asp Gly Arg Pro Ser Thr Met Val Ile Glu Ser
130                 135                 140

Phe Val Val Asp Val Pro Asp Gly Asn Thr Arg Asp Glu Thr Cys Tyr
145                 150                 155                 160

Phe Val Glu Ala Leu Ile Arg Cys Asn Leu Ser Ser Leu Ala Asp Val
                165                 170                 175

Ser Glu Arg Met Ala Val Gln Gly Arg Thr Asp Pro Ile Asn His
            180                 185                 190
```

<210> SEQ ID NO 113
<211> LENGTH: 185
<212> TYPE: PRT
<213> ORGANISM: Artificial Sequence
<220> FEATURE:
<223> OTHER INFORMATION: synthetic PYR/PYL receptor protein

<400> SEQUENCE: 113

Met Asn Gly Gly Glu Ser Tyr Gly Ala Ile Glu Thr Gln Tyr Ile Arg

```
1               5                   10                  15
Arg His His Lys His Glu Pro Arg Glu Asn Gln Cys Thr Ser Ala Leu
            20                  25                  30

Val Lys His Ile Arg Ala Pro His Leu Val Trp Ser Leu Val Arg
            35                  40                  45

Arg Phe Asp Gln Pro Gln Lys Tyr Lys Pro Phe Val Ser Arg Cys Ile
        50                  55                  60

Met Gln Gly Asp Leu Gly Ile Gly Ser Val Arg Glu Val Asn Val Lys
65                  70                  75                  80

Ser Gly Leu Pro Ala Thr Thr Ser Thr Glu Arg Leu Glu Gln Leu Asp
                85                  90                  95

Asp Glu Glu His Ile Leu Gly Ile Arg Ile Val Gly Gly Asp His Arg
            100                 105                 110

Leu Arg Asn Tyr Ser Ser Ile Ile Thr Val His Pro Glu Val Ile Asp
            115                 120                 125

Gly Arg Pro Ser Thr Met Val Ile Glu Ser Phe Val Val Asp Val Pro
        130                 135                 140

Asp Gly Asn Thr Arg Asp Glu Thr Cys Tyr Phe Val Glu Ala Leu Ile
145                 150                 155                 160

Arg Cys Asn Leu Ser Ser Leu Ala Asp Val Ser Glu Arg Met Ala Val
                165                 170                 175

Gln Gly Arg Thr Asp Pro Ile Asn His
            180                 185

<210> SEQ ID NO 114
<211> LENGTH: 204
<212> TYPE: PRT
<213> ORGANISM: Sorghum bicolor
<220> FEATURE:
<223> OTHER INFORMATION: sorghum Sb10g022200 protein

<400> SEQUENCE: 114

Met Glu Thr His Val Glu Arg Ala Leu Arg Ala Thr Leu Thr Glu Ala
1               5                   10                  15

Glu Val Arg Ala Leu Glu Pro Ala Val Arg Glu His His Thr Phe Pro
            20                  25                  30

Ala Gly Arg Val Ala Ala Gly Thr Thr Thr Pro Thr Pro Thr Thr Cys
        35                  40                  45

Thr Ser Leu Val Ala Gln Arg Val Ser Ala Pro Val Arg Ala Val Trp
    50                  55                  60

Pro Ile Val Arg Ser Phe Gly Asn Pro Gln Arg Tyr Lys His Phe Val
65                  70                  75                  80

Arg Thr Cys Ala Leu Ala Ala Gly Asp Gly Ala Ser Val Gly Ser Val
                85                  90                  95

Arg Glu Val Thr Val Val Ser Gly Leu Pro Ala Ser Ser Ser Thr Glu
            100                 105                 110

Arg Leu Glu Val Leu Asp Asp Arg His Ile Leu Ser Phe Arg Val
            115                 120                 125

Val Gly Gly Asp His Arg Leu Arg Asn Tyr Arg Ser Val Thr Ser Val
        130                 135                 140

Thr Glu Phe Gln Pro Gly Pro Tyr Cys Val Val Glu Ser Tyr Ala
145                 150                 155                 160

Val Asp Val Pro Glu Gly Asn Thr Ala Glu Asp Thr Arg Met Phe Thr
                165                 170                 175

Asp Thr Val Val Arg Leu Asn Leu Gln Lys Leu Ala Ala Val Ala Glu
```

```
            180                 185                 190
Glu Ser Ala Ala Ala Ala Ala Gly Asn Arg Arg
        195                 200

<210> SEQ ID NO 115
<211> LENGTH: 204
<212> TYPE: PRT
<213> ORGANISM: Sorghum bicolor
<220> FEATURE:
<223> OTHER INFORMATION: sorghum Sb04g008040 protein

<400> SEQUENCE: 115

Met Glu Pro His Met Glu Thr Ala Leu Arg Gln Gly Gly Leu Ser Glu
1               5                   10                  15

Leu Glu Gln Arg Glu Leu Glu Pro Val Val Arg Ala His His Thr Phe
            20                  25                  30

Pro Gly Arg Ser Pro Gly Thr Thr Cys Thr Ser Leu Val Thr Gln Arg
        35                  40                  45

Val Asp Ala Pro Leu Ser Ala Val Trp Pro Ile Val Arg Gly Phe Ala
    50                  55                  60

Ala Pro Gln Arg Tyr Lys His Phe Ile Lys Ser Cys Asp Leu Arg Ser
65                  70                  75                  80

Gly Asp Gly Ala Thr Val Gly Ser Val Arg Glu Val Thr Val Val Ser
                85                  90                  95

Gly Leu Pro Ala Ser Thr Ser Thr Glu Arg Leu Glu Ile Leu Asp Asp
            100                 105                 110

Asp Arg His Ile Leu Ser Phe Arg Val Val Gly Gly Asp His Arg Leu
        115                 120                 125

Arg Asn Tyr Arg Ser Val Thr Ser Val Thr Glu Phe His His His His
    130                 135                 140

Gln Ala Ala Ala Gly Arg Pro Tyr Cys Val Val Glu Ser Tyr Val
145                 150                 155                 160

Val Asp Val Pro Glu Gly Asn Thr Glu Glu Asp Thr Arg Met Phe Thr
                165                 170                 175

Asp Thr Val Val Lys Leu Asn Leu Gln Lys Leu Ala Ala Ile Ala Thr
            180                 185                 190

Ser Ser Ala Ala Ala Ala Ser Asn Ser Ser Thr
        195                 200

<210> SEQ ID NO 116
<211> LENGTH: 258
<212> TYPE: PRT
<213> ORGANISM: Sorghum bicolor
<220> FEATURE:
<223> OTHER INFORMATION: sorghum Sb01g028330 protein

<400> SEQUENCE: 116

Met Val Glu Ser Pro Asn Pro Asn Ser Pro Ser Arg Pro Leu Cys Ile
1               5                   10                  15

Lys Tyr Thr Arg Ala Pro Ala Arg His Phe Ser Pro Pro Leu Pro Phe
            20                  25                  30

Ser Ser Leu Ile Ile Ser Ala Asn Pro Ile Glu Pro Lys Ala Met Asp
        35                  40                  45

Lys Gln Gly Ala Gly Gly Asp Val Glu Val Pro Ala Gly Leu Gly Leu
    50                  55                  60

Thr Ala Ala Glu Tyr Glu Gln Leu Arg Ser Thr Val Asp Ala His His
65                  70                  75                  80
```

```
Arg Tyr Ala Val Gly Glu Gly Gln Cys Ser Ser Leu Leu Ala Gln Arg
                85                  90                  95

Ile Gln Ala Pro Pro Ala Ala Val Trp Ala Ile Val Arg Arg Phe Asp
            100                 105                 110

Cys Pro Gln Val Tyr Lys His Phe Ile Arg Ser Cys Ala Leu Arg Pro
            115                 120                 125

Asp Pro Glu Ala Gly Asp Ala Leu Arg Pro Gly Arg Leu Arg Glu Val
            130                 135                 140

Ser Val Ile Ser Gly Leu Pro Ala Ser Thr Ser Thr Glu Arg Leu Asp
145                 150                 155                 160

Leu Leu Asp Asp Ala Ala Arg Val Phe Gly Phe Ser Ile Thr Gly Gly
                165                 170                 175

Glu His Arg Leu Arg Asn Tyr Arg Ser Val Thr Thr Val Ser Glu Leu
            180                 185                 190

Ala Asp Pro Gly Ile Cys Thr Val Val Leu Glu Ser Tyr Val Val Asp
            195                 200                 205

Val Pro Asp Gly Asn Thr Glu Asp Asp Thr Arg Leu Phe Ala Asp Thr
            210                 215                 220

Val Ile Arg Leu Asn Leu Gln Lys Leu Lys Ser Val Ala Glu Ala Asn
225                 230                 235                 240

Ala Ala Ala Ala Ala Ser Phe Val Ser Val Val Pro Pro Glu Pro
                245                 250                 255

Glu Glu

<210> SEQ ID NO 117
<211> LENGTH: 222
<212> TYPE: PRT
<213> ORGANISM: Sorghum bicolor
<220> FEATURE:
<223> OTHER INFORMATION: sorghum Sb01g038150 protein

<400> SEQUENCE: 117

Met Pro Cys Leu Gln Ala Ser Ser Ser Pro Gly Ser Met Pro His Gln
1               5                   10                  15

His His Gly Arg Val Leu Ala Gly Val Gly Cys Ala Ala Glu Val Ala
            20                  25                  30

Ala Ala Val Ala Ala Thr Ser Pro Ala Ala Gly Met Arg Cys Gly
        35                  40                  45

Ala His Asp Gly Glu Val Pro Ala Glu Ala Ala Arg His His Glu His
    50                  55                  60

Ala Ala Pro Gly Pro Gly Arg Cys Cys Ser Ala Val Val Gln His Val
65                  70                  75                  80

Ala Ala Pro Ala Ser Ala Val Trp Ser Val Val Arg Arg Phe Asp Gln
                85                  90                  95

Pro Gln Ala Tyr Lys Arg Phe Val Arg Ser Cys Ala Leu Leu Ala Gly
            100                 105                 110

Asp Gly Gly Val Gly Thr Leu Arg Glu Val Arg Val Val Ser Gly Leu
            115                 120                 125

Pro Ala Ala Ser Ser Arg Glu Arg Leu Glu Val Leu Asp Asp Glu Ser
            130                 135                 140

His Val Leu Ser Phe Arg Val Val Gly Gly Glu His Arg Leu Gln Asn
145                 150                 155                 160

Tyr Leu Ser Val Thr Thr Val His Pro Ser Pro Ala Ala Pro Asp Ala
                165                 170                 175

Ala Thr Val Val Val Glu Ser Tyr Val Val Asp Val Pro Pro Gly Asn
```

```
                  180                 185                 190
Thr Pro Glu Asp Thr Arg Val Phe Val Asp Thr Ile Val Lys Cys Asn
            195                 200                 205

Leu Gln Ser Leu Ala Thr Thr Ala Glu Lys Leu Ala Ala Val
        210                 215                 220

<210> SEQ ID NO 118
<211> LENGTH: 211
<212> TYPE: PRT
<213> ORGANISM: Sorghum bicolor
<220> FEATURE:
<223> OTHER INFORMATION: sorghum Sb04g009280 protein

<400> SEQUENCE: 118

Met Val Glu Met Asp Gly Gly Val Gly Val Val Gly Gly Gln Gln
1               5                   10                  15

Thr Pro Ala Pro Arg Arg Trp Arg Leu Ala Asp Glu Leu Arg Cys Asp
            20                  25                  30

Leu Arg Ala Met Glu Thr Asp Tyr Val Arg Arg Phe His Arg His Glu
        35                  40                  45

Pro Arg Asp His Gln Cys Ser Ser Ala Val Ala Lys His Ile Lys Ala
50                  55                  60

Pro Val His Leu Val Trp Ser Leu Val Arg Arg Phe Asp Gln Pro Gln
65                  70                  75                  80

Leu Phe Lys Pro Phe Val Ser Arg Cys Glu Met Lys Gly Asn Ile Glu
                85                  90                  95

Ile Gly Ser Val Arg Glu Val Asn Val Lys Ser Gly Leu Pro Ala Thr
            100                 105                 110

Arg Ser Thr Glu Arg Leu Glu Leu Leu Asp Asp Asn Glu His Ile Leu
        115                 120                 125

Ser Val Lys Phe Val Gly Gly Asp His Arg Leu Gln Asn Tyr Ser Ser
    130                 135                 140

Ile Leu Thr Val His Pro Glu Val Ile Asp Gly Arg Pro Gly Thr Leu
145                 150                 155                 160

Val Ile Glu Ser Phe Val Val Asp Val Pro Asp Gly Asn Thr Lys Asp
                165                 170                 175

Glu Thr Cys Tyr Phe Val Glu Ala Leu Leu Lys Cys Asn Leu Lys Ser
            180                 185                 190

Leu Ala Glu Val Ser Glu Arg Gln Val Ile Lys Asp Gln Thr Glu Pro
        195                 200                 205

Leu Asp Arg
    210

<210> SEQ ID NO 119
<211> LENGTH: 216
<212> TYPE: PRT
<213> ORGANISM: Sorghum bicolor
<220> FEATURE:
<223> OTHER INFORMATION: sorghum Sb09g023180 protein

<400> SEQUENCE: 119

Met Pro Tyr Thr Ala Pro Arg Pro Ser Pro Gln Gln His Ser Arg Val
1               5                   10                  15

Thr Gly Gly Gly Ala Lys Ala Ala Ile Val Ala Ala Ser His Gly Ala
            20                  25                  30

Ser Cys Ala Ala Val Pro Ala Glu Val Ala Arg His His Glu His Ala
        35                  40                  45
```

```
Ala Arg Ala Gly Gln Cys Cys Ser Ala Val Val Gln Ala Ile Ala Ala
    50              55                  60

Pro Val Gly Ala Val Trp Ser Val Val Arg Arg Phe Asp Arg Pro Gln
65              70                  75                  80

Ala Tyr Lys His Phe Ile Arg Ser Cys Arg Leu Val Asp Asp Gly Gly
                85                  90                  95

Gly Gly Ala Gly Ala Gly Ala Gly Ala Thr Val Ala Val Gly Ser Val
            100             105                 110

Arg Glu Val Arg Val Val Ser Gly Leu Pro Ala Thr Ser Ser Arg Glu
        115             120                 125

Arg Leu Glu Ile Leu Asp Asp Glu Arg Arg Val Leu Ser Phe Arg Val
    130             135                 140

Val Gly Gly Glu His Arg Leu Ala Asn Tyr Arg Ser Val Thr Thr Val
145             150                 155                 160

His Glu Ala Glu Ala Gly Ala Gly Gly Thr Val Val Val Glu Ser Tyr
                165             170                 175

Val Val Asp Val Pro Pro Gly Asn Thr Ala Asp Glu Thr Arg Val Phe
            180                 185             190

Val Asp Thr Ile Val Arg Cys Asn Leu Gln Ser Leu Ala Arg Thr Ala
        195             200                 205

Glu Arg Leu Ala Leu Ala Leu Ala
    210             215
```